(12) United States Patent
Itami et al.

(10) Patent No.: US 9,266,909 B2
(45) Date of Patent: Feb. 23, 2016

(54) CYCLIC COMPOUND CONTAINING FUNCTIONAL GROUP OR CONTAINING NO FUNCTIONAL GROUP, AND METHOD FOR PRODUCING SAME

(71) Applicant: National University Corporation Nagoya University, Nagoya-shi (JP)

(72) Inventors: Kenichiro Itami, Nagoya (JP); Yasutomo Segawa, Nagoya (JP); Haruka Omachi, Nagoya (JP); Sanae Matsuura, Nagoya (JP); Yusuke Nakanishi, Nagoya (JP); Yuuki Ishii, Nagoya (JP)

(73) Assignee: National University Corporation Nagoya University, Nagoya-shi (JP)

(*) Notice: Subject to any disclaimer, the term of this patent is extended or adjusted under 35 U.S.C. 154(b) by 0 days.

(21) Appl. No.: 14/383,689

(22) PCT Filed: Mar. 7, 2013

(86) PCT No.: PCT/JP2013/056353
§ 371 (c)(1),
(2) Date: Dec. 5, 2014

(87) PCT Pub. No.: WO2013/133386
PCT Pub. Date: Sep. 12, 2013

(65) Prior Publication Data
US 2015/0126779 A1 May 7, 2015

(30) Foreign Application Priority Data
Mar. 8, 2012 (JP) .................. 2012-052318

(51) Int. Cl.
| | |
|---|---|
| *C07F 5/02* | (2006.01) |
| *C07C 43/21* | (2006.01) |
| *C07C 15/14* | (2006.01) |
| *C07C 25/18* | (2006.01) |
| *C07C 41/30* | (2006.01) |
| *C07C 41/09* | (2006.01) |
| *C07C 43/205* | (2006.01) |
| *C07C 35/21* | (2006.01) |
| *C07C 43/192* | (2006.01) |
| *C07C 17/361* | (2006.01) |
| *C07C 1/22* | (2006.01) |
| *C07C 17/35* | (2006.01) |
| *C07C 29/38* | (2006.01) |
| *C07C 1/20* | (2006.01) |

(52) U.S. Cl.
CPC . *C07F 5/025* (2013.01); *C07C 1/20* (2013.01); *C07C 1/22* (2013.01); *C07C 15/14* (2013.01); *C07C 17/35* (2013.01); *C07C 17/361* (2013.01); *C07C 25/18* (2013.01); *C07C 29/38* (2013.01); *C07C 35/21* (2013.01); *C07C 41/09* (2013.01); *C07C 41/30* (2013.01); *C07C 43/192* (2013.01); *C07C 43/205* (2013.01); *C07C 43/21* (2013.01); *C07C 2101/14* (2013.01); *C07C 2103/90* (2013.01)

(58) Field of Classification Search
None
See application file for complete search history.

(56) References Cited

U.S. PATENT DOCUMENTS

| | | | |
|---|---|---|---|
| 2011/0166390 | A1 | 7/2011 | Jasti et al. |
| 2012/0220790 | A1 | 8/2012 | Yamago |
| 2013/0041155 | A1 | 2/2013 | Itami et al. |
| 2013/0324768 | A1 | 12/2013 | Itami et al. |
| 2014/0030183 | A1 | 1/2014 | Itami et al. |
| 2014/0308195 | A1* | 10/2014 | Jasti et al. ................. 423/447.2 |

FOREIGN PATENT DOCUMENTS

| | | | |
|---|---|---|---|
| WO | WO-2011/040434 | A1 | 4/2011 |
| WO | WO-2011/099588 | A1 | 8/2011 |
| WO | WO-2011/111719 | A1 | 9/2011 |
| WO | WO-2012/121354 | A1 | 9/2012 |

OTHER PUBLICATIONS

Omachi, H. et al., "Synthesis and racemization process of chiral carbon nanorings: a step toward the chemical synthesis of chiral carbon nanotubes," Organic Letters, vol. 13, No. 9, 2011, pp. 2480-2483.

Omachi, H. et al., "A modular and Size-selective synthesis of [n]cycloparaphenylenes: a step toward the selective synthesis of [n,n]single-walled carbon nanotubes," Angewandte Chem. International Edition, 49, 2010, pp. 10202-10205.

(Continued)

*Primary Examiner* — Brian J Davis
(74) *Attorney, Agent, or Firm* — Locke Lord LLP; James E. Armstrong, IV; Nicholas J. DiCeglie, Jr.

(57) ABSTRACT

This invention selectively synthesizes a cycloparaphenylene compound having 10, 11, or 13 benzene rings. The invention also synthesizes a cycloparaphenylene compound in which a functional group is introduced into a desired portion. By reacting specific raw materials using a specific reaction, a cyclic compound having 10, 11, or 13 bivalent aromatic hydrocarbon groups, bivalent heterocyclic groups, or derivative groups thereof can be selectively obtained as a pure substance. Further, by a method comprising the step of reacting a specific organic compound containing no functional group with a specific organic compound containing a functional group, it is possible to obtain a cyclic compound containing a functional group in which one or more bivalent aromatic hydrocarbon groups, bivalent heterocyclic groups, or derivative groups thereof of a compound having 10 or more bivalent aromatic hydrocarbon groups, bivalent heterocyclic groups, or derivative groups thereof is substituted with a substituted 1,4-phenylene group.

20 Claims, No Drawings

(56) References Cited

OTHER PUBLICATIONS

Ishii, Y. et al., "Size-selective synthesis of [9]-[11] and[13]cycloparaphenylenes," Chemical Science vol. 3, 2012, pp. 2340-2345.

Takaba, H. et al., "Selective Synthesis of [12] Cycloparaphenylene,"Angewandte Chem. International Edition, 2009, vol. 48, pp. 6112-6116.

International Search Report dated May 21, 2013, issued for PCT/JP2013/056353.

* cited by examiner

CYCLIC COMPOUND CONTAINING FUNCTIONAL GROUP OR CONTAINING NO FUNCTIONAL GROUP, AND METHOD FOR PRODUCING SAME

TECHNICAL FIELD

The present invention relates to a cyclic compound containing a functional group or a cyclic compound containing no functional group, and production methods thereof.

BACKGROUND ART

Hitherto-known nanostructures containing carbon atoms include carbon nanotubes made of a cylindrically rolled two-dimensional graphene sheet, and cyclic carbon nanotubes made of such carbon nanotubes.

Carbon nanotubes have extremely high mechanical strength and high temperature resistance, and efficiently discharge electrons under voltage application. With these advantageous properties, carbon nanotubes are expected to be applied to various fields, including chemistry, electronics, and life science.

Known methods of manufacturing carbon nanotubes include arc discharge, laser furnaces, chemical vapor deposition, and the like. However, these methods have a disadvantage in that they can only produce mixtures of carbon nanotubes with various diameters and lengths.

As a replacement for tubular nanostructures such as carbon nanotubes having a certain length derived from a continuous linkage of carbon atoms, recent studies have focused attention on cyclic nanostructures. For example, cycloparaphenylene (CPP) is a simple and beautiful molecule in which benzenes are linked at the para-positions to form a circle. Recent studies have revealed that cycloparaphenylene has a significantly distinctive structure and nature. In particular, since CPP has various diameters depending on the number of benzene rings contained therein, and thereby has various natures, if CPP is selectively produced, it has the potential to produce carbon nanotubes having various diameters. Therefore, the thoroughly selective production of CPP having different numbers of benzene rings has been desired. However, although a method for obtaining CPP as a mixture is known, the selective synthesis of CPP was successful in only a few cases.

The present inventors succeeded in the synthesis of various cycloparaphenylene compounds through a method using a cyclic cycloparaphenylene precursor that contains a cyclohexane ring as a flexural portion (Patent Documents 1 and 2, Non-Patent Document

CITATION LIST

Patent Documents

Patent Document 1: Pamphlet of International Publication No. 2011/099588
Patent Document 2: Pamphlet of International Publication No.

Non-Patent Document

Non-Patent Document 1: Takaba, H.; Omachi, H.; Yamamoto, Y.; Bouffard, J.; Itami, K., Angew. Chem. Int. Ed. 2009, 48, 6112

SUMMARY OF INVENTION

Technical Problem

However, the cycloparaphenylene compound synthesized by the above method contains 9, 12, 14, or more benzene rings, and a method for synthesizing a cycloparaphenylene compound having 10, 11, or 13 benzene rings has been unknown. Further, even if these compounds are produced by accident, the yield will be very low, and they will only be obtained as a mixture. Thus, the selective synthesis of cycloparaphenylene compounds having these numbers of benzene rings has not been successful.

Further, as described above, although cycloparaphenylene compounds have a significantly distinctive structure and nature, the introduction of a new function by adding a functional group thereto has not been attempted. Since highly symmetrical molecules such as CPP have many equivalent reaction sites (for example, [12]CPP, which has 12 benzene rings, has 48 equivalent reaction sites), it is difficult to introduce a desired number of functional groups at desired positions.

In view of such problems, an object of the present invention is to selectively synthesize a cycloparaphenylene compound having 10, 11, or 13 benzene rings, which has never been synthesized. Another object of the present invention is to synthesize a cycloparaphenylene compound having a functional group at a desired portion, which has also never been successful.

Solution to Problem

The inventors of the present invention conducted extensive research to solve the above problems, and found that a cycloparaphenylene compound having 10, 11, or 13 benzene rings, which has never been successfully synthesized, can be selectively synthesized, not as a mixture, but as a pure substance, by using combinations of various raw materials and various reactions. Further, the inventors also found that by a method of first introducing a functional group into a raw material, and carrying out the synthesis while preventing the functional group from reacting, it is possible to synthesize a cycloparaphenylene compound having a functional group at a desired position. The inventors conducted further research based on such findings, and completed the present invention. Specifically, the present invention encompasses the cyclic compounds and production methods thereof, as well as a compound suitable as a raw material of the cyclic compound and the production method thereof, as defined in Items 1 to 16 below.

Item 1. A cyclic compound containing a functional group, wherein one or more bivalent aromatic hydrocarbon groups, bivalent heterocyclic groups, or derivative groups thereof of a cyclic compound having 10 or more bivalent aromatic hydrocarbon groups, bivalent heterocyclic groups, or derivative groups thereof are substituted with a group represented by General Formula (2):

[Chem. 1]

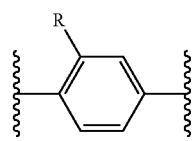

wherein R is a substituent.

Item 2. The cyclic compound containing a functional group according to Item 1, wherein the cyclic compound has 1 group represented by General Formula (2), and 9 or more bivalent aromatic hydrocarbon groups, bivalent heterocyclic groups, or derivative groups thereof.

Item 3. The cyclic compound containing a functional group according to Item 1 or 2, wherein R is a halogen atom.

Item 4. A method for producing the cyclic compound containing a functional group according to any one of Items 1 to 3, comprising the step of converting cyclohexane rings of a cyclic compound, which has one or more groups represented by General Formula (2);

3 to 4 groups represented by General Formula (1):

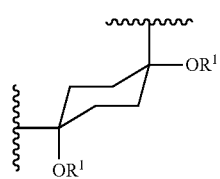

[Chem. 2]

wherein $R^1$ is the same or different, and each represents a hydrogen atom or a protecting group for a hydroxy group; and 6 or more bivalent aromatic hydrocarbon groups, bivalent heterocyclic groups, or derivative groups thereof, into benzene rings.

Item 5. The method according to Item 4, further comprising the step of reacting a compound containing no functional group with a compound containing a functional group to obtain the cyclic compound, wherein the compound containing no functional group is a compound obtained by reacting one kind of compound or two or more kinds of compounds selected from the group consisting of a compound represented by General Formula (I):

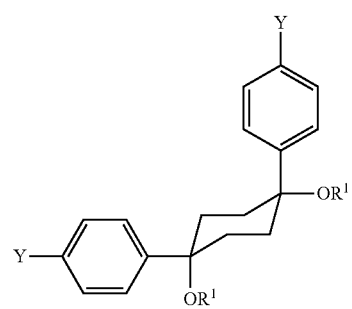

[Chem. 3]

wherein $R^1$ is as defined above; Y is the same or different, and each represents a halogen atom, or a boronic acid or an ester thereof; and a compound represented by General Formula (II):

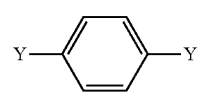

[Chem. 4]

wherein Y is as defined above, the compound containing a functional group is a compound represented by General Formula (III):

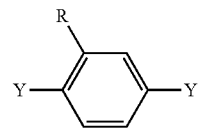

[Chem. 5]

wherein R and Y are as defined above, or a compound obtained by reacting the compound represented by General Formula (III) with one or more compounds containing no functional group.

Item 6. The method according to Item 5, wherein the compound containing no functional group is a compound represented by General Formula (VII-1):

Y—$R^2$—Y wherein $R^2$ is a bivalent group containing 1 to 3 structural units represented by General Formula (1) and 2 or more bivalent aromatic hydrocarbon groups, bivalent heterocyclic groups, or derivative groups thereof; and Y is as defined above, and the compound containing a functional group is a compound represented by General Formula (VII-2):

Y—$R^3$—Y wherein $R^3$ is a bivalent group containing one or more structural units represented by General Formula (2), 0 to 2 structural units represented by General Formula (1), and 0 or more bivalent aromatic hydrocarbon groups, bivalent heterocyclic groups, or derivative groups thereof; and Y is as defined above.

Item 7. A cyclic compound having one or more groups represented by General Formula (2):

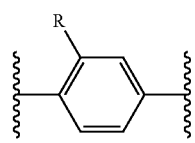

[Chem. 6]

wherein R is a substituent;
3 to 4 groups represented by General Formula (1):

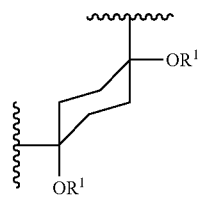

[Chem. 7]

wherein $R^1$ is the same or different, and each represents a hydrogen atom or a protecting group for a hydroxy group; and 6 or more bivalent aromatic hydrocarbon groups, bivalent heterocyclic groups, or derivative groups thereof.

Item 8. A method for producing the cyclic compound of Item 7, comprising the step of reacting a compound containing no functional group with a compound containing a functional group to obtain the cyclic compound, wherein the compound containing no functional group is obtained by reacting one kind of compound or two or more kinds of compounds selected from a compound represented by General Formula (I):

[Chem. 8]

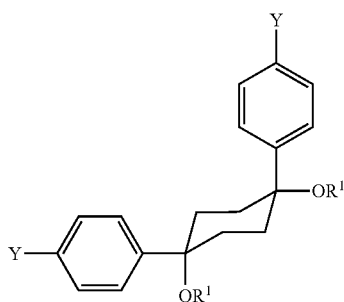

wherein $R^1$ is as defined above; Y is the same or different, and each represents a halogen atom, or a boronic acid or an ester thereof; and
a compound represented by General Formula (II):

[Chem. 9]

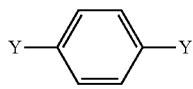

wherein Y is as defined above,
and the compound containing a functional group is a compound represented by General Formula (III):

[Chem. 10]

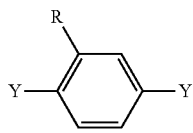

wherein R and Y are as defined above, or a compound obtained by reacting the compound represented by General Formula (III) with one or more of the compound containing no functional group.

Item 9. The method according to Item 8, wherein the compound containing no functional group is a compound represented by General Formula (VII-1):

Y—$R^2$—Y wherein $R^2$ is a bivalent group having 1 to 3 structural units represented by General Formula (1), and 2 or more bivalent aromatic hydrocarbon groups, bivalent heterocyclic groups, or derivative groups thereof; and Y is as defined above, and the compound containing a functional group is a compound represented by General Formula (VII-2):

Y—$R^3$—Y wherein $R^3$ is a bivalent group having one or more structural units represented by General Formula (2), 0 to 2 structural units represented by General Formula (1), and 0 or more bivalent aromatic hydrocarbon groups, bivalent heterocyclic groups, or derivative groups thereof; and Y is as defined above.

Item 10. A method for producing a cyclic compound having 9 to 13 bivalent aromatic hydrocarbon groups, bivalent heterocyclic groups, or derivative groups thereof, the method comprising the step of obtaining the cyclic compound by reacting, through an intramolecular ring closure reaction, terminal atoms of a chain compound represented by General Formula (IV):

X—$R^4$—X wherein $R^4$ is a bivalent group having 3 to 4 structural units represented by General Formula (1):

[Chem. 11]

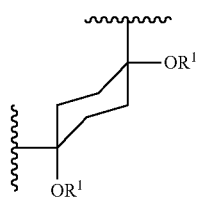

(wherein $R^1$ is the same or different, and each represents a hydrogen atom or a protecting group for a hydroxy group) and 6 or more bivalent aromatic hydrocarbon groups, bivalent heterocyclic groups, or derivative groups thereof; and X is the same or different, and each represents a halogen atom.

Item 11. A method for producing a cyclic compound having 10 to 13 bivalent aromatic hydrocarbon groups, bivalent heterocyclic groups, or derivative groups thereof, the method comprising the step of obtaining the cyclic compound by reacting a compound represented by General Formula (V-1):

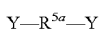
Y—$R^{5a}$—Y wherein $R^{5a}$ is a bivalent group having 3 structural units represented by General Formula (1) and 6 or more bivalent aromatic hydrocarbon groups, bivalent heterocyclic groups, or derivative groups thereof; and Y is the same or different, and each represents a halogen atom, or a boronic acid or an ester thereof,
with a compound represented by General Formula (V-2):

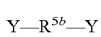
Y—$R^{5b}$—Y wherein $R^{5b}$ is a bivalent group having one or more bivalent aromatic hydrocarbon groups, bivalent heterocyclic groups, or derivative groups thereof; and Y is as defined above.

Item 12. A method for producing a cyclic compound having 9 to 13 bivalent aromatic hydrocarbon groups, bivalent heterocyclic groups, or derivative groups thereof, the method comprising the step of obtaining the cyclic compound by reacting a compound represented by General Formula (VI-1):

Y—$R^{6a}$—Y wherein $R^{6a}$ is a bivalent group having 2 structural units represented by General Formula (1) and 4 or more bivalent aromatic hydrocarbon groups, bivalent heterocyclic groups, or derivative groups thereof; and Y is the same or different, and each represents a halogen atom, or a boronic acid or an ester thereof,
with a compound represented by General Formula (VI-2):

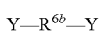
Y—$R^{6b}$—Y wherein $R^{6b}$ is a bivalent group having 1 structural unit represented by General Formula (1) and 2 or more bivalent aromatic hydrocarbon groups, bivalent heterocyclic groups, or derivative groups thereof; and Y is as defined above.

Item 13. A cyclic compound having 3 to 4 structural units represented by General Formula (1):

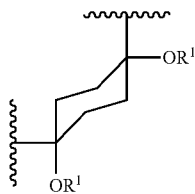

[Chem. 12]

wherein $R^1$ is the same or different, and each represents a hydrogen atom or a protecting group for a hydroxy group, and 6 to 9 bivalent aromatic hydrocarbon groups, bivalent heterocyclic groups, or derivative groups thereof, the cyclic compound having 10, 11, or 13 structural units represented by General Formula (1) and bivalent aromatic hydrocarbon groups, bivalent heterocyclic groups, or derivative groups thereof in total.

Item 14. A method for producing the cyclic compound of Item 13, comprising the step of reacting, through an intramolecular ring closure reaction, terminal atoms of a chain compound represented by General Formula (IV):

X—R⁴—X wherein $R^4$ is a bivalent group having 3 to 4 structural units represented by General Formula (1):

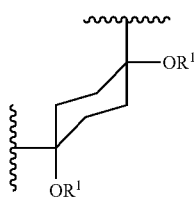

[Chem. 13]

(wherein $R^1$ is as defined above),
and 6 or more bivalent aromatic hydrocarbon groups, bivalent heterocyclic groups, or derivative groups thereof; and X is the same or different, and each represents a halogen atom.

Item 15. A method for producing the cyclic compound of Item 13, comprising the step of obtaining the cyclic compound by reacting a compound represented by General Formula (V-1):

Y—R⁵ᵃ—Y wherein $R^{5a}$ is a bivalent group having 3 structural units represented by General Formula (1) and 6 or more bivalent aromatic hydrocarbon groups, bivalent heterocyclic groups, or derivative groups thereof; and Y is the same or different, and each represents a halogen atom, or a boronic acid or an ester thereof,
with a compound represented by General Formula (V-2):

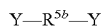
Y—R⁵ᵇ—Y wherein $R^{5b}$ is a bivalent group having one or more bivalent aromatic hydrocarbon groups, bivalent heterocyclic groups, or derivative groups thereof; and Y is as defined above.

Item 16. A method for producing the cyclic compound of Item 13, comprising the step of obtaining the cyclic compound by reacting a compound represented by General Formula (VI-1):

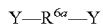
Y—R⁶ᵃ—Y wherein $R^{6a}$ is a bivalent group having 2 structural units represented by General Formula (1) and 4 or more bivalent aromatic hydrocarbon groups, bivalent heterocyclic groups, or derivative groups thereof; and Y is the same or different, and each represents a halogen atom, or a boronic acid or an ester thereof,
with a compound represented by General Formula (VI-2):

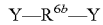
Y—R⁶ᵇ—Y wherein $R^{6b}$ is a bivalent group having 1 structural unit represented by General Formula (1) and 2 or more bivalent aromatic hydrocarbon groups, bivalent heterocyclic groups, or derivative groups thereof; and Y is as defined above.

Advantageous Effects of Invention

The present invention enables selective synthesis of a cyclic compound (in particular, cycloparaphenylene compound) having a desired number not less than 9 of bivalent aromatic hydrocarbon groups, bivalent heterocyclic groups, or derivative groups thereof (in particular 1,4-phenylene groups) as a pure substance. The obtained cyclic compounds having varying numbers of the groups and thus having different diameters can be suitably used for various electronic industry materials, luminescence materials, and the like.

The present invention thus enables selective synthesis of cyclic compounds having varying numbers of bivalent aromatic hydrocarbon groups, bivalent heterocyclic groups, or derivative groups thereof (in particular 1,4-phenylene group) as a pure substance. The cyclic compounds are useful as a raw material for the synthesis of carbon nanotubes having various diameters depending on the number of bivalent aromatic hydrocarbon groups, bivalent heterocyclic groups, or derivative groups thereof (in particular 1,4-phenylene group).

Further, the present invention enables introduction of a desired number of functional groups into desired portions of a cyclic compound that is highly symmetrical and has many equivalent reaction sites, such as a cycloparaphenylene compound.

Description of Embodiments

[1] Cyclic Compound

The cyclic compound of the present invention is a cyclic compound that contains no functional group and has 10, 11, or 13 bivalent aromatic hydrocarbon groups, bivalent heterocyclic groups, or derivative groups thereof.

More specifically, the compound is a cyclic compound represented by General Formula (A):

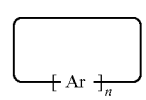

[Chem. 14]

wherein Ar is the same or different, and represents a bivalent aromatic hydrocarbon group, a bivalent heterocyclic group, or a derivative group thereof; and n is 10, 11, or 13.

Ar represents a bivalent aromatic hydrocarbon group, a bivalent heterocyclic group, or a derivative group thereof. In other words, Ar is a bivalent group having an organic ring selected from aromatic groups and heterocyclic groups (hereinafter, this bivalent group may be referred to as a "bivalent organic ring group") in which a hydrogen atom is eliminated from two carbon atoms of the organic ring. Ar may be the same or different.

In addition to benzene rings, examples of the aromatic rings also include rings resulting from the condensation of multiple benzene rings (benzene condensed rings), and rings resulting from the condensation of benzene and other rings (hereinafter, these rings resulting from the condensation of multiple benzene rings, and rings resulting from the condensation of benzene and other rings may be collectively referred to as "condensed rings"). Examples of the condensed rings include a pentalene ring, indene ring, naphthalene ring, anthracene ring, tetracene ring, pentacene ring, pyrene ring, perylene ring, triphenylene ring, azulene ring, heptalene ring, biphenylene ring, indacene ring, acenaphthylene ring, fluorene ring, phenalene ring, and phenanthrene ring.

Examples of the heterocyclic rings include heterocyclic rings (namely, heterocyclic aromatic rings and heterocyclic aliphatic rings, in particular, heterocyclic aromatic rings) having at least one atom selected from a nitrogen atom, oxygen atom, boron atom, phosphorus atom, silicon atom and sulfur atom. Examples of heterocyclic rings include a furan ring, thiophene ring, pyrrole ring, silole ring, borole ring, phosphole ring, oxazole ring, thiazole ring, pyridine ring, pyridazine ring, pyrimidine ring, and pyrazine ring. Heterocyclic condensed rings obtained by combining these rings, these rings and benzene rings, or these rings and the aforementioned condensed rings (such as thienothiophene rings or quinoline rings) may also be used.

Among these rings, Ar is preferably a group that contains a bivalent 6-membered aromatic ring or a bivalent 6-membered heterocyclic aromatic ring, and has binding sites at the para-positions.

Further, the organic ring of Ar is preferably a monocyclic or condensed ring. A monocyclic ring is more preferable.

Among these, Ar is preferably a phenylene group (in particular, a 1,4-phenylene group) and a naphthylene group (in particular, a 1,5-naphthylene group or 2,6-naphthylene group). A phenylene group (in particular, a 1,4-phenylene group) is more preferable. In the cyclic compound of the present invention, n, i.e., the number of the bivalent organic ring groups, is 10, 11, or 13.

As described above, for a cyclic compound, for example, for a cycloparaphenylene compound having 1,4-phenylene groups, a cycloparaphenylene compound having 9, 12, 14, or more 1,4-phenylene groups can be obtained by a known method (Patent Documents 1 and 2, and Non-Patent Document 1).

The present invention enables synthesis of a cyclic compound having 9, 12, 14, or more bivalent aromatic hydrocarbon groups, and also enables selective synthesis of a cyclic compound having 10, 11, or 13 bivalent organic ring groups as a pure substance, which has heretofore been unsuccessful. More specifically, the cyclic compound of the present invention is a novel compound that is not disclosed in any documents (i.e., there are no documents that disclose selective production of such a cyclic compound as a pure substance).

Further, the diameter of the cyclic compound of the present invention is about 1.39 nm when the cyclic compound has 10 bivalent organic ring groups (in particular, 1,4-phenylene groups). Additionally, the diameter is about 1.51 nm when the cyclic compound has 11 bivalent organic ring groups, and is about 1.79 nm when the cyclic compound has 13 bivalent organic ring groups.

Furthermore, the cyclic compound of the present invention is preferably a cycloparaphenylene compound in which all of the organic ring groups are phenylene groups (in particular, 1,4-phenylene groups).

Further, among the cyclic compounds of the present invention, for example, a cycloparaphenylene compound having 10, 11, or 13 1,4-phenylene groups is represented by General Formula (A1) below:

[Chem. 15]

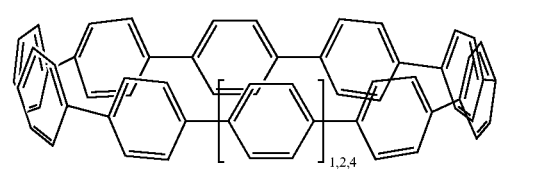

The compound of the present invention is useful as a raw material for synthesizing (pure synthesis) a carbon nanotube having a uniform radius, and is also suitable for electronic industry materials, luminescence materials, and the like. Such an effect is particularly significant in a compound in which all of the bivalent organic ring groups are 1,4-phenylene groups, as in the cycloparaphenylene compound represented by General Formula (A1).

[2] Method for producing cyclic compound

Raw Material

In the present invention, a cyclic compound obtained by reacting one kind of compound, or two or more kinds of compounds selected from the group consisting of a compound represented by General Formula (I):

[Chem. 16]

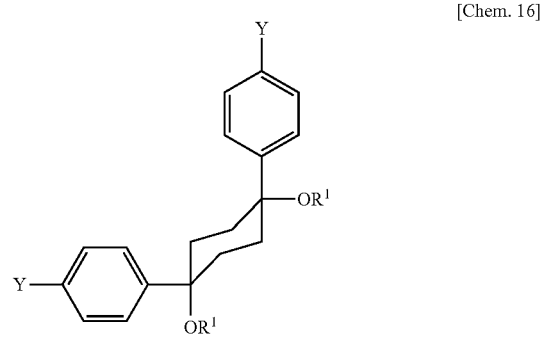

wherein $R^1$ is the same or different, and each represents a hydrogen atom or a protecting group for a hydroxy group; and Y is the same or different, and each represents a halogen atom, or a boronic acid or an ester thereof, and a compound represented by General Formula (II):

[Chem. 17]

wherein Y is as defined above,
is used as a raw material.

More preferably, in the method for producing the cyclic compound of the present invention, the cyclic compound is obtained by using a compound obtained by reacting one kind of compound, or two or more kinds of compounds selected from the group consisting of a compound represented by General Formula (Ia):

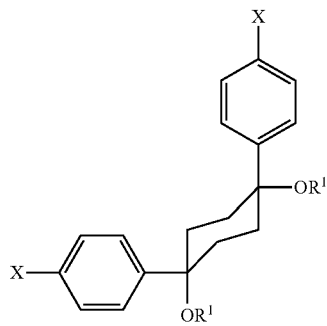

[Chem. 18]

wherein $R^1$ is as defined above; and X is the same or different, and each represents a halogen atom; a compound represented by General Formula (Ib):

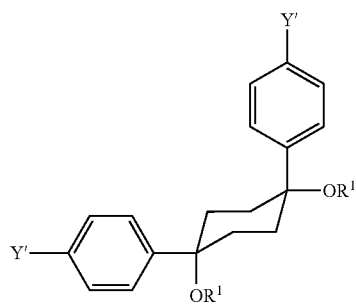

[Chem. 19]

wherein $R^1$ is as defined above; and Y' is the same or different, and each represents a boronic acid or an ester thereof;
a compound represented by General Formula (IIa):

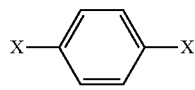

[Chem. 20]

wherein X is as defined above;
and
a compound represented by General Formula (IIb):

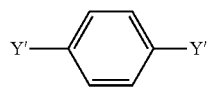

[Chem. 21]

wherein Y' is as defined above.

The cyclic compound of the present invention is obtained by combining various compounds in many different ways, and using various reactions for producing a cyclic compound.

The benzene ring that constitutes a phenylene group generally has a rigid, planar structure. On the other hand, the cyclohexane ring of the compound represented by General Formula (1) is attached to the benzene ring at the 1-position and 4-position, forming a nonlinear (L-shaped) structure of chair conformation in which the benzene rings are respectively at axial and equatorial positions. Accordingly, the cplaompound represented by General Formula (I) has a nonplanar or nonlinear structure, which differs from a linear structure.

Further, in addition to those having a chair conformation, there are cyclohexane rings having a nonplanar structure such as a boat conformation, a twist-boat conformation, or the like. Therefore, by suitably selecting a variety of organic ring groups, it becomes possible to obtain compounds of various structures.

For example, since the compound represented by General Formula (I) has only one cyclohexylene derivative group having a chair conformation, the compound represented by General Formula (I) has a structure in which the cyclohexylene ring is bonded to the benzene rings at the 1-position and 4-position, forming an L-shaped structure in which the benzene rings are at axial and equatorial positions. Further, in this L-shaped structure, the acute angle (hereinafter, "inner angle") of the flexural portion of the cyclohexylene derivative group is substantially 90°. Further, when the compound has two cyclohexane rings having a chair conformation as organic ring groups as in the later-described compound represented by General Formula (5), the compound has a U-shaped structure in which each inner angle is about 90°. Additionally, when the compound has three cyclohexane rings having a chair conformation as organic ring groups as in the later-described compound represented by General Formula (3), the compound has a C-shaped structure in which each inner angle is about 90°.

$R^1$ represents a hydrogen atom or a protecting group for a hydroxy group.

The protecting group for hydroxy group is not particularly limited. Examples thereof include an alkoxy alkyl group (e.g., a methoxymethyl group ($-CH_2-O-CH_3$, which may be referred to as "-MOM" hereinafter), etc.), alkanoyl group (e.g., an acetyl group, propionyl group, etc.), a silyl group (e.g., a trimethylsilyl group, triethylsilyl group, t-butyldimethylsilyl group, etc.), a tetrahydropyranyl group (THP), an alkyl group (e.g., methyl group, ethyl group, t-butyl group, etc.), and a benzyl group. An alkoxy alkyl group, in particular, a methoxymethyl group, is preferable.

The protecting group (preferably an alkoxy alkyl group, in particular, a methoxymethyl group) is substituted with a hydrogen atom of alcohol (hydroxy group), thereby serving as a protecting group for the alcohol.

Further, among the protecting groups, methoxymethyl group is obtained, for example, by reacting chloromethylmethylether ($Cl-CH_2-O-CH_3$) with the alcohol to be protected.

$R^1$ may be the same or different. In the cyclic compound of the present invention, each $R^1$ is preferably an alkoxy alkyl group, in particular, a methoxymethyl group ($-CH_2-O-CH_3$).

The halogen atom (represented by X or Y) is not particularly limited. Examples thereof include a fluorine atom, chlorine atom, bromine atom, and iodine atom. In the present invention, a bromine atom and an iodine atom are preferable, and a bromine atom is particularly preferable. Further, X and Y (when Y is a halogen atom) may be the same or different.

The boronic acid or an ester thereof (represented by Y or Y') is preferably a group represented by the formula below,

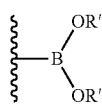

wherein R' is the same or different, and each represents a hydrogen atom or lower alkyl group (in particular, C1-10 alkyl group); and R' may be bonded to form a ring with adjacent —O—B—O—.

The boronic acid or an ester thereof (represented by X or Y) may be the same or different.

R' in the boronic acid or an ester thereof is a hydrogen atom or an alkyl group. The alkyl group preferably has 1 to 10, more preferably 1 to 8, and further preferably 1 to 5 carbon atoms. Further, the two R' may be the same or different. When R' is an alkyl group, the carbon atoms of the alkyl group may be bonded to form a ring with the boron atoms and the oxygen atoms.

Examples of such a boronic acid or an ester thereof include a group represented by the formula below,

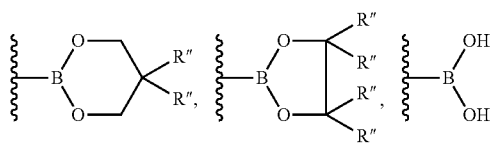

wherein R" is the same or different, and each represents a hydrogen atom or lower alkyl group (in particular, C1-10 alkyl group). By using such a group, the cyclic compound of the present invention can be more efficiently obtained.

Among the above compounds, the compound represented by General Formula (Ia) is obtained, for example, by reacting 1,4-cyclohexanedione represented by the formula below,

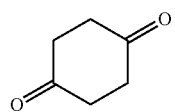

and the compound (which may also be referred to as an "aromatic dihalogen compound" hereinafter) represented by the formula below,

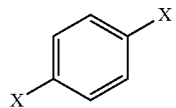

wherein X is as defined above.

The aromatic dihalogen compound is not particularly limited insofar as it has halogen atoms at the 1-position and 4-position. Examples of such compounds include 1,4-dibromobenzene, 1,4-diiodobenzene, and 1-bromo-4-iodobenzene.

The amount of the aromatic dihalogen compound is preferably 2.0 to 10 mol, more preferably 2.3 to 5.0 mol, per mol of 1,4-cyclohexanedione.

The production method using the raw materials above is not particularly limited. More specifically, the following method can be adopted. The aromatic dihalogen compound is reacted with an organic alkali metal compound to cause an interchange reaction of an alkali metal atom with a halogen atom, thereby obtaining a precursor compound containing a halogen atom and a hydrocarbon group resulting from substitution of a halogen atom of the aromatic dihalogen compound with a hydrocarbon group of the organic alkali metal compound; then, the resulting precursor compound is reacted with 1,4-cyclohexanedione to cause a nucleophilic addition reaction. In this method, 1,4-dibromobenzene, 1,4-diiodobenzene, 1-bromo-4-iodobenzene, and the like, are preferably used as the aromatic dihalogen compound.

Further, examples of the organic alkali metal compounds include organic lithium compounds and organic sodium compounds. Organic lithium compounds are particularly preferable. Examples of organic lithium compounds include organic monolithium compounds, organic dilithium compounds, and organic polylithium compounds.

Examples of organic lithium compounds include ethyllithium, n-propyllithium, isopropyllithium, n-butyllithium, sec-butyllithium, tert-butyllithium, pentyllithium, hexyllithium, cyclohexyllithium, phenyllithium, hexamethylene dilithium, cyclopentadienyl lithium, indenyl lithium, 1,1-diphenyl-n-hexyllithium, 1,1-diphenyl-3-methylpentyllithium, lithium naphthalene, butadienyl dilithium, isopropenyl dilithium, m-diisoprenyl dilithium, 1,3-phenylene-bis-(3-methyl-1-phenylpentylidene)bislithium, 1,3-phenylene-bis-(3-methyl-1,[4-methylphenyl]pentylidene)bislithium, 1,3-phenylene-bis-(3-methyl-1,[4-dodecylphenyl] pentylidene) bislithium, 1,1,4,4-tetraphenyl-1,4-dilithio butane, polybutadienyl lithium, polyisoprenyl lithium, polystyrene-butadienyl lithium, polystyrenyl lithium, polyethylenyl lithium, poly-1,3-cyclohexa dienyl lithium, polystyrene 1,3-cyclohexadienyl lithium, and polybutadiene 1,3-cyclohexadienyl lithium. Among these, n-butyllithium is preferable.

The amount of the organic alkali metal compound is preferably 0.8 to 5 mol, more preferably 0.9 to 3.0 mol, per mol of the aromatic dihalogen compound.

As the raw materials to be used in the above method, it is preferable to use a combination of 1,4-dibromobenzene as the aromatic dihalogen compound, and n-butyllithium as the organic alkali metal compound. In this case, the reaction of 1,4-dibromobenzene with n-butyllithium (a lithium-bromo interchange reaction) produces 4-bromophenyllithium. Then, by causing a nucleophilic addition reaction of 4-bromophenyllithium and cyclohexane 1,4-dione, a compound represented by the formula below:

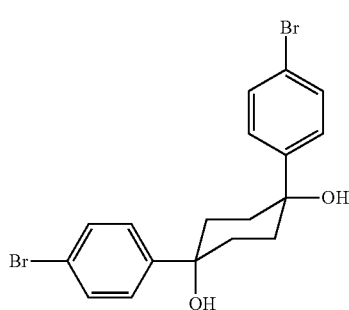

is obtained.

Further, in the above reaction, a metal chloride, such as lithium chloride, cerium chloride, or the like, may be used. For example, when 1,4-dibromobenzene is used as the aromatic dihalogen compound and n-butyllithium is used as the organic alkali metal compound, 4-bromophenyllithium may be reacted, undesirably, as a base (side reaction). This is a common side reaction of an organic lithium reaction agent such as n-butyllithium or the like. To avoid such a side reaction, it is possible to prepare a corresponding 4-bromophenyl cerium reaction agent (an organocerium reaction agent) from 4-bromophenyllithium and cerium chloride in the above reaction system. This organocerium reaction agent generally has low basicity, and thus is considered to suppress side reactions. Lithium chlorides can also be used, because lithium chlorides are considered to have an effect of increasing the solubility of, for example, a 4-bromophenylcerium reaction agent in organic solvents.

When a metal chloride, such as lithium chloride, cerium chloride, or the like, is used, the amount thereof is preferably 0.1 to 100 molar equivalents, and more preferably 0.5 to 20 molar equivalents, with respect to the aromatic dihalogen compound (in particular, 1,4-dibromobenzene).

Further, the above reaction of the aromatic dihalogen compound and the organic alkali metal compound is generally performed in the presence of a reaction solvent. Examples of reaction solvents include aromatic hydrocarbons such as toluene, xylene, or benzene; esters such as methyl acetate, ethyl acetate, or butyl acetate; cyclic ethers such as diethylether, tetrahydrofuran, dioxane, dimethoxyethane, or diisopropylether; halogenated hydrocarbons such as methyl chloride, chloroform, dichloromethane, dichloroethane, or dibromoethane; ketones such as acetone or methyl ethyl ketone; amides such as dimethylformamide or dimethylacetamide; nitriles such as acetonitrile; alcohols such as methanol, ethanol, or isopropyl alcohol; and dimethylsulfoxides. These substances can be used singly, or in a combination of two or more. Among them, cyclic ethers (such as tetrahydrofuran) are preferable in the present invention.

The reaction temperature in the above reaction of the aromatic dihalogen compound and the organic alkali metal compound is generally not less than 0° C., and is selected from a temperature range of not more than the boiling point of the reaction solvent.

Further, the reaction atmosphere in the above reaction step is not particularly limited; however, an inert gas atmosphere, such as an argon gas atmosphere, a nitrogen gas atmosphere, etc., is preferable. It is also possible to adopt an air atmosphere.

Additionally, a purification step may be performed after the reaction step as necessary. In this purification step, general post-treatment steps, such as solvent removal, washing, chromatography separation, or the like, may be performed.

Thereafter, the hydroxy group may be protected using a known method. As a result, the compound represented by General Formula (Ia) in which $R^1$ is a protecting group is obtained. Examples of the protecting group are the same as those listed above.

The compound represented by General Formula (Ib) is obtained by converting the halogen atom at each end of the compound represented by General Formula (Ia) into a boronic acid or an ester thereof, through, for example, a borylation reaction using a boron compound.

Examples of boron compounds used in the above reaction include 2-phenyl-1,3,2-dioxaborinane, (4,4,5,5)-tetramethyl-1,3,2-dioxaborolane, 4,4,4',4',5,5,5',5'-octamethyl-2,2'-bi[1,3,2-dioxaborolane](bispinacolatodiboron), 5,5,5',5'-tetramethyl-5,5',6,6'-tetrahydro-2,2'-bi[4H-1,3,2-dioxaborine], and 1,1,2,2-tetrahydroxy-1,2-diboraethane.

The amount of the boron compound is preferably 1 to 10 mol, more preferably 1.5 to 7 mol, per mol of the compound represented by General Formula (Ia).

The reaction is generally performed in the presence of a catalyst, preferably a palladium catalyst. Examples of palladium catalysts include palladium metal and various known palladium compounds to be used as a catalyst for synthesizing organic compounds (including polymer compounds), etc. In the present invention, the palladium catalysts (palladium compounds) usable in the Suzuki-Miyaura coupling reaction may be used. Specific examples thereof include $Pd(PPh_3)_4$ (Ph represents a phenyl group), $PdCl_2(PPh_3)_2$ (Ph represents a phenyl group), $Pd(OAc)_2$ (Ac represents an acetyl group), tris(dibenzylideneacetone)dipalladium(0)($Pd_2(dba)_3$), tris(dibenzylideneacetone)dipalladium(0)chloroform complex, bis(dibenzylideneacetone)palladium(0), bis(tri-t-butyl)phosphino)palladium(0), and (1,1'-bis(diphenylphosphino)ferrocene)dichloropalladium(II). In the present step, $Pd_2(dba)_3$, $Pd(PPh_3)_4$, and (1,1'-is(diphenylphosphino)ferrocene)dichloropalladium(II) are preferable.

When a palladium catalyst is used in this step, the amount is, in terms of the yield, generally 0.001 to 1 mol, preferably 0.005 to 0.1 mol, per mol of the compound represented by General Formula (Ia) used as the raw material.

Further, as required, it is possible to use, as a catalyst, a phosphorus ligand that can be coordinated with the palladium atom that is the center element of the palladium catalyst. Examples of phosphorus ligands include triphenylphosphine, tri-o-tolylphosphine, tri-m-tolylphosphine, tri-p-tolylphosphine, tris(2,6-dimethoxyphenyl)phosphine, tris[2-(diphenylphosphino)ethyl]phosphine, bis(2-methoxyphenyl)phenylphosphine, 2-(di-t-butylphosphino)biphenyl, 2-(dicyclohexylphosphino)biphenyl, 2-(diphenylphosphino)-2'-(N,N-dimethylamino)biphenyl, tri-t-butylphosphine, bis(diphenylphosphino)methane, 1,2-bis(diphenylphosphino)ethane, 1,2-bis(dimethylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(dimethylphosphino)ethane, 1,1'-bis(diphenylphosphino)ferrocene, bis(2-diphenylphosphinoethyl)phenylphosphine, 2-(dicyclohexylphosphino)-2',6'-dimethoxy-1,1'-biphenyl (S-Phos), 2-(dicyclohexylphosphino)-2',4',6'-tri-isopropyl-1,1'-biphenyl(X-Phos), and bis(2-diphenylphosphinophenyl)ether (DPEPhos). In the present step, 2-(dicyclohexylphosphino)-2',4',6'-tri-isopropyl-1,1'-biphenyl (X-Phos), and the like, are preferable.

When a phosphorus ligand is used, the amount is, in terms of the yield, generally 0.01 to 1.0 mol, preferably 0.05 to 0.5 mol, per mol of the compound represented by General Formula (Ia) used as the raw material.

Further, as required, a base (a reagent for activation of boron species) may be used in addition to the palladium catalyst. This base is not particularly limited insofar as it is a compound that can form an ate complex on the boron atom by the Suzuki-Miyaura coupling reaction. More specifically, examples of bases include potassium fluoride, cesium fluoride, sodium hydroxide, potassium hydroxide, sodium methoxide, sodium hydrogen carbonate, potassium hydrogen carbonate, sodium carbonate, potassium carbonate, cesium carbonate, silver carbonate, potassium phosphate, sodium acetate, potassium acetate, and calcium acetate. Among these, potassium acetate and the like are preferable. The amount of the base is generally about 0.1 to 5.0 mol, and preferably 0.5 to 1.0 mol, per mol of one of the compound represented by General Formula (Ia) and the compound represented by General Formula (Ib) in a smaller amount.

Further, the reaction is generally performed in the presence of a reaction solvent. Examples of reaction solvents include aromatic hydrocarbons such as toluene, xylene, or benzene; esters such as methyl acetate, ethyl acetate, or butyl acetate; cyclic ethers such as diethylether, tetrahydrofuran, dioxane, or dimethoxyethane, diisopropylether; halogenated hydrocarbons such as methyl chloride, chloroform, dichloromethane, dichloroethane, or dibromoethane; ketones such as acetone, or methyl ethyl ketone; amides such as dimethylformamide or dimethylacetamide; nitriles such as acetonitrile; alcohols such as methanol, ethanol, or isopropyl alcohol; and dimethylsulfoxides. These substances can be used singly, or in a combination of two or more. Among them, dimethylsulfoxides, etc., are preferable in the present invention.

The reaction temperature is generally not less than 0° C., and is selected from a temperature range of not more than the boiling point of the reaction solvent.

Further, the reaction atmosphere is not particularly limited; an inert gas atmosphere, such as an argon gas atmosphere, a nitrogen gas atmosphere, etc., is preferable. It is also possible to adopt an air atmosphere.

When the boron compound has a cyclic boronic acid ester group, it is possible to first produce the compound having the boronic acid ester group, and then convert the boronic acid ester group into a boronic acid group through hydrolysis.

Further, a known or commercially available compound may be used as the compound represented by General Formula (II).

Among the compounds used as a raw material, examples of the compound obtained by reacting two or more kinds selected from the compound represented by General Formula (I) and the compound represented by General Formula (II) include a compound represented by General Formula (3):

[Chem. 27]

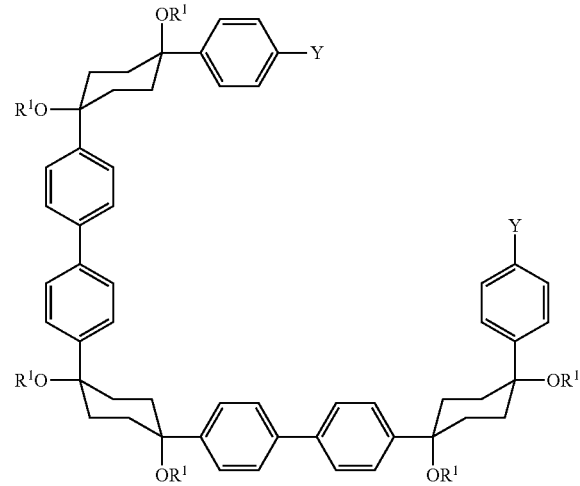

wherein $R^1$ and Y are as defined above;

a compound represented by General Formula (4):

[Chem. 28]

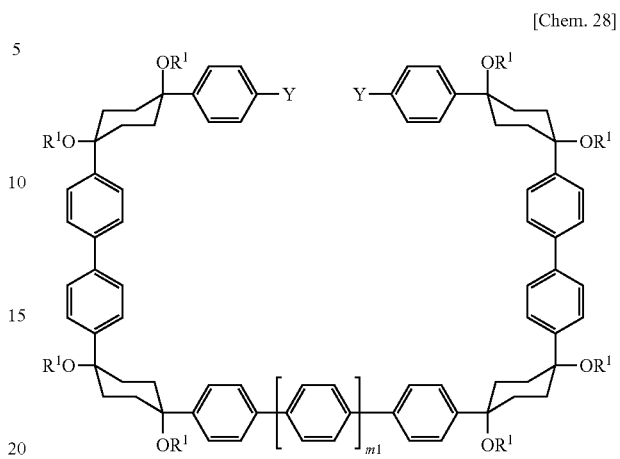

wherein $R^1$ and Y are as defined above; and m1 is an integer of 1 or more (in particular, 1);

a compound represented by General Formula (5):

[Chem. 29]

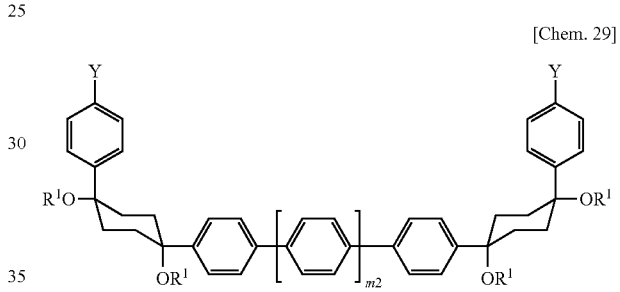

wherein $R^1$ and Y are as defined above; and m2 is an integer of 1 or more (preferably 1); and a compound represented by General Formula (6):

[Chem. 30]

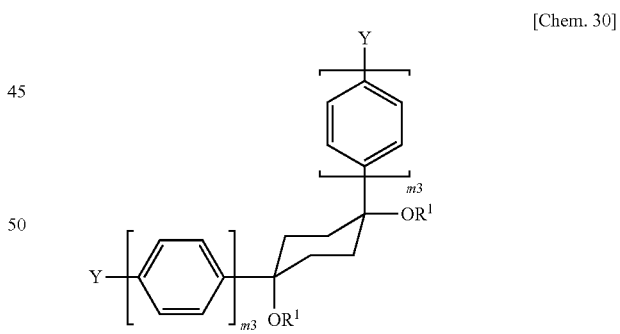

wherein $R^1$ and Y are as defined above; and m3 is the same or different, and each represents an integer of 2 or more (preferably 2).

Compound Represented by General Formula (3)

The compound represented by General Formula (3) can be obtained by, for example, a reaction using the compound represented by General Formula (I). More specifically, using the compound represented by General Formula (Ia) and the compound represented by General Formula (Ib), the compound represented by General Formula (3) can be obtained by reacting the halogen atom at an end of the compound represented by General Formula (Ia) with the boronic acid or an ester thereof at an end of the compound represented by General Formula (Ib), thereby obtaining a trimer.

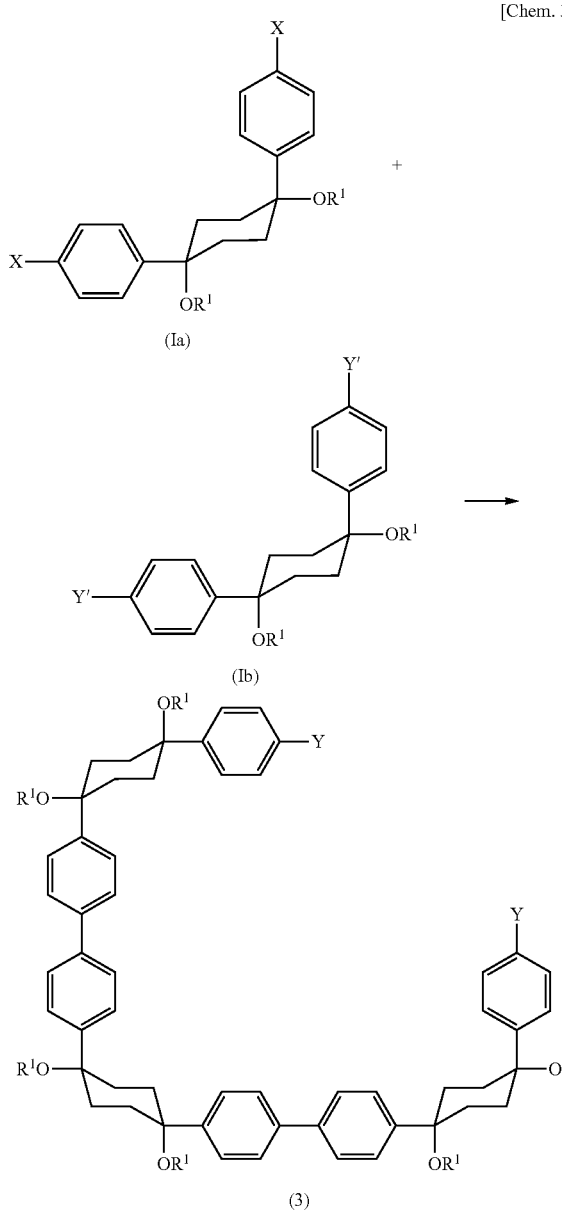

wherein $R^1$, X, Y, and Y' are as defined above.

This reaction produces the compound represented by General Formula (3) as a C-shaped chain compound using the flexural portions of the cyclohexane rings.

The above reaction of the compound represented by General Formula (Ia) and the compound represented by General Formula (Ib) is preferably performed using the Suzuki-Miyaura coupling reaction. The Suzuki-Miyaura coupling reaction is a carbon-carbon bond reaction, and causes a coupling reaction of an aryl halide compound and an organic boron compound. The compound represented by General Formula (Ia) is an aryl halide compound having a halogen atom, and the compound represented by General Formula (Ib) is an organic boron compound having a boronic acid (or esters thereof) group.

The amounts of the compound represented by General Formula (Ia) and the compound represented by General Formula (Ib) are preferably suitably adjusted according to the target compound represented by General Formula (3).

More specifically, it is preferable to use an excessive amount of the compound represented by General Formula (Ia) when the compound represented by General Formula (3) having halogen atoms at the two ends is produced. Specifically, the amount of the compound represented by General Formula (Ib) is preferably 0.05 to 0.2 mol, more preferably 0.075 to 0.15 mol, per mol of the compound represented by General Formula (Ia).

Further, it is preferable to use an excessive amount of the compound represented by General Formula (Ib) when the compound represented by General Formula (3) having boronic acids or esters thereof at the two ends is produced. Specifically, the amount of the compound represented by General Formula (Ib) is preferably 5 to 20 mol, more preferably 7 to 15 mol, per mol of the compound represented by General Formula (Ia).

The above reaction is generally performed in the presence of a catalyst, preferably a palladium catalyst. Examples of palladium catalysts include palladium metal and various known palladium compounds to be used as a catalyst for synthesizing organic compounds (including polymer compounds), etc. In the present invention, palladium catalysts (palladium compounds) usable in the Suzuki-Miyaura coupling reaction may be used. Specific examples thereof include $Pd(PPh_3)_4$ (Ph represents a phenyl group), $PdCl_2(PPh_3)_2$ (Ph represents a phenyl group), $Pd(OAc)_2$ (Ac represents an acetyl group), tris(dibenzylideneacetone)dipalladium(0)($Pd_2(dba)_3$), tris(dibenzylideneacetone)dipalladium(0)chloroform complex, bis(dibenzylideneacetone)palladium(0), bis(tri-t-butyl)phosphino)palladium(0), and (1,1'-bis(diphenylphosphino)ferrocene)dichloropalladium(II). In the present step, $Pd(PPh_3)_4$, $Pd_2(dba)_3$, etc., are preferable.

When a palladium catalyst is used, the amount is, in terms of the yield, generally 0.001 to 1 mol, preferably 0.005 to 0.5 mol, per mol of one of the compound represented by General Formula (Ia) and the compound represented by General Formula (Ib) in a smaller amount.

Further, as required, it is possible to use, as a catalyst, a phosphorus ligand that can be coordinated with the palladium atom that is the center element of the palladium catalyst. Examples of phosphorus ligands include triphenylphosphine, tri-o-tolylphosphine, tri-m-tolylphosphine, tri-p-tolylphosphine, tris(2,6-dimethoxyphenyl)phosphine, tris[2-(diphenylphosphino)ethyl]phosphine, bis(2-methoxyphenyl)phenylphosphine, 2-(di-t-butylphosphino)biphenyl, 2-(dicyclohexylphosphino)biphenyl, 2-(diphenylphosphino)-2'-(N,N-dimethylamino)biphenyl, tri-t-butylphosphine, bis(diphenylphosphino)methane, 1,2-bis(diphenylphosphino)ethane, 1,2-bis(dimethylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(dimethylphosphino)ethane, 1,1'-bis(diphenylphosphino)ferrocene, bis(2-diphenylphosphinoethyl)phenylphosphine, 2-(dicyclohexylphosphino-2',6'-dimethoxy-1,1'-biphenyl(S-Phos), 2-(dicyclohexylphosphino-2',4',6'-tri-isopropyl-1,1'-biphenyl (X-Phos), and bis(2-diphenylphosphinophenyl)ether (DPEPhos). In the present step, 2-(dicyclohexylphosphino)-2',4',6'-tri-isopropyl-1,1'-biphenyl(X-Phos), and the like are preferable.

When a phosphorus ligand is used, the amount is, in terms of the yield, generally 0.01 to 1.0 mol, preferably 0.05 to 0.5 mol, per mol of one of the compound represented by General Formula (Ia) and the compound represented by General Formula (Ib) in a smaller amount.

Further, as required, a base (a reagent for activation of boron species) may be used in addition to the palladium catalyst. This base is not particularly limited insofar as it is a compound that can form an ate complex on the boron atom by the Suzuki-Miyaura coupling reaction. More specifically, examples of bases include potassium fluoride, cesium fluoride, sodium hydroxide, potassium hydroxide, sodium methoxide, sodium hydrogen carbonate, potassium hydrogen carbonate, sodium carbonate, potassium carbonate, cesium carbonate, silver carbonate, potassium phosphate, sodium acetate, potassium acetate, and calcium acetate. Among these, cesium fluoride, cesium carbonate, silver carbonate, and potassium phosphate are preferable. The amount of the base is generally about 0.1 to 5.0 mol, and preferably 0.5 to 4.0 mol, per mol of one of the compound represented by General Formula (Ia) and the compound represented by General Formula (Ib) in a smaller amount.

Further, the reaction is generally performed in the presence of a reaction solvent. Examples of reaction solvents include aromatic hydrocarbons such as toluene, xylene, or benzene; esters such as methyl acetate, ethyl acetate, or butyl acetate; cyclic ethers such as diethylether, tetrahydrofuran, dioxane, or dimethoxyethane, diisopropylether; halogenated hydrocarbons such as methyl chloride, chloroform, dichloromethane, dichloroethane, or dibromoethane; ketones such as acetone, or methyl ethyl ketone; amides such as dimethylformamide or dimethylacetamide; nitriles such as acetonitrile; alcohols such as methanol, ethanol, or isopropyl alcohol; and dimethylsulfoxides. These substances can be used singly, or in a combination of two or more. Among them, cyclic ethers (such as tetrahydrofuran) are preferable in the present invention.

The reaction temperature is generally not less than 0° C., and is selected from a temperature range of not more than the boiling point of the reaction solvent.

Further, the reaction atmosphere is not particularly limited; an inert gas atmosphere, such as an argon gas atmosphere, a nitrogen gas atmosphere, etc., is preferable. It is also possible to adopt an air atmosphere.

Compound Represented by General Formula (5)

The compound represented by General Formula (5) is obtained, for example, by a reaction using the compound represented by General Formula (I) and the compound represented by General Formula (II). More specifically, the compound represented by General Formula (5) is obtained by reacting the halogen atom at an end of the compound represented by General Formula (Ia) or the compound represented by General Formula (IIa) with the boronic acid or an ester thereof at an end of the compound represented by General Formula (Ib) or the compound represented by General Formula (IIb).

[Chem. 32]

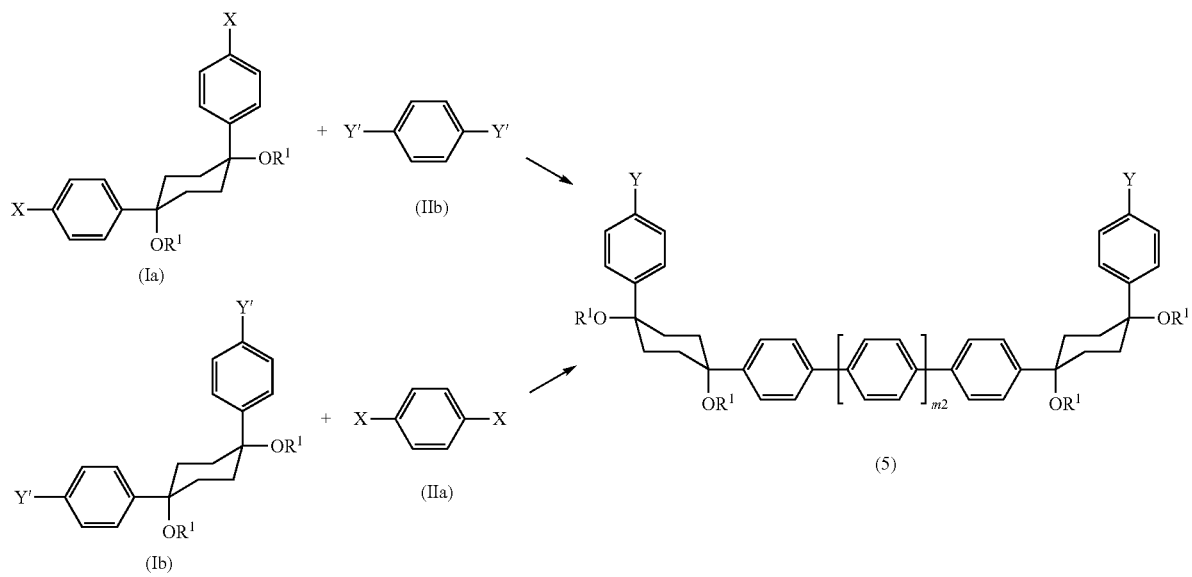

wherein $R^1$, X, Y, Y', and m2 are as defined above.

This reaction produces the compound represented by General Formula (5) as a U-shaped chain compound using the flexural portions of the cyclohexane rings.

The reaction of the compound represented by General Formula (I) and the compound represented by General Formula (II) is preferably performed by the Suzuki-Miyaura coupling reaction. More specifically, it is preferable to react either the compound represented by General Formula (Ia) with the compound represented by General Formula (IIb), or the compound represented by General Formula (Ib) with the compound represented by General Formula (IIa).

More specifically, in this reaction, it is preferable to use an excessive amount of the compound represented by General Formula (I). Specifically, the amount of the compound represented by General Formula (II) is preferably 0.05 to 0.2 mol, more preferably 0.075 to 0.15 mol, per mol of the compound represented by General Formula (I).

This reaction is generally performed using a palladium catalyst. The palladium catalyst used herein can be selected from the palladium catalysts described above. Among them, Pd(PPh$_3$)$_4$ and the like are preferable.

In terms of the yield, the amount of the palladium catalyst is generally 0.0001 to 0.1 mol, preferably 0.0005 to 0.02 mol, per mol of the compound represented by General Formula (I) used as a raw material.

Further, as required, it is possible to use a phosphorus ligand that can be coordinated with the palladium atom that is the center element of the palladium catalyst. This phosphorus ligand may be selected from the phosphorus ligands described above. Among them, 2-(dicyclohexylphosphino)-2',4',6'-tri-isopropyl-1,1'-biphenyl (X-Phos) and the like are preferable.

When a phosphorus ligand is used, the amount is, in terms of the yield, generally 0.001 to 1.0 mol, preferably 0.01 to 0.8 mol, per mol of the compound represented by General Formula (I) used as a raw material.

In addition to the palladium catalyst, a base (a reagent for activation of boron species) is preferably added. The base may be selected from the bases described above. Sodium carbonate and the like are preferable. The amount of the base (the activation reagent) is generally about 0.01 to 10 mol, preferably 0.1 to 5.0 mol, per mol of the compound represented by General Formula (I) used as a raw material.

This reaction is generally performed in the presence of a reaction solvent. The reaction solvent may be selected from the reaction solvents described above. Among them, in the present invention, cyclic ethers (such as tetrahydrofuran) are preferable. The system may contain water.

The reaction temperature in the above reaction step is generally selected from a temperature range of not less than 0° C. and not more than the boiling point of the reaction solvent.

Further, the reaction atmosphere in the above reaction step is not particularly limited; however, an inert gas atmosphere, such as an argon gas atmosphere, a nitrogen gas atmosphere, etc., is preferable. It is also possible to adopt an air atmosphere.

Compound Represented by General Formula (4)

As described above, the compound represented by General Formula (4) is obtained by first obtaining a compound represented by General Formula (5):

[Chem. 33]

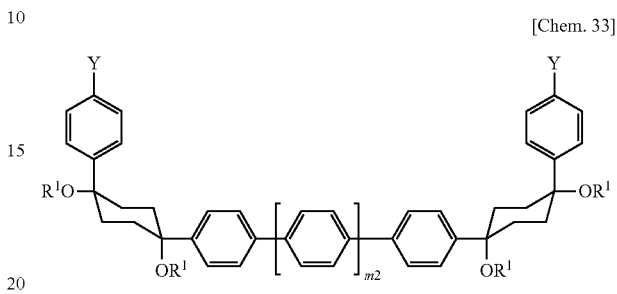

wherein $R^1$, Y, and m2 are as defined above, and then reacting the halogen atom, boronic acid, or an ester thereof at an end of the compound represented by General Formula (5) with the halogen atom, boronic acid, or an ester thereof at an end of the compound represented by General Formula (I) or the compound represented by General Formula (II).

[Chem. 34]

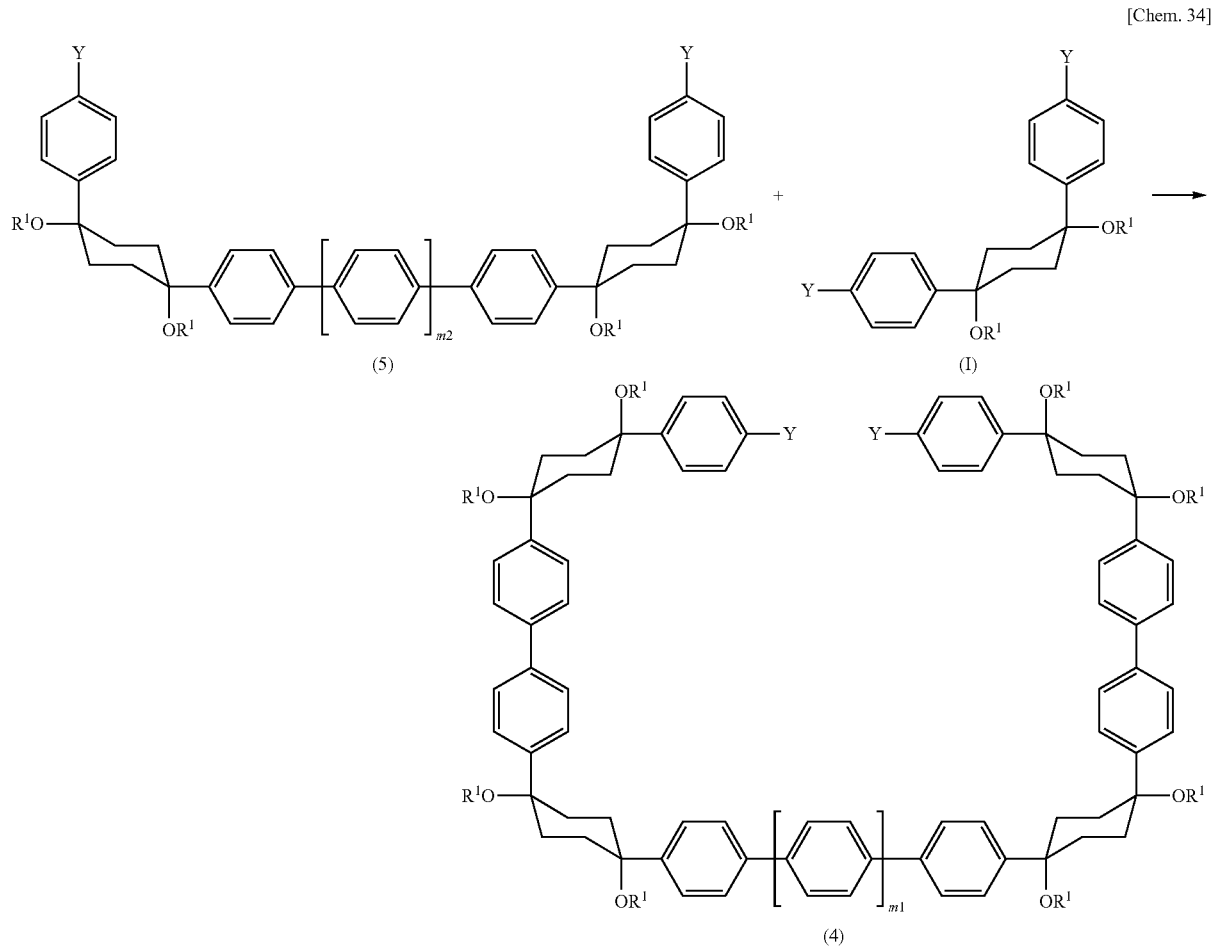

wherein $R^1$, Y, m1, and m2 are as defined above.

This reaction produces the compound represented by General Formula (4) as a C-shaped chain compound using the flexural portions of the cyclohexane rings.

The reaction of the compound represented by General Formula (5) and the compound represented by General Formula (I) is preferably performed by the Suzuki-Miyaura coupling reaction.

More specifically, in this reaction, it is preferable to use an excessive amount of the compound represented by General Formula (I). Specifically, the amount of the compound represented by General Formula (I) is preferably 5 to 20 mol, more preferably 7 to 15 mol, per mol of the compound represented by General Formula (5).

This reaction is generally performed using a palladium catalyst. The palladium catalyst used herein can be selected from the palladium catalysts described above. Among them, $Pd(PPh_3)_4$ and the like are preferable.

In terms of the yield, the amount of the palladium catalyst is generally 0.001 to 1 mol, preferably 0.005 to 0.5 mol, per mol of the compound represented by General Formula (5) used as a raw material.

Further, as required, it is possible to use a phosphorus ligand that can be coordinated with the palladium atom that is the center element of the palladium catalyst. This phosphorus ligand may be selected from the phosphorus ligands described above. Among them, 2-(dicyclohexylphosphino)-2',4',6'-tri-isopropyl-1,1'-biphenyl (X-Phos) and the like are preferable.

When a phosphorus ligand is used, the amount is, in terms of the yield, generally 0.001 to 1.0 mol, preferably 0.01 to 0.8 mol, per mol of the compound represented by General Formula (5) used as a raw material.

In addition to the palladium catalyst, a base (a reagent for activation of boron species) is preferably added. The base may be selected from the bases described above. Sodium carbonate, silver carbonate, and the like, are preferable. The amount of the base (the activation reagent) is generally about 0.01 to 10 mol, preferably 0.1 to 5.0 mol, per mol of the compound represented by General Formula (5) used as a raw material.

This reaction is generally performed in the presence of a reaction solvent. The reaction solvent may be selected from the reaction solvents described above. Among them, in the present invention, aromatic hydrocarbons (toluene, etc.) are preferable. The system may contain water.

The reaction temperature in the above reaction step is generally selected from a temperature range of not less than 0° C. and not more than the boiling point of the reaction solvent.

Further, the reaction atmosphere in the above reaction step is not particularly limited; however, an inert gas atmosphere, such as an argon gas atmosphere, a nitrogen gas atmosphere, etc., is preferable. It is also possible to adopt an air atmosphere.

Compound Represented by General Formula (6)

The compound represented by General Formula (6) is obtained, for example, by a reaction using the compound represented by General Formula (I) and the compound represented by General Formula (II). More specifically, the compound represented by General Formula (6) is obtained by reacting the halogen atom at an end of the compound represented by General Formula (Ia) or the compound represented by General Formula (IIa) with the boronic acid or an ester thereof at an end of the compound represented by General Formula (Ib) or the compound represented by General Formula (IIb).

[Chem. 35]

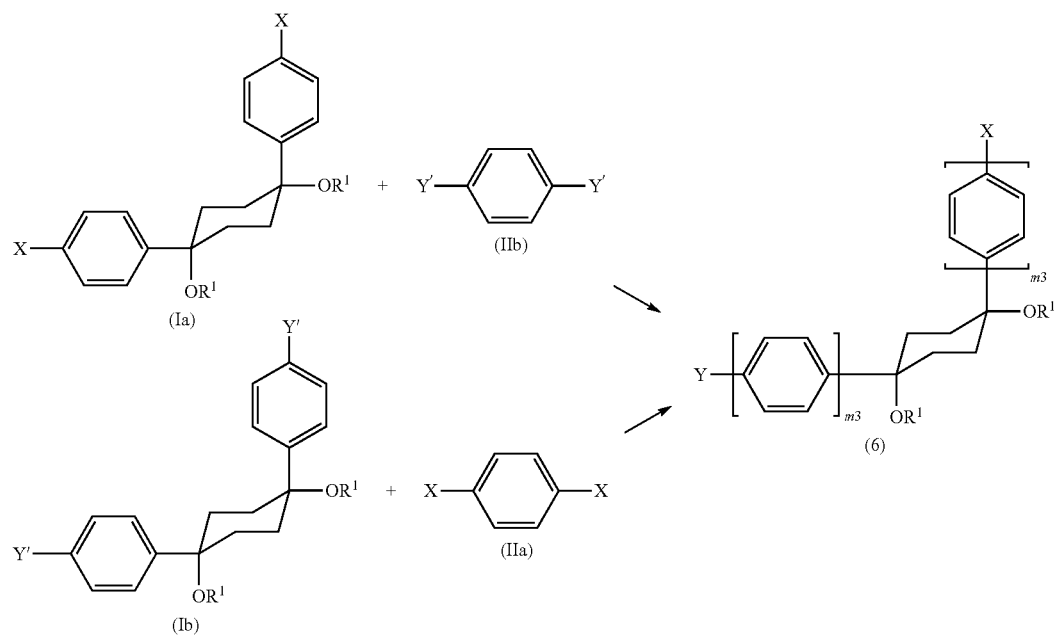

wherein $R^1$, X, Y, Y', and m3 are as defined above.

This reaction produces the compound represented by General Formula (6) as an L-shaped chain compound using the flexural portions of the cyclohexane rings.

The reaction of the compound represented by General Formula (I) and the compound represented by General Formula (II) is preferably performed by the Suzuki-Miyaura coupling reaction. More specifically, it is preferable to react either the compound represented by General Formula (Ia) with the compound represented by General Formula (IIb), or the compound represented by General Formula (Ib) with the compound represented by General Formula (IIa).

In this reaction, it is preferable to use an excessive amount of the compound represented by General Formula (II). Specifically, the amount of the compound represented by General Formula (II) is preferably 5 to 20 mol, more preferably 7 to 15 mol, per mol of the compound represented by General Formula (I).

This reaction is generally performed using a palladium catalyst. The palladium catalyst used herein can be selected from the palladium catalysts described above. Among them, Pd(PPh$_3$)$_4$ and the like are preferable.

In terms of the yield, the amount of the palladium catalyst is generally 0.0001 to 0.5 mol, preferably 0.0005 to 0.2 mol, per mol of the compound represented by General Formula (I) used as a raw material.

Further, as required, it is possible to use a phosphorus ligand that can be coordinated with the palladium atom that is the center element of the palladium catalyst. This phosphorus ligand may be selected from the phosphorus ligands described above. Among them, 2-(dicyclohexylphosphino)-2',4',6'-tri-isopropyl-1,1'-biphenyl (X-Phos) and the like are preferable.

When a phosphorus ligand is used, the amount is, in terms of the yield, generally 0.001 to 1.0 mol, preferably 0.01 to 0.8 mol, per mol of the compound represented by General Formula (I) used as a raw material.

In addition to the palladium catalyst, a base (a reagent for activation of boron species) is preferably added. The base may be selected from the bases described above. Silver carbonate and the like are preferable. The amount of the base (the activation reagent) is generally about 0.01 to 10 mol, preferably 0.1 to 5.0 mol, per mol of the compound represented by General Formula (I) used as a raw material.

This reaction is generally performed in the presence of a reaction solvent. The reaction solvent may be selected from the reaction solvents described above. Among them, in the present invention, cyclic ethers (such as tetrahydrofuran) are preferable.

The reaction temperature in the above reaction step is generally selected from a temperature range of not less than 0° C. and not more than the boiling point of the reaction solvent.

Further, the reaction atmosphere in the above reaction step is not particularly limited; however, an inert gas atmosphere, such as an argon gas atmosphere, a nitrogen gas atmosphere, etc., is preferable. It is also possible to adopt an air atmosphere.

First Embodiment

The method for producing a cyclic compound according to the first embodiment of the present invention is a method for producing a cyclic compound having 9 to 13 (in particular, 9, 11, or 13) bivalent aromatic hydrocarbon groups, bivalent heterocyclic groups, or derivative groups thereof. The method comprises the step of reacting, through intramolecular ring closure reaction, terminal atoms (in particular, halogen atoms) of a chain compound represented by General Formula (IV):

X—R$^4$—X wherein R$^4$ is a bivalent group having 3 to 4 structural units represented by General Formula (1):

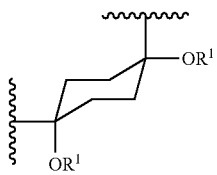

[Chem. 36]

wherein R$^1$ is as defined above,
and 6 or more (in particular, 6 to 9) bivalent aromatic hydrocarbon groups, bivalent heterocyclic groups, or derivative groups thereof; and X is as defined above, thereby obtaining a cyclic compound.

In this step, a cyclic compound is obtained by subjecting the compound represented by General Formula (IV) to intramolecular ring closure reaction. The compound represented by General Formula (IV) is obtained through a reaction using the above raw materials.

The compound represented by General Formula (IV) encompasses, among the above-described compounds, the compound represented by General Formula (3) and the compound represented by General Formula (4) having halogen atoms at the two ends. Therefore, other compounds represented by General Formula (IV) may also be obtained by the same method as the method for producing the compound represented by General Formula (3) and the compound represented by General Formula (4) having halogen atoms at the two ends.

In this reaction, the terminal atoms of the compound represented by General Formula (IV) are coupled, thereby forming a cyclic compound. The compound represented by General Formula (IV) has two halogen atoms. Thus, by using a nickel compound, these two halogen atoms are coupled, thus causing an intramolecular ring closure reaction.

In this step, the number of rings in the compound represented by General Formula (IV) directly corresponds to the number of rings in the cyclic compound of the present invention. Accordingly, by appropriately selecting the compound represented by General Formula (IV), it is possible to arbitrarily design the number of continuously bonded bivalent organic ring groups, thereby efficiently producing a cyclic compound in which a desired number of bivalent organic ring groups are continuously bonded with a short production process.

The intramolecular ring closure reaction uses a nickel compound. The nickel compound is not particularly limited; however, zerovalent nickel salts or bivalent nickel salts are preferable. They may be used singly, or in a combination of two or more. These complexes designate both a reagent to be added, and a product generated during the reaction.

The zerovalent nickel salts are not particularly limited, and examples thereof include bis(1,5-cyclooctadiene)nickel(0), bis(triphenylphosphine)nickeldicarbonyl, and nickelcarbonyl.

Further, examples of bivalent nickel salts include nickel(II) acetate, nickel(II)trifluoroacetate, nickel(II)nitrate, nickel(II) chloride, nickel(II)bromide, nickel(II)acetylacetonato, nickel (II)perchlorate, nickel(II)citrate, nickel(II)oxalate, nickel cyclohexanebutyrate, nickel(II)benzoate, nickel(II)stearate, nickel(II)stearate, nickel(II)sulfamate, nickel(II)carbonate, nickel(II)thiocyanate, nickel(II)trifluoromethanesulfonate, bis(1,5-cyclo-octadiene)nickel(II), bis(4-diethylamino dithiobenzyl)nickel (II), nickel(II) cyanide, nickel fluoride (II), nickel(II)boride, nickel(II)borate, nickel(II)hypophosphite, ammonium nickel(II)sulfate, nickel(II)hydroxide, nickel(II)cyclopentadienyl, hydrates thereof, and mixtures thereof.

Examples of zerovalent nickel salts and bivalent nickel salts also include compounds with previously coordinated ligands.

The amount of the nickel compound differs depending on the material used; however, the amount of the nickel compound used as a reagent is generally 0.01 to 50 mol, preferably 0.1 to 10 mol, per mol of the compound represented by General Formula (IV) used as a raw material.

A ligand that can be coordinated to nickel (a nickel atom) may be used as well as the nickel compound. Examples of such ligands include carboxylate-based ligands, amide-based ligands, phosphine-based ligands, oxime-based ligands, sulfonate-based ligands, 1,3-diketone-based ligands, Schiff base ligands, oxazoline-based ligands, diamine-based ligands, carbon monoxide ligands, carbene-based ligands, and the like. They may be used singly, or in a combination of two or more. The coordinating atoms in the ligands are a nitrogen atom, phosphorus atom, oxygen atom, sulfur atom, and the like. These ligands include monodentate ligands having a coordinating atom at one site, and multidentate ligands having coordinating atoms at two or more sites. Further, in carbon monoxide ligands and carbene-based ligands, carbon atoms serve as coordinating atoms.

Examples of monodentate ligands include triphenylphosphine, trimethoxyphosphine, triethylphosphine, tri(i-propyl) phosphine, tri(tert-butyl)phosphine, tri(n-butyl)phosphine, tri(isopropoxy)phosphine, tri(cyclopentyl)phosphine, tri(cyclohexyl)phosphine, tri(ortho-toluyl)phosphine, tri(mesityl) phosphine, tri(phenoxy)phosphine, tri-(2-furyl)phosphine, bis(p-sulfonatophenyl)phenylphosphine potassium, di(tert-butyl)methylphosphine, methyldiphenylphosphine, dimethylphenylphosphine, triethylamine, and pyridine.

Examples of bidentate ligands include 2,2'-bipyridine, 4,4'-(tert-butyl)bipyridine, phenanthroline, 2,2'-bipyrimidyl, 1,4-diazabicyclo[2,2,2]octane, 2-(dimethylamino)ethanol, tetramethylethylenediamine, N,N-dimethylethylenediamine, N,N'-dimethylethylenediamine, 2-aminomethylpyridine, or (NE)-N-(pyridine-2-ylmethyliden)aniline, 1,1'-bis(diphenylphosphino)ferrocene, 1,1'-bis(tert-butyl)ferrocene, diphenylphosphino methane, 1,2-bis(diphenylphosphino)ethane, 1,3-bis(diphenylphosphino)propane, 1,5-bis(diphenylphosphino)pentane, 1,2-bis(dipentafluorophenylphosphino) ethane, 1,2-bis(dicyclohexylphosphino)ethane, 1,3-(dicyclohexylphosphino)propane, 1,2-bis(di-tert-butylphosphino) ethane, 1,3-bis(di-tert-butylphosphino)propane, 1,2-bis (diphenylphosphino)benzene, 1,5-cyclooctadiene, 2,2'-bis (diphenylphosphino)-1,1'-binaphthyl (BINAP), 2,2'-dimethyl-6,6'-bis(diphenylphosphino)biphenyl (BIPHEMP), 1,2-bis(diphenylphosphino)propane (PROPHOS), 2,3-O-isopropylidene-2,3-dihydroxy-1,4-bis(diphenylphosphino)butane (DIOP), 3,4-bis(diphenylphosphino)-1-benzylpyrrolidine (DEGUPHOS), 1,2-bis [(2-methoxyphenyl)phenylphosphino]ethane (DIPAMP), substituted-1,2-bis-(phospholano)benzene (DuPHOS), 5,6-bis-(diphenylphosphino)-2-norbornene (NORPHOS), N,N'-bis (diphenylphosphino)-N,N'-bis(1-phenylethyl)ethylene diamine (PNNP), 2,4-bis (diphenylphosphino)pentane (SKEWPHOS), 1-[1',2-bis(diphenylphosphino)ferrocenyl] ethylene diamine (BPPFA), 2,2'-bis(dicyclohexylphosphino)-5,5',6,6',7,7',8,8'-octahydro-1,1'-binaphthyl, ((4,4'-bi-1,3-benzodioxole)-5,5'-diyl)bis (diphenylphosphine) (SEGPHOS), 2,3-bis(diphenylphosphino)butane (CHIRAPHOS), 1-[2-(2-substituted-phosphino)ferrocenyl]ethyl-2-substituted-phosphine (JOSIPHOS), and mixtures thereof.

Further, examples of BINAP include BINAP derivatives. Examples thereof include 2,2'-bis(diphenylphosphino)-1,1'-binaphthyl, 2,2'-bis(di-p-tolylphosphino)-1,1'-binaphthyl, 2,2'-bis(di-p-tertiary-butylphenylphosphino)-1,1'-binaphthyl, 2,2'-bis(di-m-tolylphosphino)-1,1'-binaphthyl, 2,2'-bis (di-3,5-dimethylphenylphosphino)-1,1'-binaphthyl, 2,2'-bis (di-p-methoxyphenylphosphino)-1,1'-binaphthyl, 2,2'-bis (dicyclopentylphosphino)-1,1'-binaphthyl, 2,2'-bis (dicyclohexylphosphino)-1,1'-binaphthyl, 2-di(β-naphthyl) phosphino-2'-diphenylphosphino-1,1'-binaphthyl, and 2-diphenylphosphino-2'-di(p-trifluoromethylphenyl)phosphino-1,1'-binaphthyl.

Further, examples of BIPHEMP include BIPHEMP derivatives. Examples thereof include 2,2'-dimethyl-6,6'-bis (diphenylphosphino-1,1'-biphenyl, 2,2'-dimethyl-6,6'-bis(dicyclohexylphosphino)-1,1'-biphenyl, 2,2'-dimethyl-4,4'-bis (dimethylamino)-6,6'-bis(diphenylphosphino)-1,1'-biphenyl, 2,2',4,4'-tetramethyl-6,6'-bis(diphenylphosphino)-1,1'-biphenyl, 2,2'-dimethoxy-6,6'-bis(diphenylphosphino)-1,1'-biphenyl, 2,2',3,3'-tetramethoxy-6,6'-bis (diphenylphosphino)-1,1'-biphenyl, 2,2',4,4'-tetramethyl-3, 3'dimethoxy-6,6'-bis(diphenylphosphino)-1,1'-biphenyl, 2,2'-dimethyl-6,6'-bis(di-p-tolylphosphino)-1,1'-biphenyl, 2,2'-dimethyl-6,6'-bis(di-p-tert-butylphenylphosphino)-1,1'-biphenyl, and 2,2',4,4'-tetramethyl-3,3'-dimethoxy-6,6'-bis (di-p-methoxyphenylphosphino)-1,1'-biphenyl.

When a ligand is used, the amount is generally 0.01 to 50 mol, preferably 0.1 to 10 mol, per mol of the compound represented by General Formula (IV) used as a raw material.

This reaction is generally performed in the presence of a reaction solvent. The reaction solvent may be selected from the reaction solvents described above. Among them, in the present invention, cyclic ethers (such as tetrahydrofuran) are preferable.

When a reaction solvent is used, the concentration of the raw material is preferably adjusted; however, it is preferable to avoid an excessively high concentration. Specifically, the concentration of the compound represented by General Formula (IV) is preferably 0.1 to 5 mmol/L, more preferably 0.2 to 3 mol/L.

The reaction temperature is generally selected from a temperature range of not less than 0° C. and not more than the boiling point of the reaction solvent.

Further, the reaction atmosphere in the above reaction step is not particularly limited; however, an inert gas atmosphere, such as an argon gas atmosphere, a nitrogen gas atmosphere, etc., is preferable. It is also possible to adopt an air atmosphere.

With this reaction, a cyclic compound is obtained. When the compound represented by General Formula (3) having a halogen atom at each end is used as the raw material, a compound represented by General Formula (a1):

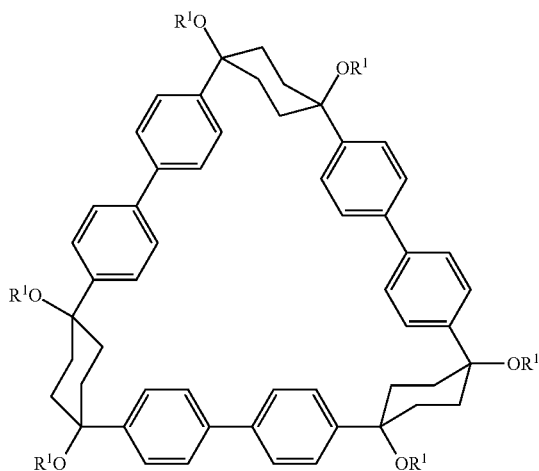

wherein R¹ is as defined above, is obtained.

Additionally, when the compound represented by General Formula (4), wherein the compound has a halogen atom at each end and m1 is 1, is used as the raw material, a compound represented by General Formula (a2):

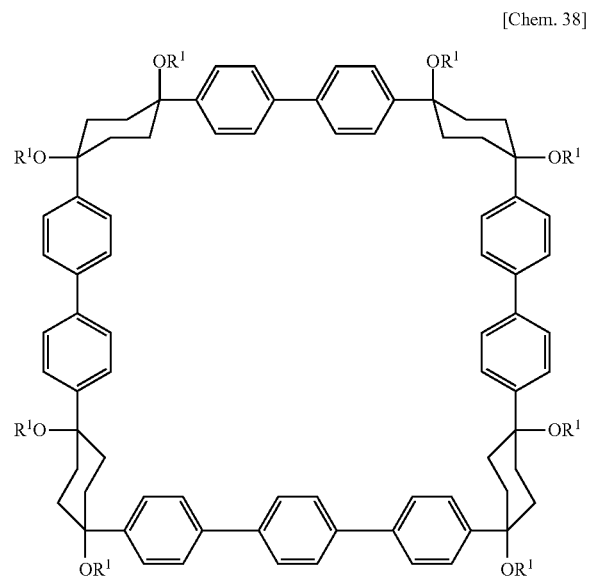

wherein R¹ is as defined above, is obtained.

Furthermore, in the same manner, a compound represented by General Formula (a3):

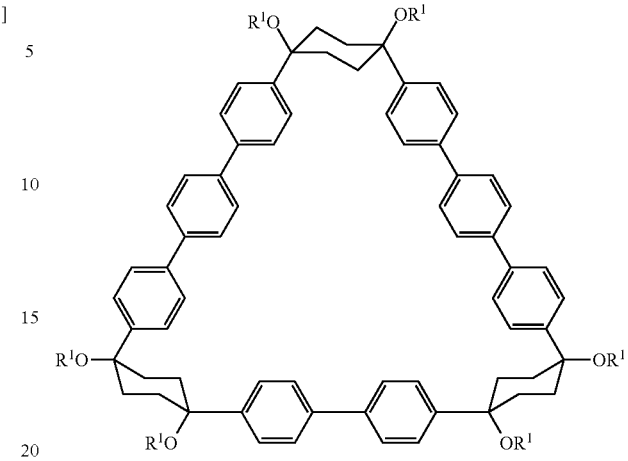

wherein R¹ is as defined above, is obtained.

Second Embodiment

A method for producing a cyclic compound according to the second embodiment of the present invention is a method for producing a cyclic compound having 10 to 13 (in particular, 10) bivalent aromatic hydrocarbon groups, bivalent heterocyclic groups, or derivative groups thereof. The method comprises the step of obtaining a cyclic compound by reacting a compound represented by General Formula (V-1):

$$Y-R^{5a}-Y$$

wherein $R^{5a}$ is a bivalent group having three structural units represented by General Formula (1), and 6 or more (in particular, 6 to 9) bivalent aromatic hydrocarbon groups, bivalent heterocyclic groups, or derivative groups thereof; and Y is the same or different, and each represents a halogen atom, or a boronic acid or an ester thereof; and a compound represented by General Formula (V-2):

$$Y-R^{5b}-Y$$

wherein $R^{5b}$ is a bivalent group having at least one (in particular, 1 to 4) bivalent aromatic hydrocarbon groups, bivalent heterocyclic groups, or derivative groups thereof; and Y is as defined above, or the step of obtaining a cyclic compound by reacting a compound represented by General Formula (VI-1):

$$Y-R^{6a}-Y$$

wherein $R^{6a}$ is a bivalent group having two structural units represented by General Formula (1) and 4 or more (in particular, 4 to 8) bivalent aromatic hydrocarbon groups, bivalent heterocyclic groups, or derivative groups thereof; Y is the same or different, and each represents a halogen atom, or a boronic acid or an ester thereof; and a compound represented by General Formula (VI-2):

$$Y-R^{6b}-Y$$

wherein $R^{6b}$ is a bivalent group having one structural unit represented by General Formula (1) and 2 or more (in particular, 2 to 6) bivalent aromatic hydrocarbon groups, bivalent heterocyclic groups, or derivative groups thereof; and Y is as defined above.

More specifically, a cyclic compound is obtained by reacting the compound represented by General Formula (V-1) and the compound represented by General Formula (V-2), or by reacting the compound represented by General Formula (VI-1) and the compound represented by General Formula (VI-2).

The compound represented by General Formula (V-1) encompasses the compound represented by General Formula (3), and the compound represented by General Formula (V-2) encompasses the compound represented by General Formula (II).

Accordingly, a cyclic compound is obtained by reacting the compound represented by General Formula (V-1) and the compound represented by General Formula (V-2). More specifically, for example, a cyclic compound is obtained by the reaction below:

[Chem. 40]

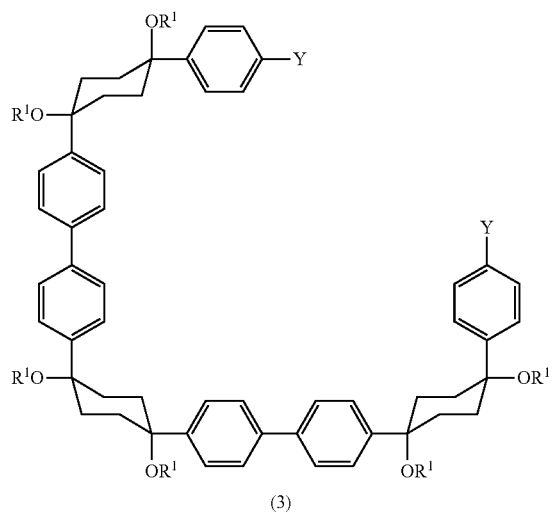

(3)

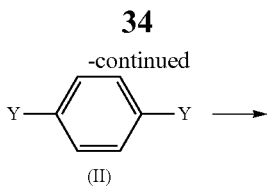

(II)

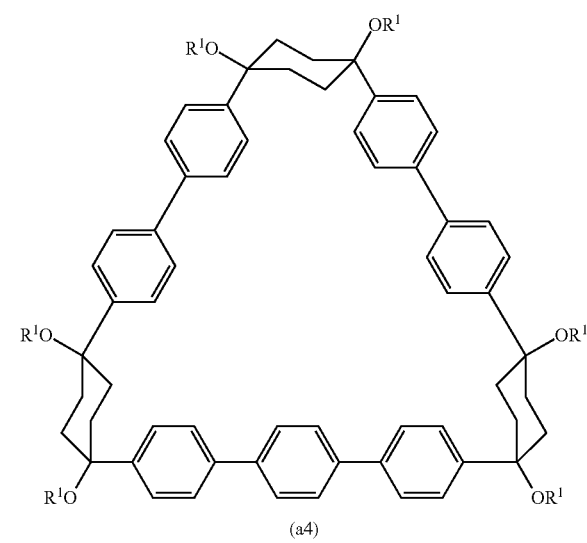

(a4)

wherein $R^1$ and Y are as defined above.

Further, the compound represented by General Formula (VI-1) encompasses the compound represented by General Formula (5), and the compound represented by General Formula (VI-2) encompasses the compound represented by General Formula (I) or the compound represented by General Formula (6).

Accordingly, a cyclic compound is obtained by reacting the compound represented by General Formula (VI-1) and the compound represented by General Formula (VI-2). More specifically, for example, a cyclic compound is obtained by the reaction below:

[Chem. 41]

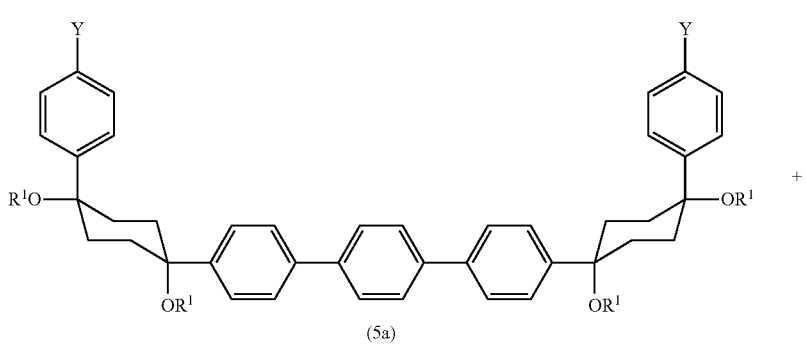

(5a)

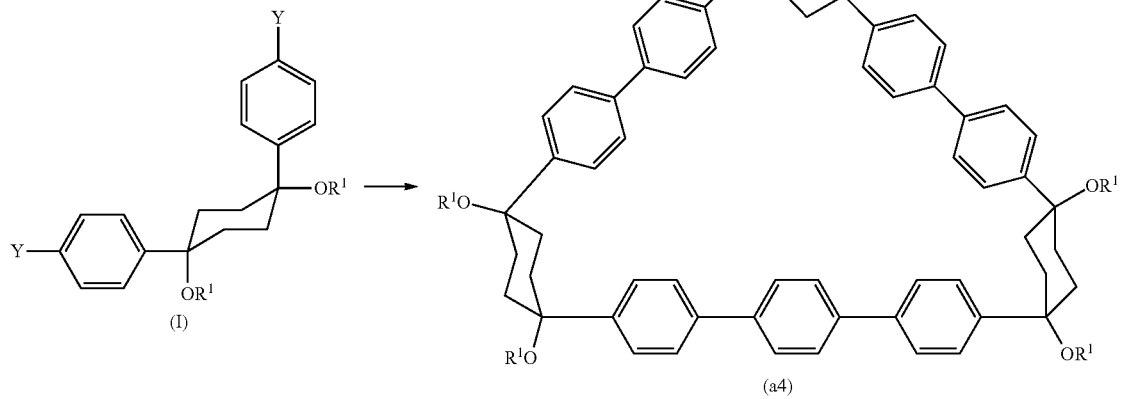

wherein $R^1$ and Y are as defined above.

Heretofore, only a method for producing a cyclic compound using a combination that obviously enables synthesis of a substantially rectangular or substantially triangular cyclic compound using the angles of the cyclohexane ring has been known. However, as shown above, the present invention makes it possible to adopt even a combination that presumably produces an irregular-shaped cyclic compound. Therefore, it is possible to synthesize cyclic compounds having various numbers of rings.

The reaction is not limited to the above reactions, and various combinations of the compound represented by (V-1) and the compound represented by (V-2), and various combinations of the compound represented by (VI-1) and the compound represented by (VI-2) can be adopted.

The above reaction is preferably performed by the Suzuki-Miyaura coupling reaction. More specifically, it is preferable that one of the compound represented by (V-1) and the compound represented by (V-2) has halogen atoms at the two ends, while the other has boronic acids or esters thereof at the two ends. Further, it is preferable that one of the compound represented by (VI-1) and the compound represented by (VI-2) has halogen atoms at the two ends, while the other has boronic acids or esters thereof at the two ends.

The amount of the compound represented by (V-2) is preferably 0.01 to 5.0 mol, more preferably 0.05 to 3.0 mol, per mol of the compound represented by (V-1). The amount of the compound represented by (VI-2) is preferably 0.01 to 5.0 mol, more preferably 0.05 to 3.0 mol, per mol of the compound represented by (VI-1).

In this reaction, a palladium catalyst is generally used. The palladium catalyst used herein can be selected from the palladium catalysts described above. Among them, $Pd(OAc)_2$ (Ac is an acetyl group), bis(dibenzylideneacetone)palladium (0), bis(tri-t-butyl phosphino)palladium (0), and the like, are preferable.

The amount of the palladium catalyst is, in terms of the yield, generally 0.0001 to 1.0 mol, preferably 0.0005 to 0.5 mol, per mol of the compound represented by (V-1) or the compound represented by (VI-1).

Further, as required, it is possible to use a phosphorus ligand that can be coordinated with the palladium atom that is the center element of the palladium catalyst. This phosphorus ligand may be selected from the phosphorus ligands described above. Among them, 2-(dicyclohexylphosphino)-2',4',6'-tri-isopropyl-1,1'-biphenyl (X-Phos) and the like are preferable.

When a phosphorus ligand is used, the amount is, in terms of the yield, generally 0.001 to 1.0 mol, preferably 0.01 to 0.8 mol, per mol of the compound represented by (V-1) or the compound represented by (VI-1) used as a raw material.

In addition to the palladium catalyst, a base (a reagent for activation of boron species) is preferably added. The base may be selected from the bases described above. Sodium hydroxide, potassium phosphate, and the like, are preferable. The amount of the base (the activation reagent) is generally about 0.01 to 10 mol, preferably 0.1 to 5.0 mol, per mol of the compound represented by (V-1) or the compound represented by (VI-1) used as a raw material.

This reaction is generally performed in the presence of a reaction solvent. The reaction solvent may be selected from the reaction solvents described above. Among them, in the present invention, cyclic ethers (such as dioxane) are preferable. The system may contain water.

When a reaction solvent is used, the concentration of the raw material is preferably adjusted; however, it is preferable to avoid an excessively high concentration. For example, in the reaction of the compound represented by (3) and the compound represented by (II), the concentration of the compound represented by (3) is preferably 0.1 to 5 mmol/L, more preferably 0.2 to 3 mol/L. Further, in the reaction of the compound represented by (5a) and the compound represented by (I), the concentration of the compound represented by (5a) is preferably 0.1 to 5 mmol/L, more preferably 0.2 to 3 mol/L.

The reaction temperature in the above reaction step is generally selected from a temperature range of not less than 0° C. and not more than the boiling point of the reaction solvent.

Further, the reaction atmosphere in the above reaction step is not particularly limited; however, an inert gas atmosphere, such as an argon gas atmosphere, a nitrogen gas atmosphere, etc., is preferable. It is also possible to adopt an air atmosphere.

The cyclic compound thus obtained is a cyclic compound having 3 to 4 structural units represented by General Formula (1):

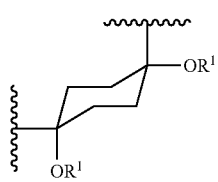

wherein R¹ is as defined above,
and 6 to 9 bivalent aromatic hydrocarbon groups, bivalent heterocyclic groups, or derivative groups thereof, and also is a cyclic compound in which the total number of the structural units represented by General Formula (1) and the bivalent aromatic hydrocarbon groups, bivalent heterocyclic groups, or derivative groups thereof is 10, 11, or 13.

Conversion of Cyclohexane Ring into Benzene

After the cyclic compound is obtained in the above manner, cyclohexane rings are converted into benzene rings to obtain the cyclic compound of the present invention.

For example, this step may be performed by a general oxidation reaction. For example, a method of heating a cyclic compound in the presence of acid (acid-treatment), a method of heating a cyclic compound in the presence of oxygen (in air atmosphere, oxygen atmosphere, etc.), a reaction with quinones, metallic oxidants, etc., may be adopted. Such processes are generally performed by a dehydrogenation reaction or the like, thereby chemically changing (aromatizing) the cyclohexane rings of a cyclic compound into benzene rings to synthesize a cyclic compound. More specifically, such processes eliminate the OR¹ in each cyclohexane ring contained in the cyclic compound before convertion, while advancing the dehydrogenation reaction, thereby yielding a cyclic compound.

When an acid treatment is performed, the method of the acid treatment is not particularly limited. Preferable examples thereof include the following methods.

(A) A method of dissolving the cyclic compound and an acid in a solvent, and reacting the resulting solution by heating.
(B) A method of dissolving the cyclic compound in a solvent, mixing the resulting solution with an acid, and reacting the resulting mixture by heating.

In the above conversion step, the acid treatment can be performed without a solvent.

The acid is not particularly limited; however, strong acids generally used as catalysts or the like are preferable. Examples thereof include sulfuric acids, methanesulfonic acids, para-toluenesulfonic acids, tungstophosphoric acids, tungstosilicic acids, molybdophosphoric acids, molybdosilicic acids, boron trifluoride etherates, and tin tetrachlorides. They may be used singly, or in a combination of two or more.

The amount of the acid may be varied depending on the production conditions, etc. In Method (A) above, the acid amount is preferably 0.01 to 100 mol, more preferably 0.5 to 50 mol, and further more preferably 1 to 20 mol, per mol of the cyclic compound.

In Method (B) above, the amount of the acid is preferably 0.01 to 100 mol, more preferably 0.5 to 50 mol, and further more preferably 1 to 20 mol, per mol of the cyclic compound.

Both nonpolar solvents and polar solvents may be used as solvents for the acid treatment reaction. Examples thereof include alkanes such as hexane, heptane, or octane; haloalkanes such as methylene chloride, chloroform, carbon tetrachloride, or ethylene chloride; benzenes such as benzene, toluene, xylene, mesitylene, or pentamethylbenzene; halobenzenes such as chrolobenzene or bromobenzene; ethers such as diethyl ether or anisole; and dimethylsulfoxides. These solvents may be used singly, or in a combination of two or more. In the reaction using a solvent, the reaction intermediate between the raw material and the cyclic compound may have low solubility with respect to the solvent used in this step. In this case, another solvent may be added in advance or during the reaction.

The heating temperature in Methods (A) and (B) above is not particularly limited; however, the heating temperature is generally 50° C. or more, preferably 80° C. or more, more preferably 100° C. or more, and yet more preferably 120° C. or more. When a solvent is used, the temperature is set in a range of not more than the boiling point of the solvent.

The heating is performed by using, for example, an oil bath, an aluminum block constant-temperature bath, a heat gun, a burner, microwave irradiation, etc. In the case of microwave irradiation, it is possible to use a known microwave reaction device for microwave reaction. Reflux cooling may be performed together with the heating process.

Further, the reaction atmosphere in the above acid treatment is not particularly limited; however, an inert gas atmosphere, such as an argon gas atmosphere, a nitrogen gas atmosphere, etc., may be adopted. It is also possible to adopt an air atmosphere.

Further, after the cyclic compound is thus obtained, a purification step may be performed as necessary. More specifically, general post-treatment steps, such as solvent removal (when a solvent is used), washing, chromatography separation, or the like, may be performed. In particular, because the obtained cyclic compound is usually amorphous (non-crystalline), the cyclic compound can be crystallized using a known recrystallization method for organic compounds. In the resulting crystal, the organic solvent used for the recrystallization may be incorporated in the ring of the molecule.

[3] Cyclic Compound Containing Functional Group

The organic compound containing a functional group of the present invention is a cyclic compound having 10 or more (in particularly preferably, 10 to 14, further preferably, 10, 12, or 14) bivalent aromatic hydrocarbon groups, bivalent heterocyclic groups, or derivative groups thereof in which at least one bivalent aromatic hydrocarbon group or bivalent heterocyclic group, or derivative group thereof is substituted with a group represented by General Formula (2):

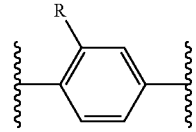

wherein R is a substituent.

In particular, the organic compound containing a functional group of the present invention preferably has one group represented by General Formula (2), and 9 or more (particularly preferably 9 to 13, further preferably 9, 11, or 13) bivalent aromatic hydrocarbon groups, bivalent heterocyclic groups, or derivative groups thereof.

The bivalent aromatic hydrocarbon group and the bivalent heterocyclic group are as defined above.

Further, the substituent represented by R is preferably a functional group that imparts a function that a cyclic compound having only hydrocarbons cannot have. Examples of the functional group include halogen atoms (such as fluorine atom, chlorine atom, bromine atom, or iodine atom); aryl groups optionally substituted with, for example, a C1-6 alkyl group or a C1-12 alkoxy group (such as 4-methoxyphenyl group); C1-12 alkoxy groups; hydroxy group; boryl groups; silyl groups; and amino group. Of these, halogen atoms are preferable. In the later-described production method of the present invention, the functional group is introduced into a raw material. To enable such introduction into a raw material, and, in particular, to prevent the function group from being a reaction site during the production, chlorine atom is more preferable.

More specifically, the compound having one compound represented by General Formula (2), and 9, 11, or 13 bivalent aromatic hydrocarbon groups, bivalent heterocyclic groups, or derivative groups thereof is represented by General Formula (B1) below:

[Chem. 44]

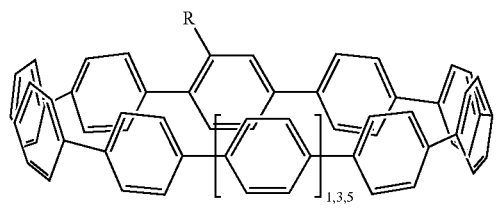

wherein R is as defined above.

For example, since a cycloparaphenylene compound having 12 benzene rings has 48 equivalent reaction sites, introduction of a functional group into a desired portion of such a compound has been difficult. However, the production method of the present invention enables introduction of a desired number of functional groups into desired portions.

[4] Method for Producing Cyclic Compound Containing Functional Group

The method for producing a cyclic compound containing a functional group of the present invention is a method for producing a cyclic compound containing a functional group in which one or more bivalent aromatic hydrocarbon groups, bivalent heterocyclic groups, or derivative groups thereof among 10 or more bivalent aromatic hydrocarbon groups, bivalent heterocyclic groups, or derivative groups thereof are substituted with a group represented by General Formula (2):

[Chem. 45]

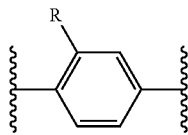

wherein R is as defined above.

The method comprises the step of converting cyclohexane rings of a cyclic compound having one or more (particularly preferably, 1 to 4, further preferably, 1) groups represented by General Formula (2), 3 to 4 groups represented by General Formula (1):

[Chem. 46]

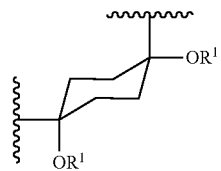

wherein $R^1$ is as defined above, and 6 or more bivalent aromatic hydrocarbon groups, bivalent heterocyclic groups, or derivative groups thereof, into benzene rings.

This cyclic compound is obtained by reacting a compound containing no functional group with the compound containing a functional group. A preferable example of the compound containing no functional group is a compound represented by General Formula (VII-1):

Y—$R^2$—Y wherein $R^2$ is a bivalent group having 1 to 3 structural units represented by General Formula (1), and 2 or more (in particular, 2 to 6) bivalent aromatic hydrocarbon groups, bivalent heterocyclic groups, or derivative groups thereof; and Y is as defined above.

Examples of the compound containing no functional group include the compound used as a raw material in "[2] Method for producing cyclic compound" described above. More specifically, examples include the compound represented by General Formula (I) and the compounds represented by General Formulas (3) to (6).

The compound containing a functional group is a compound represented by General Formula (VII-2):

Y—$R^3$—Y wherein $R^3$ is a bivalent group having one or more structural units represented by General Formula (2), 0 to 2 structural units represented by General Formula (1), and 0 or more bivalent aromatic hydrocarbon groups, bivalent heterocyclic groups, or derivative groups thereof; and Y is as defined above.

More specifically, the compound containing a functional group is a compound represented by General Formula (III):

[Chem. 47]

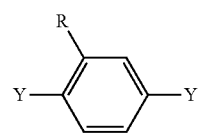

wherein R and Y are as defined above, or a compound obtained by reacting the compound represented by General Formula (III) with at least one of the aforementioned compound containing no functional group.

More specifically, examples of the compound obtained by reacting the compound represented by General Formula (III) with at least one of the aforementioned compound containing no functional group include a compound represented by General Formula (5'):

[Chem. 48]

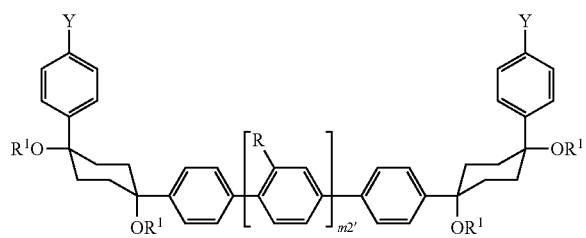

wherein R, R$^1$, and Y are as defined above; and m2' is an integer of 1 or more (preferably 1).

The compound represented by General Formula (5') can be synthesized using the compound represented by General Formula (III) instead of the compound represented by General Formula (II) in the same manner as the above-described synthesis of the compound represented by General Formula (5). The synthesis is specifically described below.

Compound Represented by General Formula (5')

The compound represented by General Formula (5') is obtained, for example, by a reaction using the compound represented by General Formula (I) and the compound represented by General Formula (III). More specifically, the compound represented by General Formula (5') is obtained by reacting a halogen atom at an end of the compound represented by General Formula (Ia) with a boronic acid or an ester thereof at an end of the compound represented by General Formula (IIIa).

More specifically, it is preferable to react either the compound represented by General Formula (Ia) with the compound represented by General Formula (IIIa), or the compound represented by General Formula (Ib) with the compound represented by General Formula (IIIb). By reacting the compound represented by General Formula (Ia) with the compound represented by General Formula (IIIa), the compound represented by General Formula (5') having a boronic acid or an ester thereof at each end is obtained. Further, by reacting the compound represented by General Formula (Ib) with the compound represented by General Formula (IIIb), the compound represented by General Formula (5') having a halogen atom at each end is obtained. Thereafter, the halogen atom may be converted into a boronic acid or an ester thereof through a borylation reaction using a boron compound, thereby obtaining a compound having a boronic acid or an ester thereof at each end.

Further, in this reaction, it is preferable to use an excessive amount of the compound represented by General Formula (I). Specifically, the amount of the compound represented by General Formula (I) is preferably 5 to 20 mol, more preferably 7 to 15 mol, per mol of the compound represented by General Formula (III).

This reaction is generally performed using a palladium catalyst. The palladium catalyst used herein can be selected from the palladium catalysts described above. Among them, Pd(PPh$_3$)$_4$, Pd(OAc)$_2$ (Ac represents an acetyl group), and the like, are preferable.

In terms of the yield, the amount of the palladium catalyst is generally 0.0001 to 0.15 mol, preferably 0.0005 to 0.07

[Chem. 49]

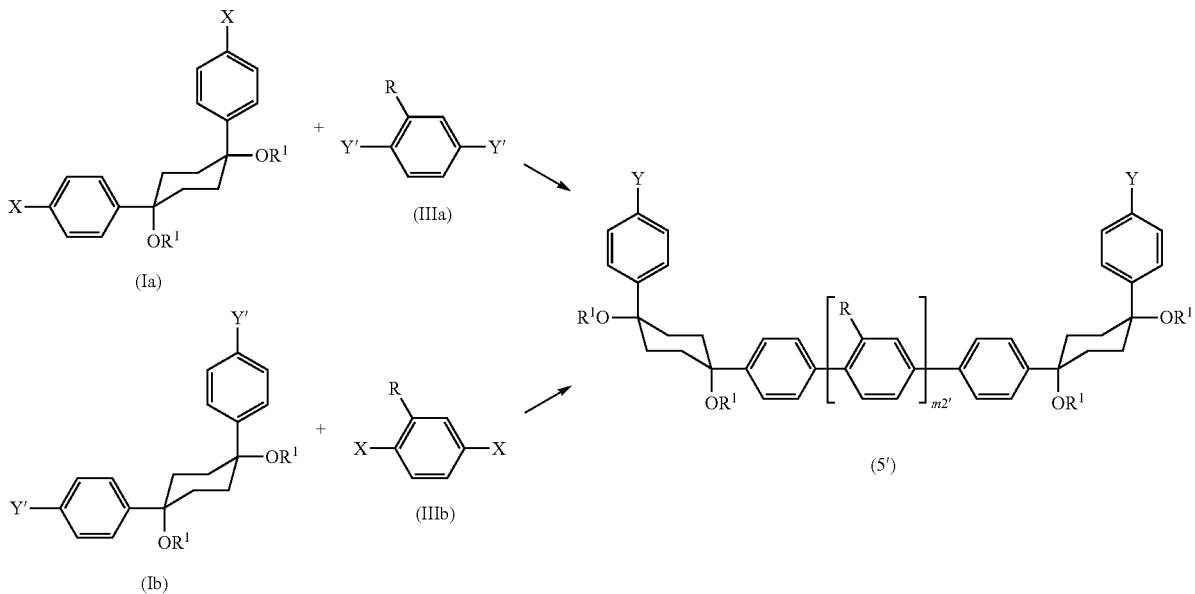

wherein R, R$^1$, X, Y, Y', and m2 are as defined above.

This reaction produces the compound represented by General Formula (5') as a U-shaped chain compound using the flexural portions of the cyclohexane rings.

The reaction of the compound represented by General Formula (I) and the compound represented by General Formula (III) is preferably performed by the Suzuki-Miyaura coupling reaction.

mol, per mol of the compound represented by General Formula (III) used as a raw material.

Further, as required, it is possible to use a phosphorus ligand that can be coordinated with the palladium atom that is the center element of the palladium catalyst. This phosphorus ligand may be selected from the phosphorus ligands described above. Among them, 2-(dicyclohexylphosphino)-2',4',6'-tri-isopropyl-1,1'-biphenyl (X-Phos) and the like are preferable.

When a phosphorus ligand is used, the amount is, in terms of the yield, generally 0.001 to 1.0 mol, preferably 0.01 to 0.8 mol, per mol of the compound represented by General Formula (III) used as a raw material.

In addition to the palladium catalyst, a base (a reagent for activation of boron species) is preferably added. The base may be selected from the bases described above. Sodium hydroxide, sodium carbonate, silver carbonate, and the like, are preferable. The reaction can be advanced with a particularly high yield when silver carbonate is used. The amount of the base (the activation reagent) is generally about 0.01 to 10 mol, preferably 0.1 to 5.0 mol, per mol of the compound represented by General Formula (III) used as a raw material.

This reaction is generally performed in the presence of a reaction solvent. The reaction solvent may be selected from the reaction solvents described above. Among them, in the present invention, cyclic ethers (such as dioxane or tetrahydrofuran) are preferable. The reaction can be advanced with a particularly high yield when tetrahydrofuran is used.

The reaction temperature in the above reaction step is generally selected from a temperature range of not less than 0° C. and not more than the boiling point of the reaction solvent.

Further, the reaction atmosphere in the above reaction step is not particularly limited; however, an inert gas atmosphere, such as an argon gas atmosphere, a nitrogen gas atmosphere, etc., is preferable. It is also possible to adopt an air atmosphere.

Examples of the reaction of the compound containing no functional group with the compound containing a functional group include the reaction below:

[Chem. 50]

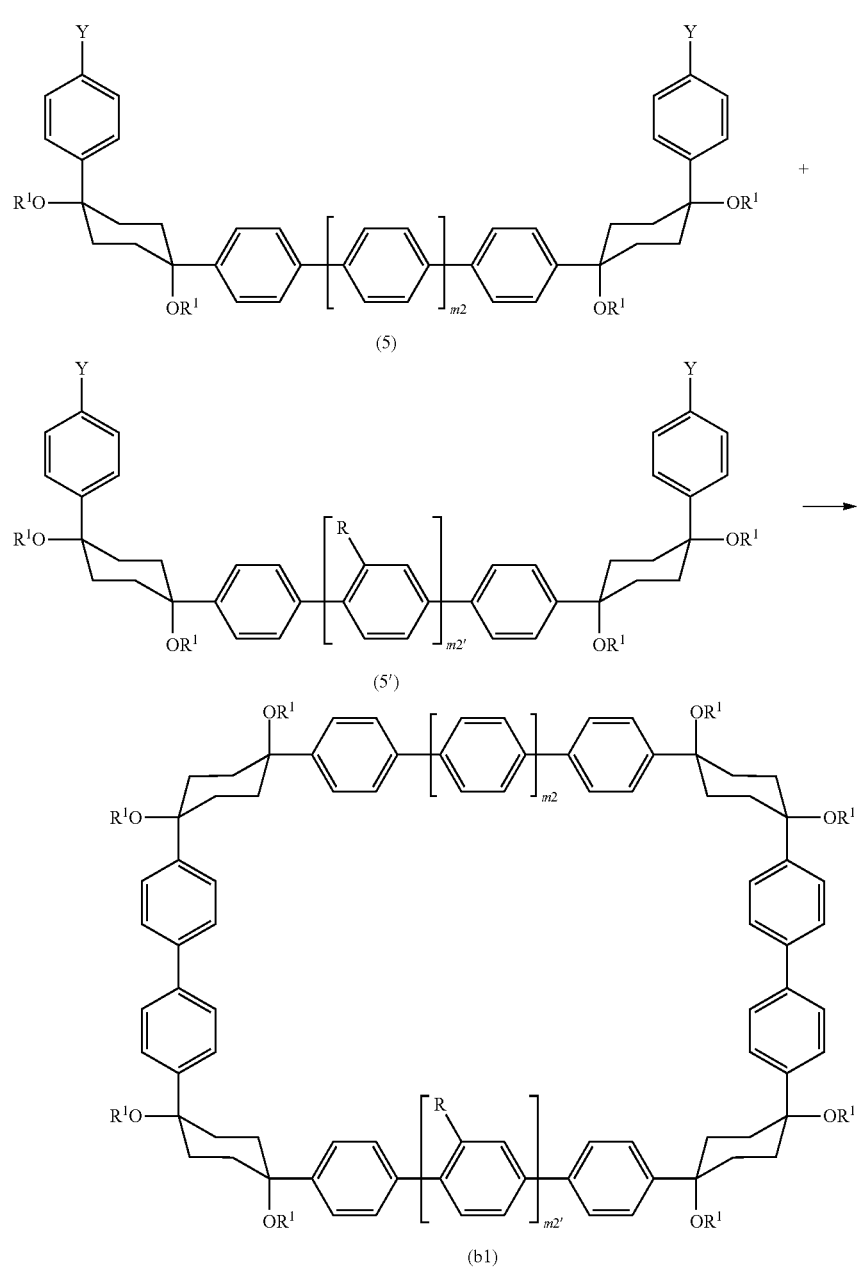

In addition to this reaction, a cyclic compound can also be obtained by, for example, the reaction below:

[Chem. 51]

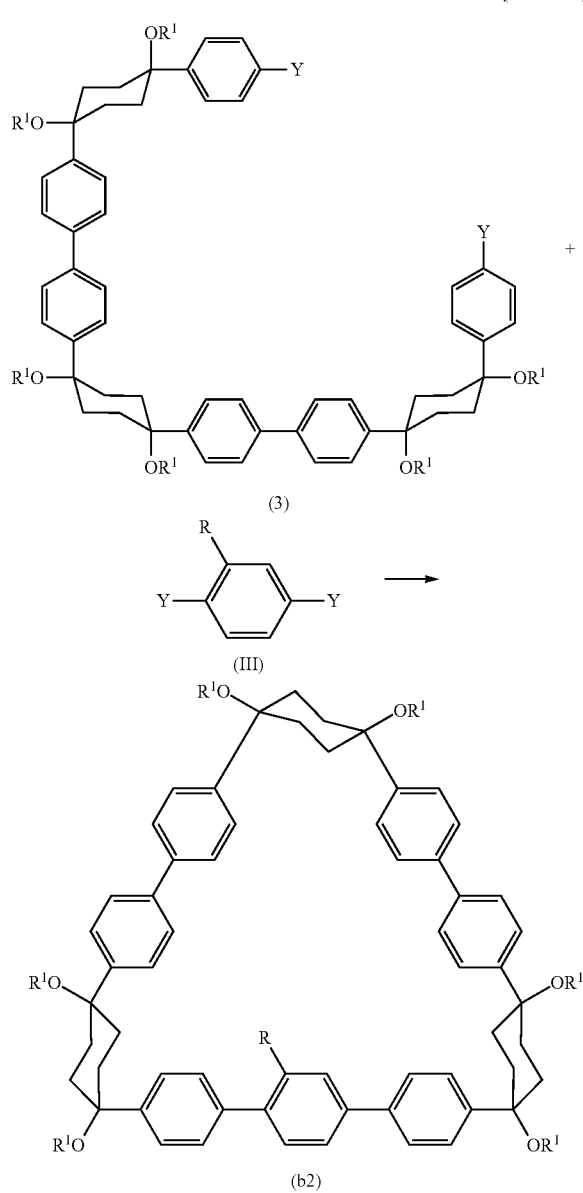

wherein R, R¹, X, Y, and Y' are as defined above.

The reaction is not limited to the reactions using the above combinations. Various reactions may be used to obtain a cyclic compound.

The above reaction is preferably performed by the Suzuki-Miyaura coupling reaction. More specifically, it is preferable that one of the compound containing no functional group and the compound containing a functional group has halogen atoms at the two ends, while the other has boronic acids or esters thereof at the two ends.

The amounts of the compound containing no functional group and the compound containing a functional group are preferably adjusted according to the combination of the compounds used in the reaction. Specifically, when the compound represented by General Formula (5) is reacted with the compound represented by General Formula (5'), the amount of the compound represented by General Formula (5) is preferably 0.01 to 5.0 mol, more preferably 0.05 to 3.0 mol, per mol of the compound represented by General Formula (5'). Further, when the compound represented by General Formula (3) is reacted with the compound represented by General Formula (III), the amount of the compound represented by General Formula (III) is preferably 0.01 to 5.0 mol, more preferably 0.05 to 3.0 mol, per mol of the compound represented by General Formula (3).

In this reaction, a palladium catalyst is generally used. The palladium catalyst used herein can be selected from the palladium catalysts described above. Among them, $Pd(OAc)_2$ (Ac is an acetyl group) is preferable.

The amount of the palladium catalyst is also preferably adjusted. When the compound represented by General Formula (5) is reacted with the compound represented by General Formula (5'), the amount of the palladium catalyst is preferably 0.0001 to 1.0 mol, more preferably 0.0005 to 0.5 mol, per mol of the compound represented by General Formula (5'). Further, when the compound represented by General Formula (3) is reacted with the compound represented by General Formula (III), the amount of the palladium catalyst is preferably 0.0001 to 1.0 mol, more preferably 0.0005 to 0.5 mol, per mol of the compound represented by General Formula (3).

Additionally, as required, it is possible to use a phosphorus ligand that can be coordinated with the palladium atom that is the center element of the palladium catalyst. This phosphorus ligand may be selected from the phosphorus ligands described above. Among them, 2-(dicyclohexylphosphino)-2',4',6'-tri-isopropyl-1,1'-biphenyl (X-Phos), 2-(dicyclohexylphosphino)-2',6'-dimethoxy-1,1'-biphenyl (S-Phos), and the like are preferable.

When a phosphorus ligand is used, the amount is also preferably adjusted. When the compound represented by General Formula (5) is reacted with the compound represented by General Formula (5'), the amount of the phosphorus ligand is preferably 0.001 to 1.0 mol, more preferably 0.01 to 0.8 mol, per mol of the compound represented by General Formula (5'). Further, when the compound represented by General Formula (3) is reacted with the compound represented by General Formula (III), the amount of the phosphorus ligand is preferably 0.001 to 1.0 mol, more preferably 0.01 to 0.8 mol, per mol of the compound represented by General Formula (3).

In addition to the palladium catalyst, a base (a reagent for activation of boron species) is preferably added. The base may be selected from the bases described above. Sodium hydroxide, potassium phosphate, and the like are preferable. The amount of the base (the activation reagent) is, although it is preferably adjusted, generally about 0.01 to 50 mol, preferably 0.1 to 20 mol, per mol of the compound containing no functional group or the compound containing a functional group used as a raw material.

This reaction is generally performed in the presence of a reaction solvent. The reaction solvent may be selected from the reaction solvents described above. Among them, in the present invention, cyclic ethers (such as dioxane or tetrahydrofuran) are preferable. When the compound represented by General Formula (5) is reacted with the compound represented by General Formula (5'), tetrahydrofuran is particularly preferable in terms of the yield. When the compound represented by General Formula (3) is reacted with the compound represented by General Formula (III), dioxane is particularly preferable in terms of the yield.

When a reaction solvent is used, the concentration of the raw material is preferably adjusted; however, it is preferable to avoid an excessively high concentration. For example, in the reaction of the compound represented by General Formula (5) and the compound represented by General Formula (5'), the concentration of the compound represented by General Formula (5') is preferably 0.1 to 5 mmol/L, more preferably 0.2 to 3 mol/L. Further, in the reaction of the compound represented by General Formula (3) and the compound represented by General Formula (III), the concentration of the compound represented by General Formula (3) is preferably 0.1 to 5 mmol/L, more preferably 0.2 to 3 mol/L.

The reaction temperature is generally selected from a temperature range of not less than 0° C. and not more than the boiling point of the reaction solvent.

Further, the reaction atmosphere is not particularly limited; however, an inert gas atmosphere, such as an argon gas atmosphere, a nitrogen gas atmosphere, etc., is preferable. It is also possible to adopt an air atmosphere.

The cyclic compound thus obtained is a cyclic compound having one or more groups represented by General Formula (2),

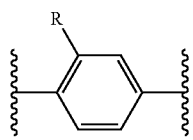

[Chem. 52]

wherein $R^1$ is as defined above,
3 to 4 groups represented by General Formula (1):

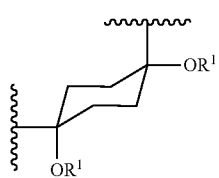

[Chem. 53]

wherein $R^1$ is as defined above,
and 6 or more bivalent aromatic hydrocarbon groups, bivalent heterocyclic groups, or derivative groups thereof.

Conversion of Cyclohexane Ring into Benzene

After the cyclic compound is obtained in the above manner, cyclohexane rings are converted into benzene rings to obtain the cyclic compound of the present invention.

For example, this step may be performed by a general oxidation reaction. For example, a method of heating a cyclic compound in the presence of acid (acid treatment), a method of heating a cyclic compound in the presence of oxygen (in air atmosphere, oxygen atmosphere, etc.), a reaction with quinones, metallic oxidants, etc., may be adopted. Such processes are generally performed by a dehydrogenation reaction or the like, thereby chemically changing (aromatizing) the cyclohexane rings of a cyclic compound into benzene rings to synthesize a cyclic compound. More specifically, such processes eliminate the $OR^1$ in each cyclohexane ring contained in the cyclic compound before convertion, while advancing the dehydrogenation reaction, thereby yielding a cyclic compound.

When an acid treatment is performed, the method of the acid treatment is not particularly limited. Preferable examples thereof include the following methods.

(A) A method of dissolving the cyclic compound and an acid in a solvent, and reacting the resulting solution by heating.
(B) A method of dissolving the cyclic compound in a solvent, mixing the resulting solution with an acid, and reacting the resulting mixture by heating.

In the above conversion step, the acid treatment can be performed without a solvent.

The acid is not particularly limited; however, strong acids generally used as catalysts or the like are preferable. Examples thereof include sulfuric acids, methanesulfonic acids, para-toluenesulfonic acids, tungstophosphoric acids, tungstosilicic acids, molybdophosphoric acids, molybdosilicic acids, boron trifluoride etherates, and tin tetrachlorides. They may be used singly, or in a combination of two or more.

The amount of the acid may be varied depending on the production conditions, etc. In Method (A) above, the acid amount is preferably 0.01 to 100 mol, more preferably 0.5 to 50 mol, and further more preferably 1 to 20 mol, per mol of the cyclic compound.

In Method (B) above, the amount of the acid is preferably 0.01 to 100 mol, more preferably 0.5 to 50 mol, and further more preferably 1 to 20 mol, per mol of the cyclic compound.

Both nonpolar solvents and polar solvents may be used as solvents for the acid treatment reaction. Examples thereof include alkanes such as hexane, heptane, or octane; haloalkanes such as methylene chloride, chloroform, carbon tetrachloride, or ethylene chloride; benzenes such as benzene, toluene, xylene, mesitylene, or pentamethylbenzene; halobenzenes such as chrolobenzene or bromobenzene; ethers such as diethyl ether or anisole; and dimethylsulfoxides. These solvents may be used singly, or in a combination of two or more. In the reaction using a solvent, the reaction intermediate between the raw material and the cyclic compound may have low solubility with respect to the solvent used in this step. In this case, another solvent may be added in advance or during the reaction.

The heating temperature in Methods (A) and (B) above is not particularly limited; however, the heating temperature is generally 50° C. or more, preferably 80° C. or more, more preferably 100° C. or more, and yet more preferably 120° C. or more. When a solvent is used, the temperature is set in a range of not more than the boiling point of the solvent.

The heating is performed by using, for example, an oil bath, an aluminum block constant-temperature bath, a heat gun, a burner, microwave irradiation, etc. In the case of microwave irradiation, it is possible to use a known microwave reaction device for microwave reaction. Reflux cooling may be performed together with the heating process.

Further, the reaction atmosphere in the above acid treatment is not particularly limited; however, an inert gas atmosphere, such as an argon gas atmosphere, a nitrogen gas atmosphere, etc., may be adopted. It is also possible to adopt an air atmosphere.

Further, after the cyclic compound is thus obtained, a purification step may be performed as necessary. More specifically, general post-treatment steps, such as solvent removal (when a solvent is used), washing, chromatography separation, or the like, may be performed. In particular, because the obtained cyclic compound is usually amorphous (non-crystalline), the cyclic compound can be crystallized using a known recrystallization method for organic compounds. In the resulting crystal, the organic solvent used for the recrystallization may be incorporated in the ring of the molecule.

After producing the cyclic compound containing a functional group of the present invention in the above manner, it is possible to substitute the functional group with a different functional group by a known method.

EXAMPLES

Hereinafter, the present invention is described in further detail with reference to Examples. However, the scope of the invention is not limited to these Examples.

Thin-layer chromatography (TLC) was performed using E. Merck silica gel 60 F254 precoated plates (0.25 mm). The chromatogram was analyzed by UV lamp (254 nm). Flash column chromatography (FCC) was performed using E. Merck silica gel 60 F254 (230-400 mesh). Preparative thin-layer chromatography (PTLC) was performed using Wakogel B5-F silica-coated plates (0.75 mm). Recycling preparative gel permeation chromatography (GPC) was performed with JAI LC-9204 (preparative column: JAIGEL-1H/JAIGEL-2H, chloroform). Mass spectra were recorded on a Waters Micromass LCT Premier (electrospray ionization time-of-flight mass spectrometry, ESI-TOFMS), JEOL JMS700 (fast atom bombardment mass spectroscopy, FAB-MS), and Bruker Daltonics Ultraflex III TOF/TOF (MALDI-TOF-MS). Elemental analyses were performed with Yanako MT-6. Melting points were measured on a MPA100 OptiMelt automated melting point system. Nuclear magnetic resonance (NMR) spectra were recored on a JEOL GSX-270 spectrometer ($^1$H 270 MHz, $^{13}$C 67.8 MHz), a JEOL JNM-ECS400 spectrometer ($^1$H 400 MHz, $^{13}$C 100 MHz), and a JEOL JNM-ECA-600 spectrometer ($^1$H 600 MHz, $^{13}$C 150 MHz), in CDCl$_3$ or DMSO-d6. Chemical shifts for $^1$H NMR are expressed in ppm relative to tetramethylsilane (δ 0.00 ppm), CHCl$_3$ (δ 7.26 ppm), or CDCl$_2$ (δ 5.32 ppm). Chemical shifts for $^{13}$C NMR are expressed in ppm relative to CDCl$_3$ (δ 77.0 ppm).

Synthesis Example 1

Compound (Ia-1)

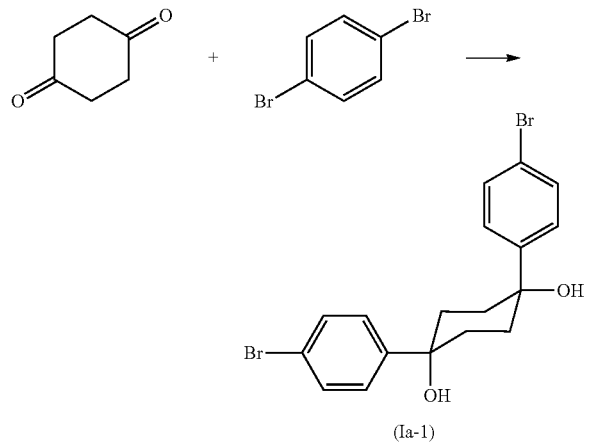

[Chem. 54]

To a 1-L round-bottom flask were added lithium chloride (LiCl) (1.68 g, 33 mmol) and cerium(III)trichloride heptahydrate (14.4 g, 0.33 mol). This flask was immersed in an oil bath, and heated at 90° C. for 2 hours under vacuum to dry. The obtained reactant mixture was crushed into a powder, and the powdered reactant mixture was returned to the flask. The flask was immersed again in an oil bath, and heated at 90° C. for 1 hour under vacuum. A stirring bar was added to the flask, and the flask was immersed again in an oil bath and heated at 150° C. for 3 hours under vacuum while stirring. While the content in the flask was still hot, argon gas was introduced into the flask. Dry tetrahydrofuran (THF) (200 mL) was added thereto, and the mixture was suspended. The resulting suspension was stirred at room temperature (i.e., about 23° C.; the same applies hereinafter) for about 8 hours. A solution of cyclohexane-1,4-dione (1.68 g, 15 mmol) in THF (15 mL) was added to the suspension via a cannula. The mixture was stirred at room temperature for 2 hours and cooled to −78° C., thereby obtaining Suspension A.

To another 1-L round-bottom flask were added 1,4-dibromobenzene (10.7 g, 45 mmol) and dry THF (90 mL). A solution of n-butyllithium in hexane (29.5 mL, 1.57 M, 45 mmol) was gradually added thereto dropwise at −78° C. (addition rate: 4.5 cm$^3$/min). After completion of dropwise addition, the mixture was stirred at −78° C. for 30 minutes, and the resulting solution was added to Suspension A obtained above via a cannula, thereby obtaining a mixture.

The mixture was stirred at −78° C. for 1 hour, followed by stirring at room temperature for 2 hours. A saturated NH$_4$Cl aqueous solution (50 mL) was then added to the mixture to stop the reaction. The resulting product was passed through Celite, and the filtrate was concentrated with an evaporator. Then, ethyl acetate was added to the residue (concentrate) to extract a crude product, which was dried over anhydrous Na$_2$SO$_4$, thereby obtaining an ethyl acetate solution. The solution was concentrated with an evaporator, and the residue (concentrate) was recrystallized from chloroform to yield the target compound as a white solid (5.32 g) (yield: 83%).

$^1$H NMR (270 MHz, CDCl$_3$) δ 1.71 (s, 2H), d 2.07 (s, 8H), 7.34 (d, J=8.6 Hz, 4H), 7.47 (d, J=8.6 Hz, 4H); $^{13}$C NMR (67.5 MHz, CDCl$_3$) δ 33.2 (CH$_2$), 72.3 (4°), 121.5 (4°), 127.2 (CH), 131.6 (CH), 144.6 (4°); HRMS (FAB, negative) m/z calcd for C$_{18}$H$_{17}$Br$_2$O$_2$ [M−H]$^-$: 422.9595, found 422.9576; mp: 177.7-178.7° C.

Synthesis Example 2

Compound (Ia-2)

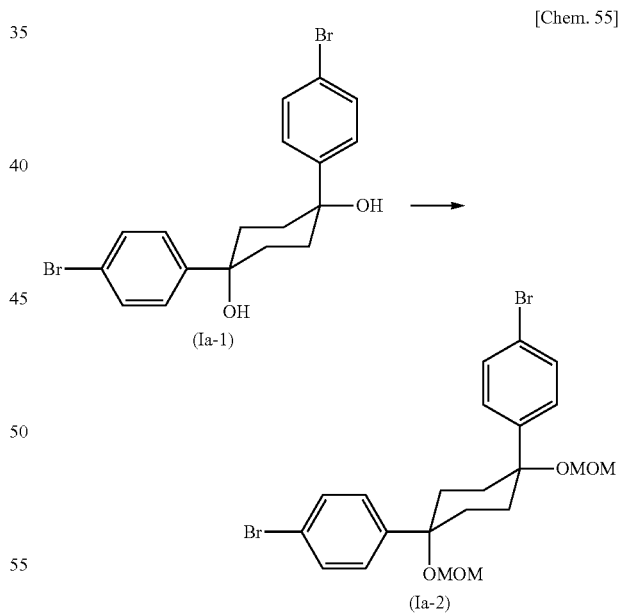

[Chem. 55]

In the formula, MOM represents a methoxymethyl group.

To a 200-mL round-bottom flask containing a stirring bar were added Compound (Ia-1) (4.69 g, 11 mmol) obtained in Synthesis Example 1, dry dichloromethane (CH$_2$Cl$_2$) (44 mL), and diisopropylethylamine (7.7 mL, 44 mmol), and the flask was immersed in an ice bath. The mixture in the flask was stirred at 0° C. for 30 minutes, and methoxymethyl chloride (3.5 mL, 46 mmol) was further added thereto. After the mixture was reacted at room temperature for 18 hours while stirring, a saturated NH$_4$Cl aqueous solution (20 mL) was added thereto to stop the reaction. The resulting product was extracted with CH$_2$Cl$_2$ (20 mL×3), and the organic phase from the extraction was dried over anhydrous Na$_2$SO$_4$, thereby obtaining a solution. The solution was concentrated with an evaporator, and the residue (concentrate) was purified by silica gel chromatography (CH$_2$Cl$_2$) to yield the target compound as a white solid (5.48 g) (yield: 97%).

$^1$H NMR (270 MHz, CDCl$_3$) δ 1.71 (s, 2H), 2.07 (s, 8H), 7.34 (d, J=9 Hz, 4H), 7.47 (d, J=9 Hz, 4H); $^{13}$C NMR (150 MHz, CDCl$_3$) δ 33.0 (CH$_2$), 56.2 (CH$_3$), 77.9 (4°), 92.3 (CH$_2$), 121.8 (4°), 128.7 (CH), 131.6 (CH), 141.6 (br, 4°); HRMS (FAB) m/z calcd for C$_{22}$H$_{26}$Br$_2$O$_4$Na [M$^+$Na]$^+$: 535.0096, found 535.0103. mp: 107.1-108.9° C.

Synthesis Example 3

Compound (Ib-1)

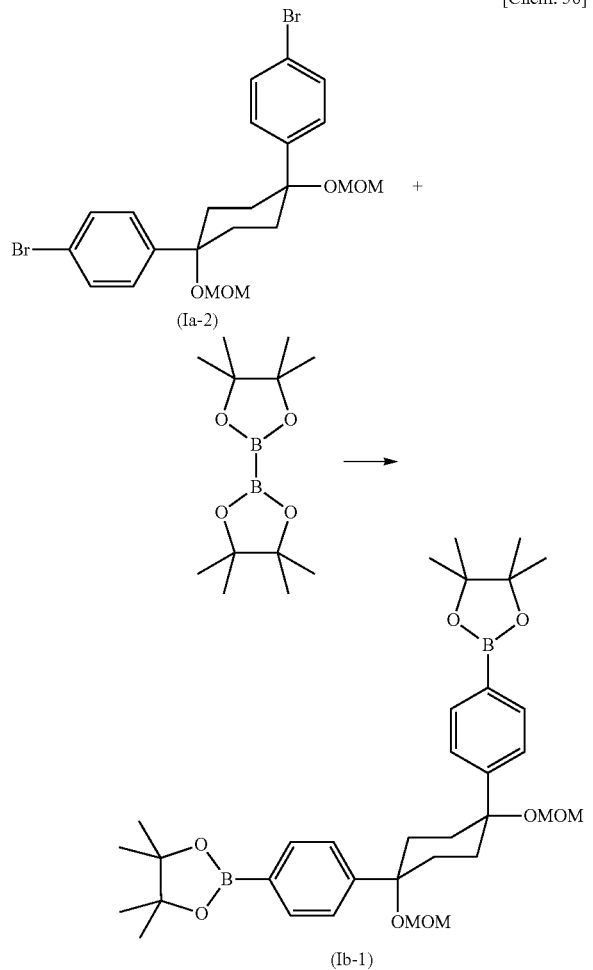

In the formula, MOM represents a methoxymethyl group.

To a 50-mL Schlenk flask containing a stirring bar were added Compound (Ia-2) (518 mg, 1.0 mmol) obtained in Synthesis Example 2, bis(pinacolate)diboron (636 mg, 2.5 mmol), 1,1'-bis(diphenylphosphino)ferrocene-palladium(II) dichloride-dichloromethane complex (PdCl$_2$(dppf).CH$_2$Cl$_2$) (23.2 mg, 30 μmol), potassium acetate (KOAc) (624 mg, 6.35 mmol), and dry dimethylsulfoxide (DMSO) (20 mL). The Schlenk flask was heated at 80° C. for 17 hours while stirring. After being cooled to room temperature, the reaction mixture was quenched with water. The resulting product was extracted with ethyl acetate (EtOAc), and the organic phase was dried over Na$_2$SO$_4$ and concentrated under reduced pressure. The crude product was purified by recycling preparative gel permeation chromatography (chloroform) to yield the target compound as a white solid (390 mg) (yield: 64%).

$^1$H NMR (600 MHz, CDCl$_3$) δ 1.33 (s, 24H), 2.09 (br, 4H), 2.31 (br, 4H), 3.40 (s, 6H), 4.41 (s, 4H), 7.43 (d, J=8 Hz, 4H), 7.76 (d, J=8 Hz, 4H); $^{13}$C NMR (150 MHz, CDCl$_3$) δ 24.9 (CH$_3$), 32.9 (CH$_2$), 56.0 (CH$_3$), 78.3 (4°), 83.8 (4°), 92.2 (CH$_2$), 126.2 (CH), 128.1 (4°), 134.8 (CH); HRMS (FAB) m/z calcd for C$_{34}$H$_{50}$B$_2$NaO$_8$ [M·Na]$^+$: 631.3584, found 631.3605.

The same reaction was performed by using a compound having iodine atoms at both ends, in place of Compound (Ia-2) having bromine atoms at both ends, under the same conditions (provided that the amounts of bis(pinacolate)diboron, PdCl$_2$(dppf).CH$_2$Cl$_2$, and KOAc were changed to 2.7 mmol, 32 μmol, and 9.0 mmol, respectively). It was possible to thereby improve the yield to 83%.

Synthesis Example 4

Compound (3a-1)

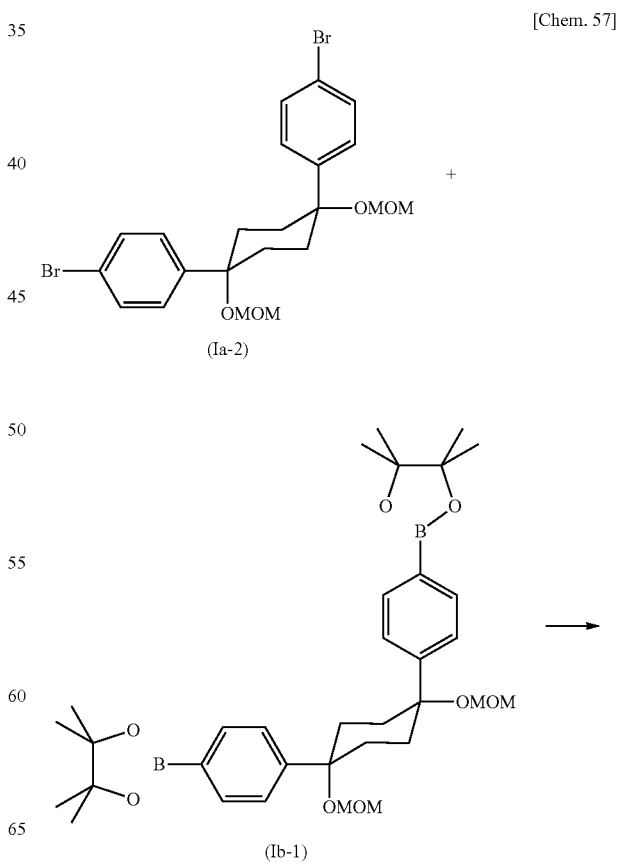

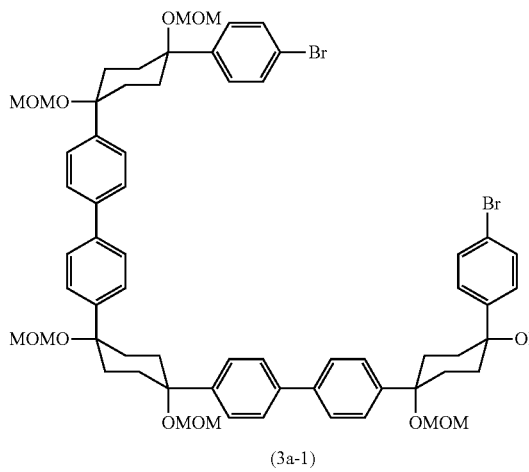

(3a-1)

In the formula, MOM represents a methoxymethyl group.

To a 200-mL round-bottom glass flask containing a stirring bar were added Compound (Ia-2) (5.58 g, 10.9 mmol) obtained in Synthesis Example 2, Compound (Ib-1) (608 mg, 1.00 mmol) obtained in Synthesis Example 3, tetrakis(triphenylphosphine)palladium(0) (Pd(PPh$_3$)$_4$) (114 mg, 98.2 µmol), silver carbonate (Ag$_2$CO$_3$) (983 mg, 3.57 mmol), and dry THF (100 mL). The resulting mixture was reacted under reflux for 38 hours while stirring. After being cooled to room temperature, the reaction mixture was quenched with water. The resulting product was extracted with ethyl acetate (EtOAc), and the organic phase was dried over Na$_2$SO$_4$ and concentrated under reduced pressure. The crude product was purified by silica gel column chromatography (hexane/EtOAc=5/1 to 1/1) to yield the target compound as a colorless solid (789 mg) (yield: 65%).

$^1$H NMR (600 MHz, CDCl$_3$) δ2.11(brs, 12H), 2.28-2.43 (m, 12H), 3.40 (s, 6H), 3.42 (s, 6H), 3.43 (s, 6H), 4.43 (s, 4H), 4.46 (s, 4H), 4.48 (s, 4H), 7.31 (d, J=8 Hz, 4H), 7.43 (d, J=8 Hz, 4H), 7.47-7.57 (m, 16H); $^{13}$C NMR (150 MHz, CDCl$_3$) δ32.8 (CH$_2$), 55.9 (CH$_3$), 77.8 (4°), 77.9 (4°), 78.0 (4°), 92.0 (CH$_2$), 92.1 (CH$_2$), 121.5 (4°), 126.8 (CH), 126.8 (CH), 127.2 (CH), 128.6 (CH), 131.4 (CH), 139.4 (4°), 139.5 (4°), 141.5 (br, 4°); HRMS (FAB) m/z calcd for C$_{66}$H$_{78}$Br$_2$NaO$_{12}$ [M·Na]$^+$: 1243.3752, found: 1243.3760

When the same procedure was performed as described above, except that the reaction conditions were changed to 60° C. and 24 hours, the yield was 59%.

Synthesis Example 5

Compound (5a-1)

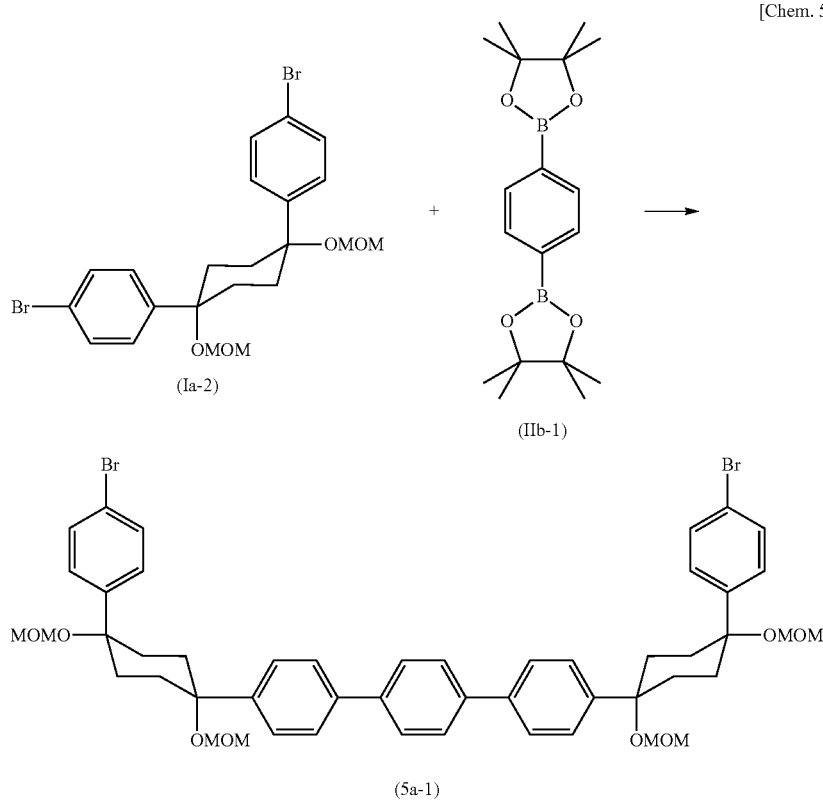

[Chem. 58]

In the formula, MOM represents a methoxymethyl group.

To a 200-mL round-bottom flask containing a stirring bar were added cesium fluoride (400 mg, 2.6 mmol), Compound (Ia-2) (2.07 g, 4 mmol) obtained in Synthesis Example 2, Compound (IIb-1) (1,4-benzenediboronic acid bis(pinacol) ester) (151.2 mg, 0.5 mmol), and tetrakis(triphenylphosphine)palladium(0) (Pd(PPh$_3$)$_4$) (30.1 mg, 0.026 mmol); and argon gas was introduced into the flask. Dry THF (60 mL) was added thereto, and the resulting mixture was reacted at 65° C. for 26 hours while stirring. The mixture (reaction liquid) in the flask was then cooled to room temperature, and passed through Celite. After the solvent was distilled off from the filtrate under reduced pressure using an evaporator, the residue (concentrate) was purified by silica gel chromatography (hexane/EtOAc) to yield the target compound as a white solid (319.9 mg) (yield: 68%).

$^1$H NMR (400 MHz, CDCl$_3$) δ 2.11 (brs, 8H), 2.30-2.40 (brm, 8H), 3.42 (s, 6H), 3.43 (s, 6H), 4.44 (s, 4H), 4.48 (s, 4H), 7.33 (d, J=9 Hz, 4H), 7.45 (d, J=9 Hz, 4H), 7.51 (d, J=9 Hz, 4H), 7.60 (d, J=9 Hz, 4H), 7.65 (s, 4H); $^{13}$C NMR (100 MHz, CDCl$_3$) δ 33.0 (CH$_2$), 56.0 (CH$_3$), 77.9 (4°), 78.1 (4°), 92.2 (CH$_2$), 92.3 (CH$_2$), 121.7 (4°), 126.9 (CH), 127.4 (CH), 128.7 (4°), 131.5 (CH), 139.5 (4°), 139.8) (4°); HRMS (FAB) m/z calcd for C$_{50}$H$_{56}$Br$_2$O$_8$Na [M$^+$Na]$^+$: 965.2240, found 965.2195; mp: 184.7-186.4° C.

Synthesis Example 6

Compound (5a-2)

In the formula, MOM represents a methoxymethyl group.

To a 50-mL round-bottom flask containing a stirring bar were added Compound (5a-1) (285.4 mg, 0.30 mmol) obtained in Synthesis Example 5, tris(dibenzylideneacetone)dipalladium(0) (Pd$_2$(dba)$_3$) (6.0 mg, 6.6 μmol), 2-(dicyclohexylphosphino)-2',4',6'-tri-isopropyl-1,1'-biphenyl (X-Phos) (13.3 mg, 28 μmol), bis(pinacolate)diboron (227.5 mg, 0.9 mmol), and potassium acetate (KOAc) (180.1 mg, 1.8 mmol); and argon gas was introduced into the flask. Dry dioxane (1,4-dioxane) (15 mL) was added thereto, and the resulting mixture was reacted at 90° C. for 5 hours while stirring. The resulting mixture (reaction liquid) in the flask was cooled to room temperature, and passed through silica gel. After the solvent was distilled off from the filtrate under reduced pressure using an evaporator, the residue (concentrate) was purified by gel permeation chromatography (chloroform) to yield the target compound as a white solid (271.7 mg) (yield: 87%).

$^1$H NMR (400 MHz, CDCl$_3$) δ 1.32 (s, 24H) 2.14 (brs, 8H), 2.36 (brs, 8H), 3.41 (s, 6H), 3.43 (s, 6H), 4.43 (s, 4H), 4.48 (s, 4H), 7.46 (d, J=8 Hz, 2H), 7.49 (d, J=9 Hz, 2H), 7.45 (6, J=9 Hz, 4H), 7.51 (d, J=8 Hz, 4H), 7.60 (d, J=8.5 Hz, 4H), 7.65 (s, 4H); $^{13}$C NMR (100 MHz, CDCl$_3$) δ 24.9 (CH$_3$), 33.0 (CH$_2$), 56.0 (CH$_3$), 78.2 (4°), 78.3 (4°), 83.8 (4°), 92.2 (CH$_2$), 92.3 (CH$_2$), 126.2) (4°), 126.9 (CH), 127.4 (CH), 134.8 (4°), 134.9

[Chem. 59]

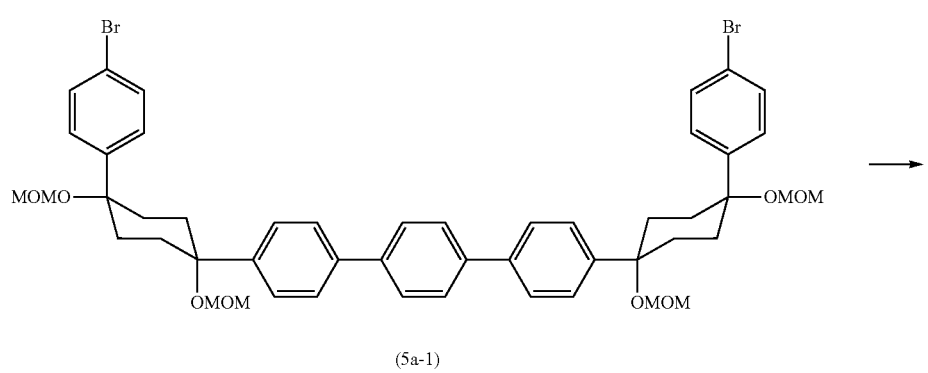

(5a-1)

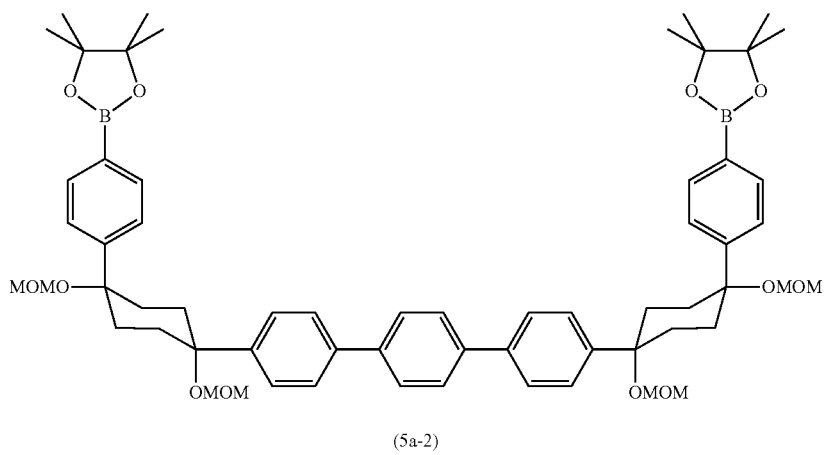

(5a-2)

(CH), 139.5 (4°), 139.7 (4°); HRMS (FAB) m/z calcd for C$_{62}$H$_{80}$B$_2$O$_{12}$Na [M·Na]$^+$: 1061.5753, found 1061.5719; mp: 225.1-226.6° C.

Synthesis Example 7

Compound (6a)

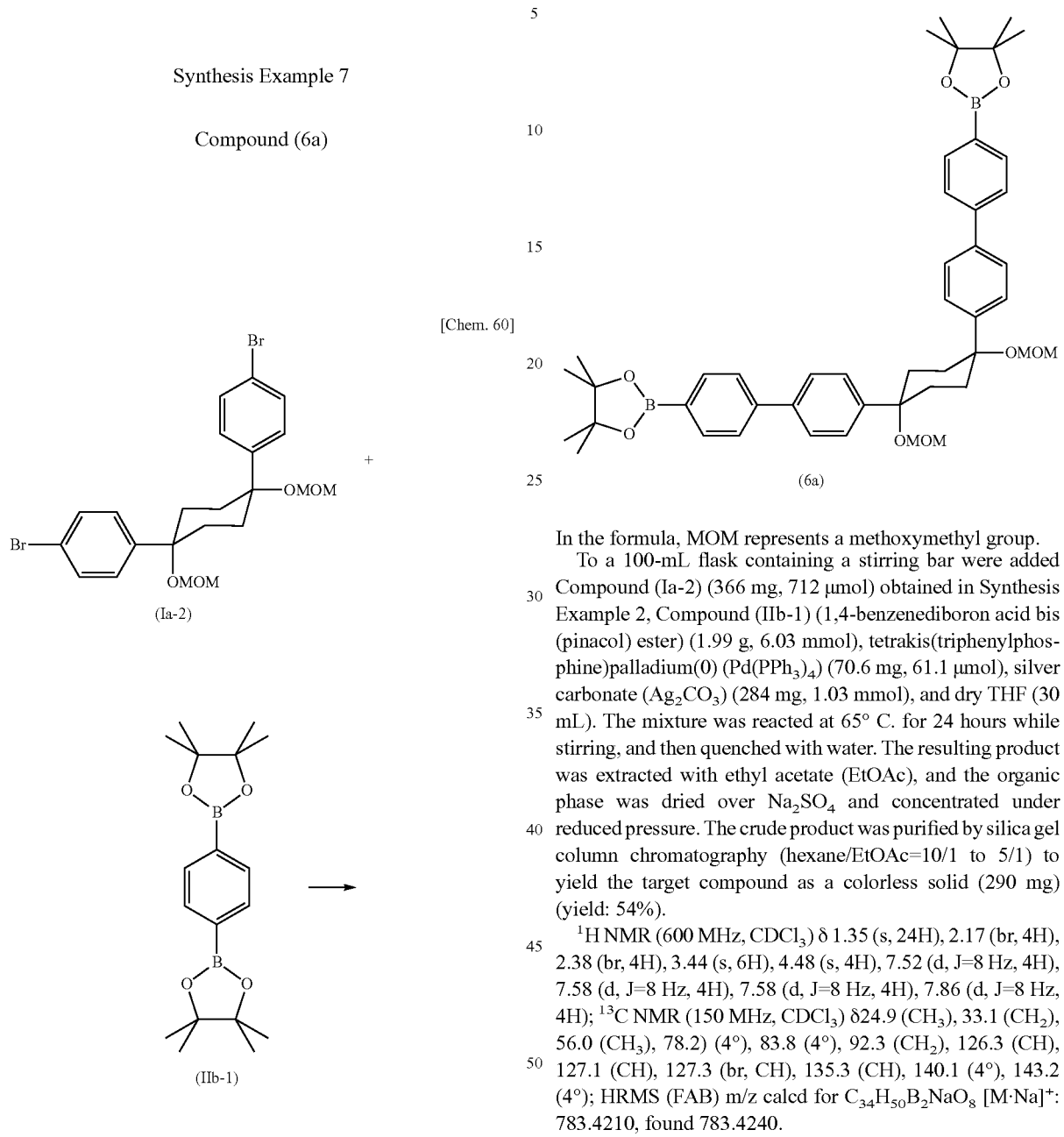

[Chem. 60]

In the formula, MOM represents a methoxymethyl group.

To a 100-mL flask containing a stirring bar were added Compound (Ia-2) (366 mg, 712 µmol) obtained in Synthesis Example 2, Compound (IIb-1) (1,4-benzenediboron acid bis(pinacol) ester) (1.99 g, 6.03 mmol), tetrakis(triphenylphosphine)palladium(0) (Pd(PPh$_3$)$_4$) (70.6 mg, 61.1 µmol), silver carbonate (Ag$_2$CO$_3$) (284 mg, 1.03 mmol), and dry THF (30 mL). The mixture was reacted at 65° C. for 24 hours while stirring, and then quenched with water. The resulting product was extracted with ethyl acetate (EtOAc), and the organic phase was dried over Na$_2$SO$_4$ and concentrated under reduced pressure. The crude product was purified by silica gel column chromatography (hexane/EtOAc=10/1 to 5/1) to yield the target compound as a colorless solid (290 mg) (yield: 54%).

$^1$H NMR (600 MHz, CDCl$_3$) δ 1.35 (s, 24H), 2.17 (br, 4H), 2.38 (br, 4H), 3.44 (s, 6H), 4.48 (s, 4H), 7.52 (d, J=8 Hz, 4H), 7.58 (d, J=8 Hz, 4H), 7.58 (d, J=8 Hz, 4H), 7.86 (d, J=8 Hz, 4H); $^{13}$C NMR (150 MHz, CDCl$_3$) δ24.9 (CH$_3$), 33.1 (CH$_2$), 56.0 (CH$_3$), 78.2 (4°), 83.8 (4°), 92.3 (CH$_2$), 126.3 (CH), 127.1 (CH), 127.3 (br, CH), 135.3 (CH), 140.1 (4°), 143.2 (4°); HRMS (FAB) m/z calcd for C$_{34}$H$_{50}$B$_2$NaO$_8$ [M·Na]$^+$: 783.4210, found 783.4240.

Synthesis Example 8
Compound (7)
[Chem. 61]
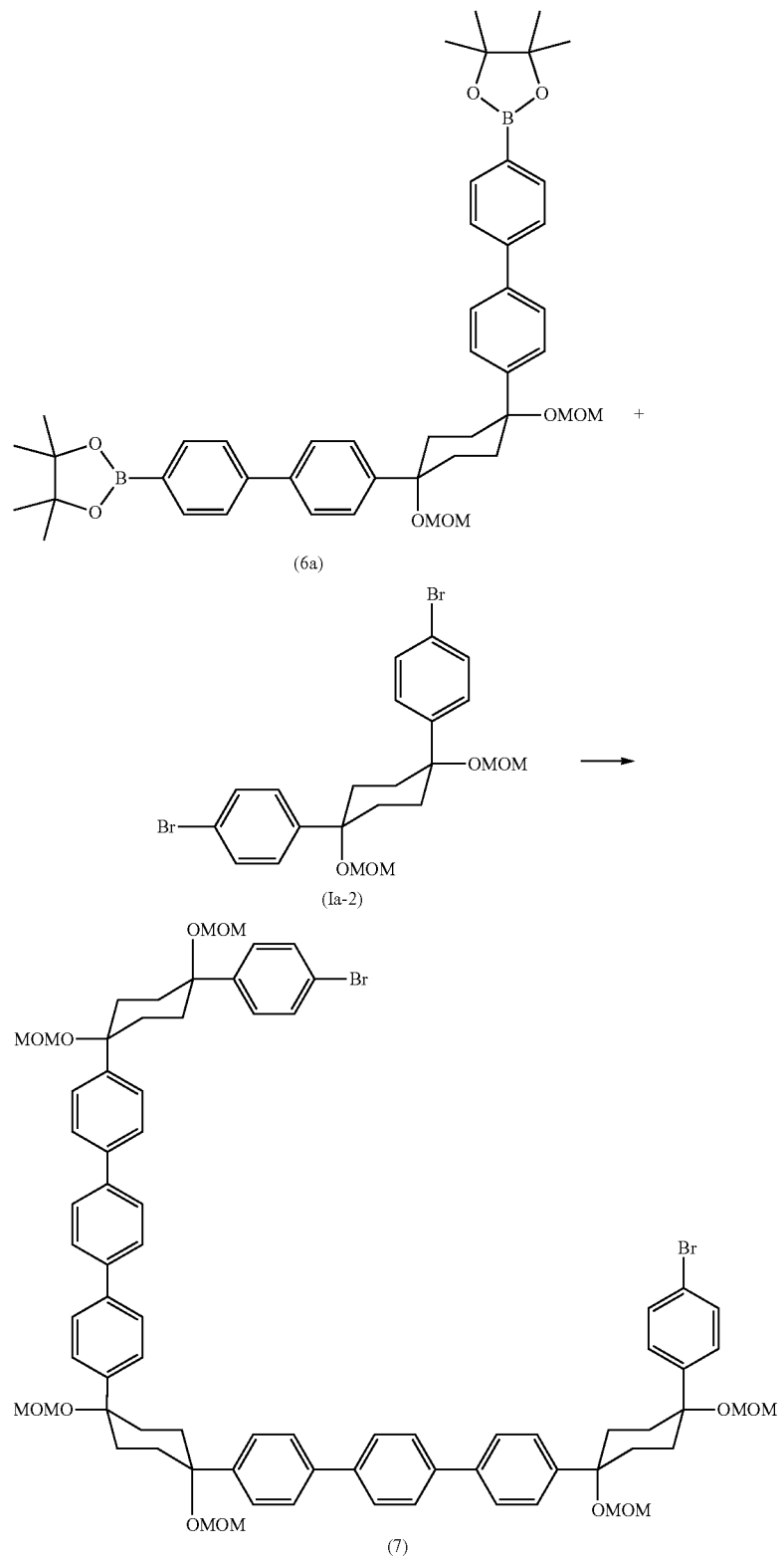

In the formula, MOM represents a methoxymethyl group.

To a 100-mL flask containing a stirring bar were added Compound (6a) (155 mg, 204 μmol) obtained in Synthesis Example 7, Compound (Ia-2) (1.22 g, 2.37 mmol) obtained in Synthesis Example 2, tetrakis(triphenylphosphine)palladium (0) (Pd(PPh$_3$)$_4$) (25.4 mg, 22.0 mmol), sodium carbonate (Na$_2$CO$_3$) (107 mg, 1.01 mmol), dry toluene (12 mL), and dry ethyl acetate (EtOAc) (3 mL). The resulting mixture was reacted at 70° C. for 24 hours while stirring. After being cooled to room temperature, the mixture was concentrated under reduced pressure. The resulting product was extracted with ethyl acetate (EtOAc), dried over Na$_2$SO$_4$, and concentrated under reduced pressure. The crude product was purified by silica gel column chromatography (hexane/EtOAc=6/1 to 1/1) to yield the target compound as a colorless solid (239 mg) (yield: 44%).

$^1$H-NMR (600 MHz, CDCl$_3$) δ2.10 (br, 12H), 2.27-2.49 (m, 12H), 3.41 (s, 6H), 3.43 (s, 6H), 3.45 (s, 6H), 4.43 (s, 4H), 4.47 (s, 4H), 4.50 (s, 4H), 7.32 (d, J=8 Hz, 4H), 7.44 (d, J=8 Hz, 4H), 7.50 (d, J=8 Hz, 4H), 7.54 (d, J=8 Hz, 4H), 7.59 (d, J=8 Hz, 4H), 7.60 (d, J=8 Hz, 4H), 7.64 (s, 8H); $^{13}$C NMR (150 MHz, CDCl$_3$) δ 33.0 (CH$_2$), 56.0 (CH$_3$), 77.9 (4°), 78.1 (4°), 78.2 (4°), 92.2 (CH$_2$), 92.3 (CH$_2$), 121.7 (4°), 126.9 (CH), 126.9 (CH), 127.4 (CH), 127.4 (CH), 128.7 (CH), 131.5 (CH), 139.4 (4°), 139.5 (4°), 139.7 (4°), 139.8 (4°), 141.6 (br,) 4°; HRMS (FAB) m/z calcd for C$_{76}$H$_{86}$Br$_2$NaO$_8$ [M·Na]$^+$: 1395.4378, found 1395.4364.

Synthesis Example 9

Compound (4a)

[Chem. 62]

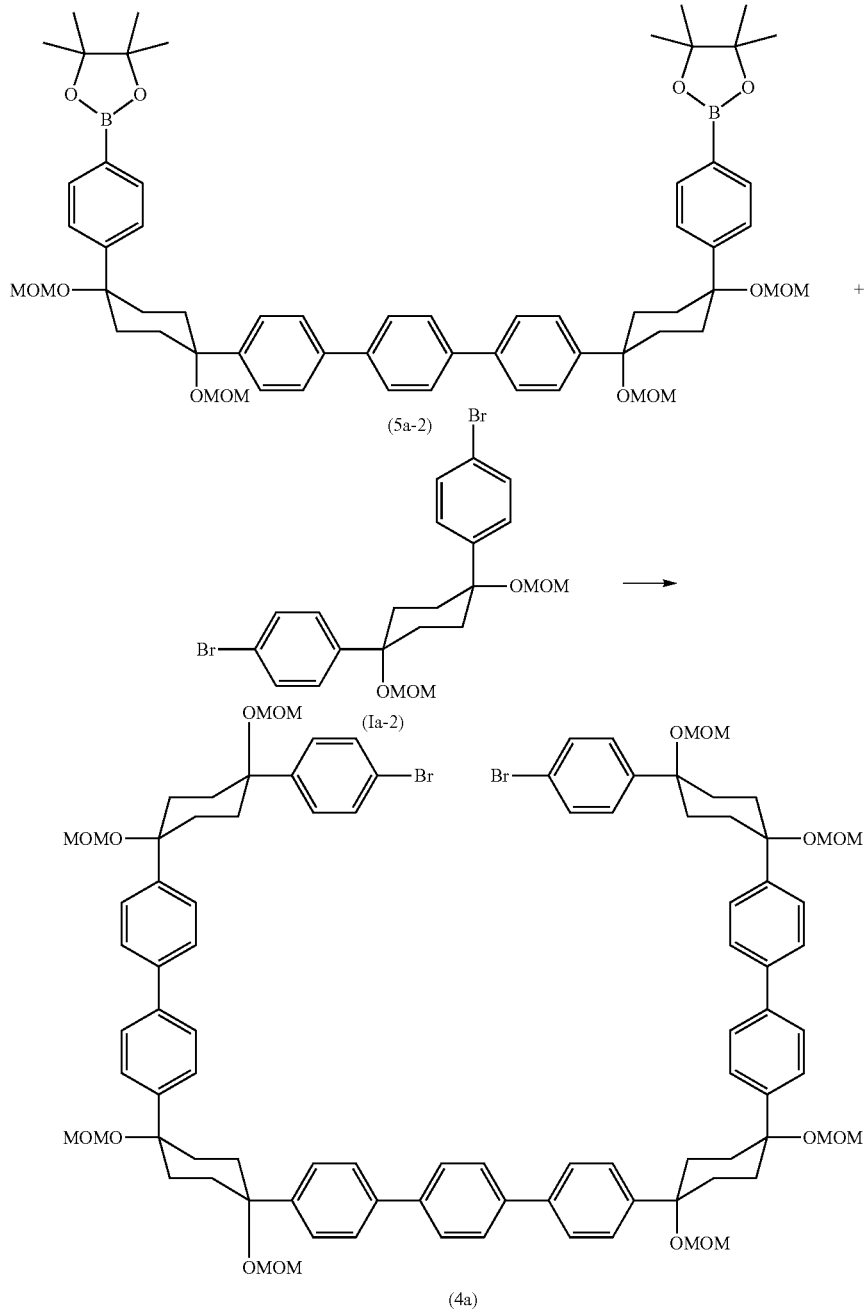

In the formula, MOM represents a methoxymethyl group.

To a 50-mL round-bottom glass flask containing a stirring bar were added Compound (5a-2) (102 mg, 98.2 µmol) obtained in Synthesis Example 6, Compound (Ia-2) (500 mg, 972 µmol) obtained in Synthesis Example 2, tetrakis(triphenylphosphine)palladium(0) (Pd(PPh$_3$)$_4$) (11.1 mg, 9.60 µmol), silver carbonate (Ag$_3$CO$_3$) (108 mg, 355 µmol), and dry THF (10 mL). The resulting mixture was reacted at 60° C. for 19 hours while stirring. After being cooled to room temperature, the reaction mixture was quenched with water. Subsequently, extraction was performed with ethyl acetate (EtOAc), and the organic phase was dried over Na$_2$SO$_4$ and concentrated under reduced pressure. The crude product was purified by silica gel column chromatography (hexane/EtOAc=3/1 to 2/3) to yield the target compound as a colorless solid (93.9 mg) (yield: 58%).

$^1$H NMR (600 MHz, CDCl$_3$) β2.15 (br, 16H), 2.27-2.42 (m, 16H), 3.40 (s, 6H), 3.41 (s, 6H), 3.43 (s, 6H), 3.44 (s, 6H), 4.43 (s, 4H), 4.45 (s, 4H), 4.47 (s, 4H), 4.49 (s, 4H), 7.31 (d, J=8 Hz, 4H), 7.43 (d, J=8 Hz, 4H), 7.45-7.56 (m, 20H), 7.59 (d, J=8 Hz, 4H), 7.63 (s, 4H); HRMS (FAB) m/z calcd for C$_{94}$H$_{108}$Br$_2$NaO$_{16}$[M·Na]$^+$: 1673.5896, found 1673.5862.

Example 1

Compound (a1-1)

[Chem. 63]

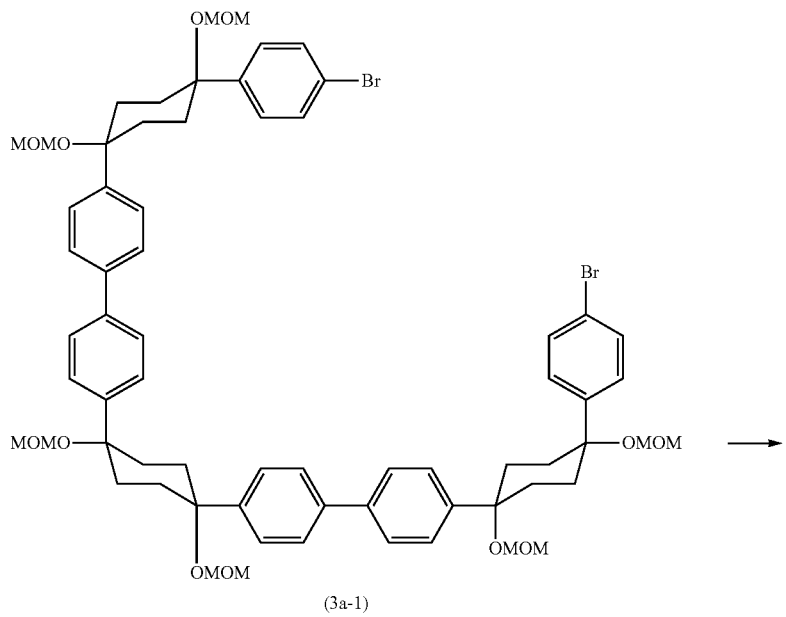

(3a-1)

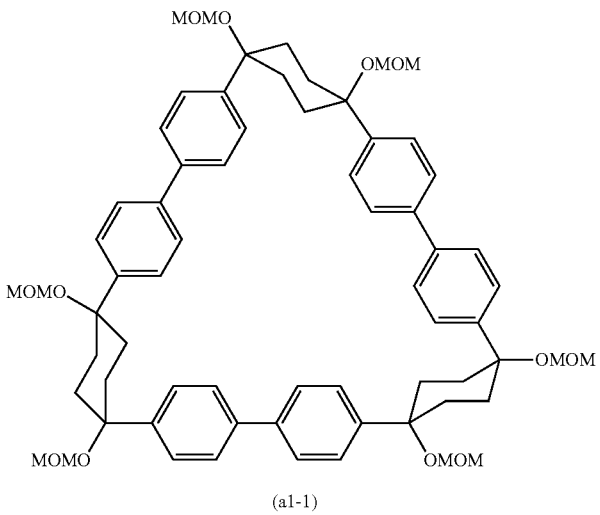

(a1-1)

In the formula, MOM represents a methoxymethyl group.

To a 50-mL round-bottom glass flask containing a stirring bar were added bis(1,5-cyclooctadiene)nickel(0) (Ni(cod)$_2$) (14.5 mg, 52.7 µmol), Compound (3a-1) (30.6 mg, 25.0 µmol) obtained in Synthesis Example 4, and 2,2'-bipyridyl (7.82 mg, 50.1 µmol). Dry THF (15.5 mL) was then further added thereto. The resulting mixture was reacted under reflux for 24 hours while stirring. After being cooled to room temperature, the reaction mixture was filtered through silica gel and washed with ethyl acetate (EtOAc), and the solvent was then removed under reduced pressure. The crude product was purified by silica gel column chromatography (hexane/EtOAc) to yield the target compound as a colorless solid (12.2 mg) (yield: 46%).

$^1$H NMR (600 MHz, 50° C., CDCl$_3$) δ 2.07 (br, 12H), 2.28-2.34 (m, 12H), 3.43 (s, 18H), 4.58 (s, 12H), 7.40 (d, J=8 Hz, 12H), 7.46 (d, J=8 Hz, 12H); $^{13}$C NMR (150 MHz, 50° C., CDCl$_3$) δ 33.3 (CH$_3$), 55.9 (CH$_3$), 78.1 (4°), 92.4 (CH$_2$), 126.8 (CH), 127.3 (CH), 139.4 (4°), 141.2 (4°); HRMS (FAB) m/z calcd for C$_{66}$H$_{78}$NaO$_{12}$ [M·Na]$^+$: 1085.5391, found: 1085.538; mp: 182.3-187.0° C.

Example 2

Compound (a4-1) Part 1

[Chem. 64]

In the formula, MOM represents a methoxymethyl group.

To a 50-mL round-bottom glass flask containing a stirring bar were added Compound (Ia-2) (21.0 mg, 40.9 µmol) obtained in Synthesis Example 2, Compound (5a-2) (49.4 mg, 47.6 µmol) obtained in Synthesis Example 6, tris(dibenzylideneacetone)dipalladium(0) (Pd$_2$(dba)$_3$) (3.8 mg, 8.0 µmol), potassium phosphate (K$_3$PO$_4$) (84.9 mg, 405 µmol), 1,4-dioxane (20 mL), and water (80 µL). The resulting mixture was reacted at 80° C. for 24 hours while stirring. After being cooled to room temperature, the reaction mixture was filtered through silica gel and washed with ethyl acetate (EtOAc). The solvent was then removed under reduced pressure. The crude product was purified by silica gel column chromatography (chloroform) and preparative thin-layer chromatography (CHCl₃/EtOAc=1/1) to yield the target compound as a colorless solid (9.3 mg) (yield: 20%).

¹H-NMR (600 MHz, CD₂Cl₂, 35° C.) δ 1.67 (s, 4H), 1.93-2.53 (m, 20H), 2.31 (br, 4H), 3.36 (s, 6H), 3.37 (s, 6H), 3.45 (s, 6H), 4.48 (s, 4H), 4.55 (s, 4H), 4.58 (s, 4H), 7.29 (d, J=8 Hz, 4H), 7.40-7.47 (m, 12H), 7.60 (d, J=8 Hz, 4H), 7.66 (d, J=8 Hz, 4H), 7.68 (s, 4H); ¹³C NMR (150 MHz, CDCl₃, 50° C.) δ 32.8 (CH₂), 33.2 (CH₂), 34.0 (CH₂), 55.5 (CH₃), 55.9 (CH₃), 56.2 (CH₃), 77.9) (4°), 78.3 (4°), 78.4 (4°), 92.2 (CH₂), 92.3 (CH₂), 92.6 (CH₂), 126.6 (CH), 126.8 (CH), 126.8 (CH), 127.2 (CH), 127.3 (CH), 128.3 (CH), 139.3 (4°), 139.3 (4°), 139.5 (4°), 139.5 (4°); HRMS (FAB) m/z calcd for C₃₄H₅₀B₂NaO₈ [M·Na]⁺: 631.3584, found 631.3605.

Example 3

Compound (a4-1) Part 2

[Chem. 65]

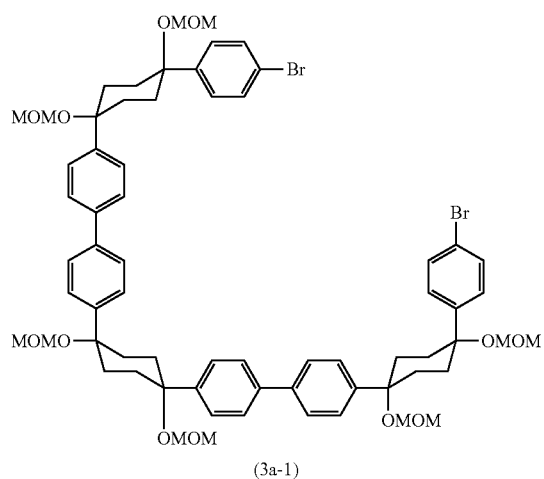
(3a-1)

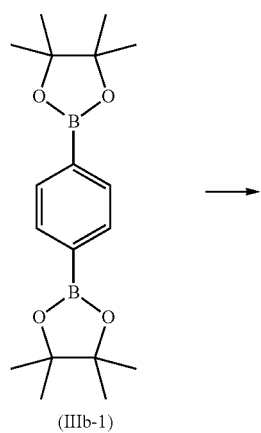
(IIIb-1)

-continued

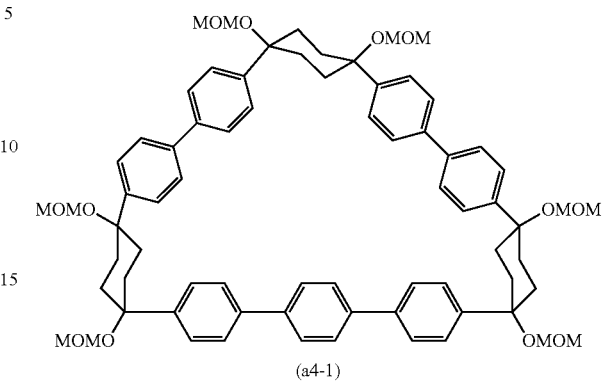
(a4-1)

In the formula, MOM represents a methoxymethyl group.

To a 50-mL Schlenk flask containing a stirring bar were added Compound (3a-1) (29.5 mg, 24.1 μmol) obtained in Synthesis Example 4, Compound (IIb-1) (1,4-benzenediboron acid bis(pinacol) ester) (11.1 mg, 33.6 μmol), palladium acetate (II) (Pd(OAc)₂) (2.15 mg, 9.58 μmol), 2-(dicyclohexylphosphino)-2',4',6'-triisoporopoyl-1,1'-biphenyl (X-Phos) (4.57 mg, 9.59 μmol), 10 M NaOH aqueous solution (20.0 mL, 200 μmol), and 1,4-dioxane (20 mL). The resulting mixture was reacted at 80° C. for 17 hours while stirring. Water was further added thereto, and extraction was performed with ethyl acetate (EtOAc). The organic phase was dried over Na₂SO₄, and concentrated under reduced pressure. The crude product was purified by silica gel column chromatography (chloroform) and preparative thin-layer chromatography (CHCl₃/EtOAc=1/1) to yield the target compound as a colorless solid (5.04 mg) (yield: 18%).

¹H NMR (600 MHz, CD₂Cl₂, 35° C.) δ 1.67 (s, 4H), 1.93-2.53 (m, 20H), 2.31 (br, 4H), 3.36 (s, 6H), 3.37 (s, 6H), 3.45 (s, 6H), 4.48 (s, 4H), 4.55 (s, 4H), 4.58 (s, 4H), 7.29 (d, J=8 Hz, 4H), 7.40-7.47 (m, 12H), 7.60 (d, J=8 Hz, 4H), 7.66 (d, J=8 Hz, 4H), 7.68 (s, 4H); ¹³C NMR (150 MHz, CDCl₃, 50° C.) δ 32.8 (CH₂), 33.2 (CH₂), 34.0 (CH₂), 55.5 (CH₃), 55.9 (CH₃), 56.2 (CH₃), 77.9) (4°), 78.3 (4°), 78.4 (4°), 92.2 (CH₂), 92.3 (CH₂), 92.6 (CH₂), 126.6 (CH), 126.8 (CH), 126.8 (CH), 127.2 (CH), 127.3 (CH), 128.3 (CH), 139.3 (4°), 139.3 (4°), 139.5 (4°), 139.5 (4°); HRMS (FAB) m/z calcd for C₃₄H₅₀B₂NaO₈ [·Na]⁺: 631.3584, found 631.3605.

Example 4

Compound (a3-1)

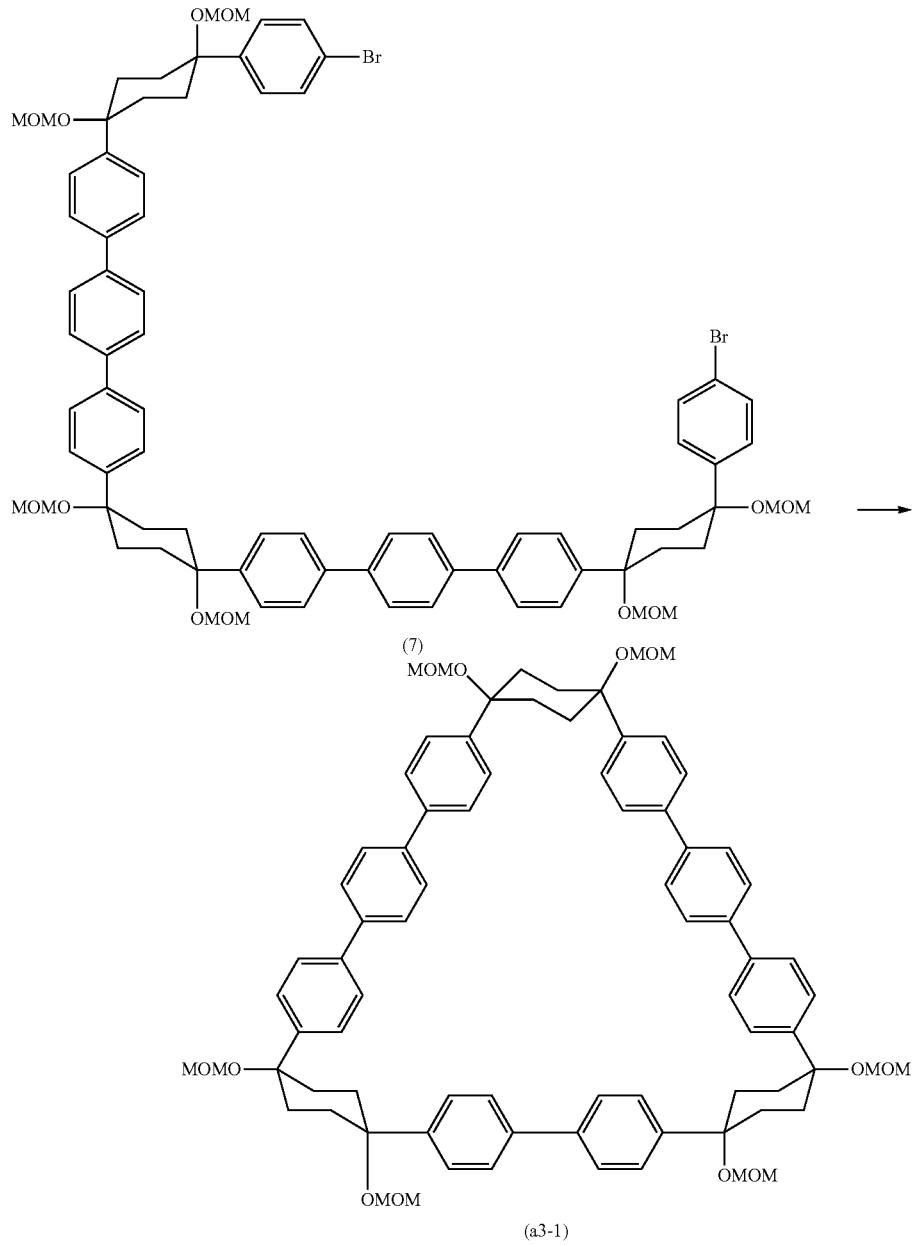

[Chem. 66]

In the formula, MOM represents a methoxymethyl group.

To a 20-mL J-Young Schlenk flask containing a stirring bar were added Compound (7) (70.0 mg, 50.9 μmol) obtained in Synthesis Example 8, bis(1,5-cyclooctadiene)nickel(0) (Ni(cod)$_2$) (48.2 mg, 17.5 μmol), 2,2'-bipyridyl (27.1 mg, 17.3 μmol), and dry 1,4-dioxane (2 mL). The resulting mixture was reacted at 80° C. for 24 hours while stirring. After being cooled to room temperature, the mixture was concentrated under reduced pressure. The resulting product was extracted with ethyl acetate (EtOAc), dried over Na$_2$SO$_4$, and concentrated under reduced pressure. The crude product was purified by silica gel column chromatography (CHCl$_3$/EtOAc=2/1) to yield the target compound as a colorless solid (26.1 mg) (yield: 42%).

$^1$H NMR (600 MHz, CDCl$_3$, 50° C.) δ 1.86 (br, 4H), 2.08 (br, 4H), 2.21-2.47 (m, 16H), 3.39 (s, 6H), 3.44 (s, 6H), 3.44 (s, 6H), 4.52 (s, 4H), 4.54 (s, 4H), 4.62 (s, 4H), 7.35 (d, J=8 Hz, 4H), 7.42 (d, J=8 Hz, 4H), 7.44 (d, J=8 Hz, 4H), 7.54 (d, J=8 Hz, 8H), 7.56-7.62 (m, 16H); $^{13}$C NMR (150 MHz, CDCl$_3$, 50° C.) δ 32.8 (CH$_2$), 33.4 (CH$_2$), 33.7 (CH$_2$), 55.7 (CH$_3$), 55.8 (CH$_3$), 56.2 (CH$_3$), 77.9 (4°), 78.0 (4°), 78.3 (4°), 92.2 (CH$_2$), 92.4 (CH$_2$), 92.5 (CH$_2$), 126.8 (CH), 126.8 (CH), 126.8 (CH), 126.9 (CH), 127.2 (CH), 127.3 (CH), 127.5 (CH), 127.9 (CH), 139.2 (4°), 139.3 (4°), 139.4 (4°), 139.5 (4°), 139.6 (4°); HRMS (FAB) m/z calcd for C$_{76}$H$_{86}$NaO$_8$ [M·Na]$^+$: 1237.6011, found 1237.6014.

Example 5

Compound (a2-1)

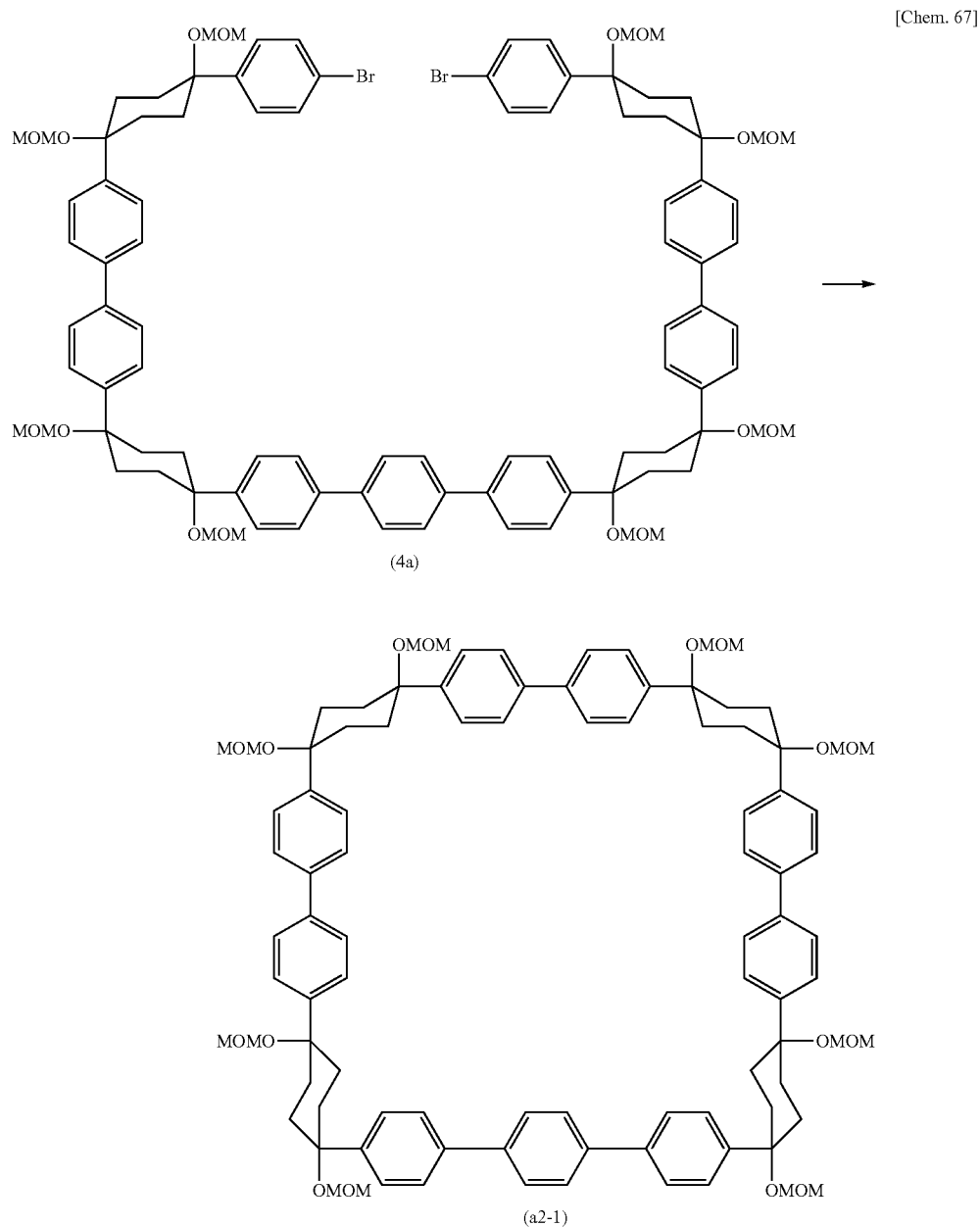

In the formula, MOM represents a methoxymethyl group.

To a 50-mL round-bottom glass flask containing a stirring bar were added Compound (4a) (41.3 mg, 25.0 μmol) obtained in Synthesis Example 9, bis(1,5-cyclooctadiene) nickel (0) (Ni(cod)$_2$) (13.8 mg, 50.2 μmol), and 2,2'-bipyridyl. Dry THF (12.5 mL) was added thereto, and the resulting mixture was reacted under reflux for 24 hours while stirring. After being cooled to room temperature, the reaction mixture was filtered through silica gel and washed with ethyl acetate (EtOAc). The solvent was then removed under reduced pressure. The crude product was purified by silica gel column chromatography (hexane/EtOAc) to yield the target compound as a colorless solid (19.0 mg) (yield: 51%).

$^1$H NMR (600 MHz, CDCl$_3$, 50° C.) δ 1.90-2.46 (m, 32H), 3.38 (s, 6H), 3.40 (s, 6H), 3.40 (s, 6H), 3.45 (s, 6H), 4.40 (s, 4H), 4.42 (s, 4H), 4.50 (s, 4H), 4.52 (s, 4H), 7.42 (d, J=8 Hz, 4H), 7.45-7.52 (m, 20H), 7.55 (d, J=8 Hz, 4H), 7.59 (d, J=8 Hz, 4H), 7.63 (s, 4H); HRMS (FAB) m/z calcd for C$_{94}$H$_{108}$NaO$_8$[M·Na]$^+$: 1515.7535, found 1515.7530.

Example 6

[9]Cycloparaphenylene

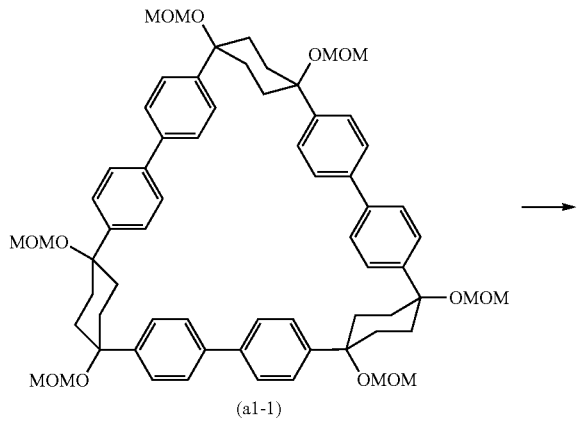

(a1-1)

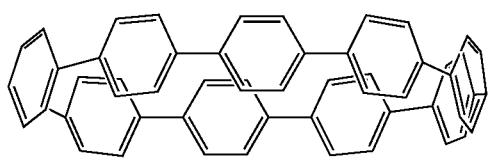

In the formula, MOM represents a methoxymethyl group.

To a 20-mL Schlenk flask containing a stirring bar and a condenser were added Compound (a1-1) (26.6 mg, 25 µmol) obtained in Example 1, sodium hydrogen sulfate monohydrate (NaHSO$_4$.H$_2$O) (69.1 mg, 400 µmol), dry dimethylsulfoxide (DMSO) (1.5 mL), and dry m-xylene (5 mL). The flask was heated at 150° C. for 48 hours while stirring. After being cooled to room temperature, the mixture (reaction liquid) was extracted with CHCl$_3$ and dried over Na$_2$SO$_4$. The solvent was then distilled off under reduced pressure to yield a crude product. Thereafter, TLC (CH$_2$Cl$_2$/hexane) was performed to isolate the target compound as a yellow solid (4.2 mg) (yield: 24%).

$^1$HNMR (600 MHz, CDCl$_3$) δ 7.52 (s, 36H); $^{13}$C NMR (150 MHz, CDCl$_3$) δ 127.3 (CH), 137.9 (4°); HRMS (MALDI-TOF) m/z calcd for C$_{54}$H$_{36}$ [M·]$^+$: 684.2817, found: 684.2834.

Example 7

[10]Cycloparaphenylene

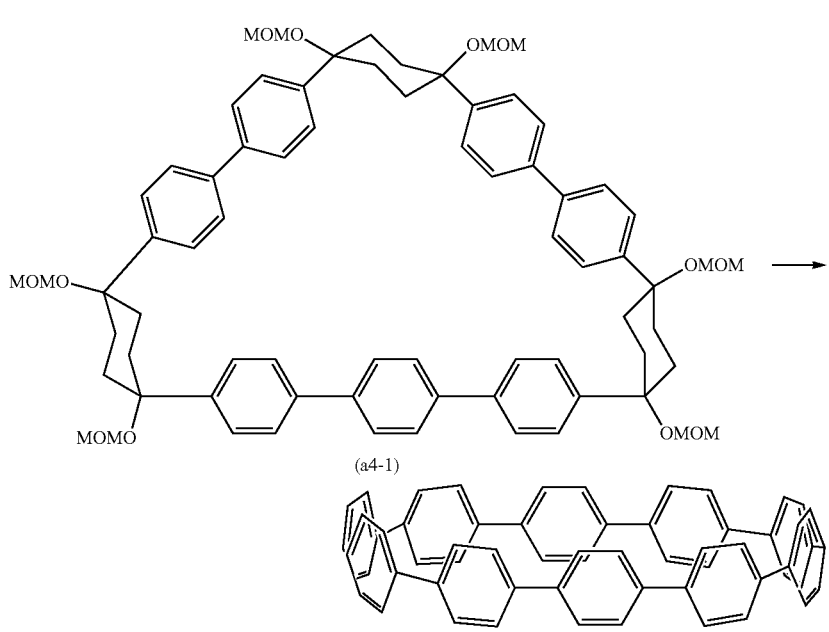

(a4-1)

In the formula, MOM represents a methoxymethyl group.

To a 20-mL Schlenk flask containing a stirring bar and a condenser were added Compound (a4-1) (9.3 mg, 8.2 µmol) obtained in Example 2 or 3, sodium hydrogen sulfate monohydrate (NaHSO$_4$.H$_2$O) (28 mg, 20 µmol), dry dimethylsulfoxide (DMSO) (1.5 mL), and dry m-xylene (5 mL), and the flask was heated at 150° C. for 72 hours while stirring. After being cooled to room temperature, the resulting mixture was quenched with a saturated sodium hydrogen carbonate (NaHCO$_3$) aqueous solution. Filtration was then performed through Celite using ethyl acetate (EtOAc) as a solvent, followed by extraction with ethyl acetate (EtOAc). The organic phase was dried over Na$_2$SO$_4$, and concentrated under reduced pressure. Thereafter, TLC (hexane/CH$_2$Cl$_2$=1/1) was performed to yield the target compound as a yellow solid (1.5 mg) (yield: 24%).

$^1$H NMR (600 MHz, CDCl$_3$) δ 7.56 (s, 40H); $^{13}$C NMR (150 MHz, CDCl$_3$) δ 127.4 (CH), 138.2 (4°); HRMS (MALDI) m/z calcd for C$_{60}$H$_{40}$ [M·]$^+$: 760.3125, found: 760.3153.

Example 8

[11]Cycloparaphenylene

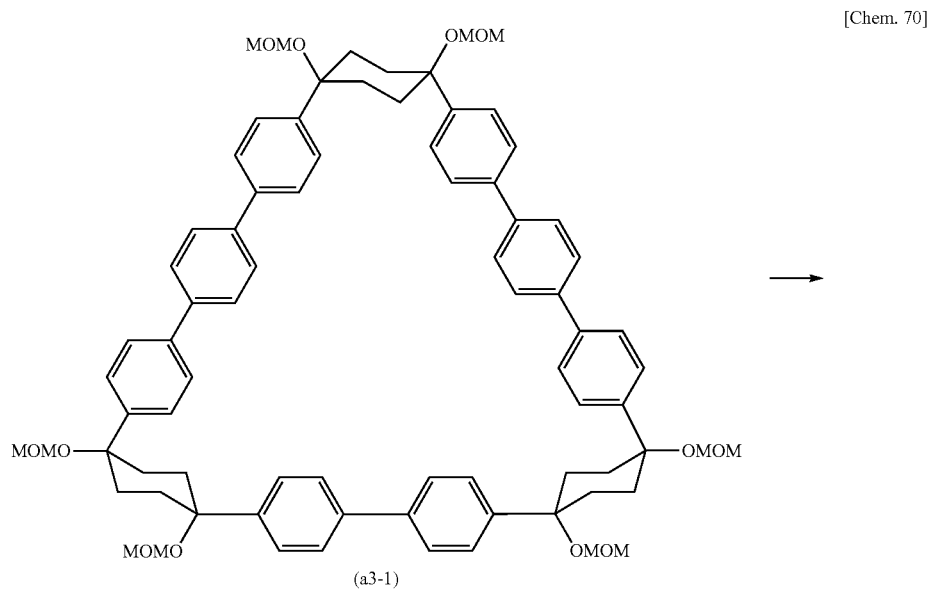

(a3-1)

In the formula, MOM represents a methoxymethyl group.

To a 20-mL Schlenk flask containing a stirring bar and a condenser were added Compound (a3-1) (20.7 mg, 17.0 μmol) obtained in Example 4, sodium hydrogen sulfate monohydrate (NaHSO$_4$.H$_2$O) (51.6 mg, 37.4 μmol), o-chloranil (20.7 mg, 84.2 μmol), dry dimethylsulfoxide (DMSO) (1.5 mL), and dry m-xylene (4 mL). The flask was heated at 150° C. for 48 hours while stirring. After being cooled to room temperature, the resulting mixture was quenched with a saturated sodium hydrogen carbonate (NaHCO$_3$) aqueous solution, and filtration was performed through Celite using ethyl acetate (EtOAc) as a solvent. The resulting product was extracted with ethyl acetate (EtOAc), and the organic phase was dried over Na$_2$SO$_4$ and concentrated under reduced pressure. Subsequently, TLC (hexane/CH$_2$Cl$_2$=1/1) was per-

[Chem. 70]

→

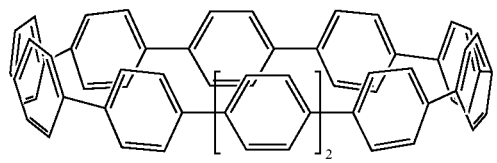

formed to yield the target compound as a yellow solid (4.6 mg) (yield: 32%).

$^1$H NMR (600 MHz, CDCl$_3$) δ 7.58 (s, 44H); $^{13}$C NMR (150 MHz, CDCl$_3$) δ 127.3 (CH), 138.4 (4°); HRMS (MALDI) m/z calcd for C$_{66}$H$_{44}$ [M·]$^+$: 836.3438, found: 836.3437.

Example 9

[13]Cycloparaphenylene

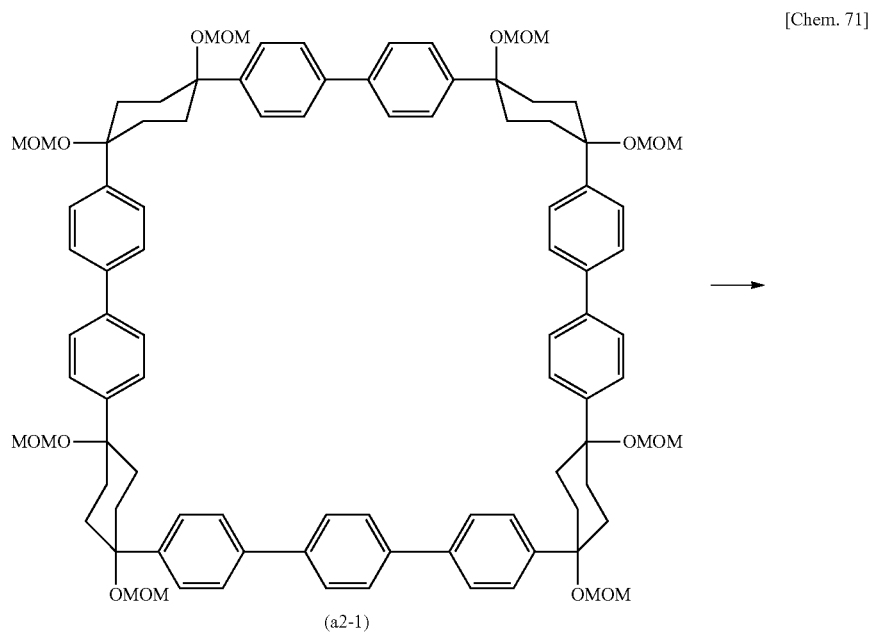

(a2-1)

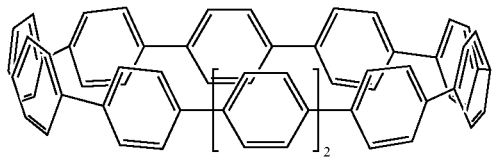

In the formula, MOM represents a methoxymethyl group.

To a 20-mL Schlenk flask containing a stirring bar and a condenser were added Compound (a2-1) (4.0 mg, 2.7 µmol) obtained in Example 5, sodium hydrogen sulfate monohydrate (NaHSO$_4$.H$_2$O) (7.4 mg, 54 µmol), o-chloranil (3.3 mg, 13 µmol), dry dimethylsulfoxide (DMSO) (1.5 mL), and dry m-xylene (4 mL). The flask was heated at 150° C. for 48 hours while stirring. After being cooled to room temperature, the resulting mixture was quenched with a saturated sodium hydrogen carbonate (NaHCO$_3$) aqueous solution, and filtration was performed through Celite using ethyl acetate (EtOAc) as a solvent. The resulting product was extracted with ethyl acetate (EtOAc), and the organic phase was dried over Na$_2$SO$_4$ and concentrated under reduced pressure. Subsequently, TLC (hexane/CH$_2$Cl$_2$=1/1) was performed to yield the target compound as a yellow solid (9.3 mg) (yield: 20%).

$^1$H NMR (600 MHz, CDCl$_3$) δ 7.64 (s, 52H); $^{13}$C NMR (150 MHz, CDCl$_3$) δ 127.4 (CH), 138.7 (4°); HRMS (MALDI) m/z calcd for C$_{78}$H$_{52}$ [M·]$^+$: 988.4064, found: 988.4086.

As described above, it was possible to freely and selectively synthesize various cyclic compounds as a pure substance, including a cyclic compound having a number of rings, which could not previously be selectively synthesized as a pure substance. This indicates that it is possible for the method of the present invention to selectively synthesize, as a pure substance, cyclic compounds having various numbers of rings, other than the above, in a simple manner.

Synthesis Example 10

Compound (IIIa-1)

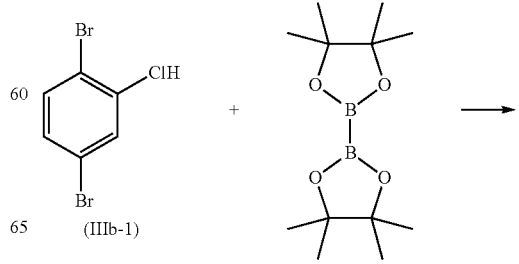

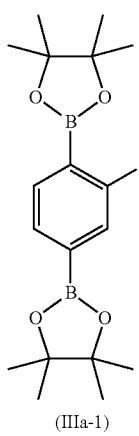

(IIIa-1)

To a 50-mL Schlenk flask containing a stirring bar were added 1,4-dibromo-2-chlorobenzene (IIIb-1) (136 mg, 0.5 mmol), bis(pinacolate)diboron (320 mg, 1.25 mmol), 1,1'-bis(diphenylphosphino) ferrocene-palladium(II)dichloride ($PdCl_2(dppf)$) (12.8 mg, 15 μmol), potassium acetate (KOAc) (148 mg, 1.5 mmol), and dry 1,4-dioxane (5 mL). The Schlenk flask was heated at 80° C. for 6 hours while stirring. After being cooled to room temperature, the reaction mixture was filtered through silica gel and washed with ethyl acetate (EtOAc). The solvent was then removed under reduced pressure. The crude product was purified by silica gel column chromatography (hexane/EtOAc=10/1) to yield the target compound as a white solid (133 mg) (yield: 72%).

$^1$H NMR (270 MHz $CDCl_3$) δ1.34 (s, 12H), 1.37 (s, 12H), 7.62 (d, J=7 Hz, 1H), 7.66 (d, J=7 Hz, 1H), 7.76 (s, 1H); $^{13}$C NMR (150 MHz, $CDCl_3$) δ24.9 ($CH_3$), 84.2 (4°), 131.7 (CH), 135.2 (CH), 135.6 (CH), 139.1 (4°); HRMS (FAB) m/z calcd for $C_{18}H_{27}B_2ClNaO_4[M \cdot Na]^+$: 387.1676, found 387.1668.

Synthesis Example 11

Compound (5'a)

[Chem. 73]

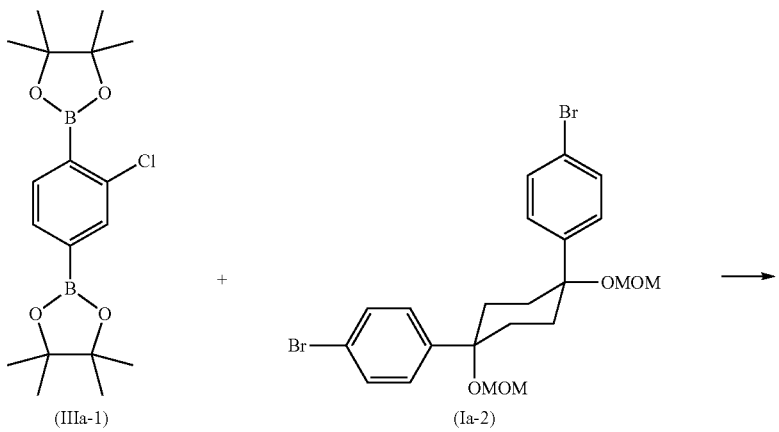

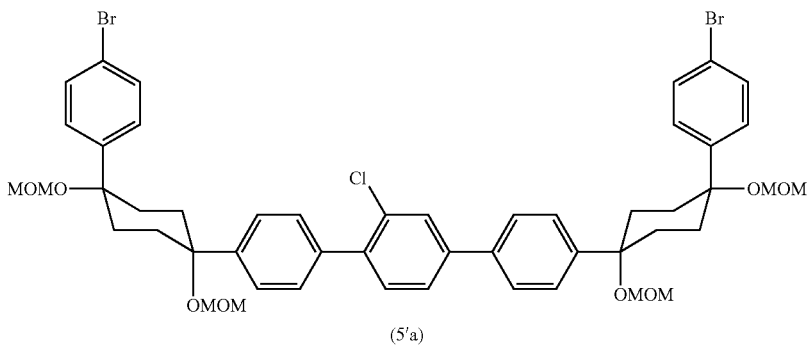

(5'a)

In the formula, MOM represents a methoxymethyl group.

To a 100-mL round-bottom flask containing a stirring bar were added Compound (IIIa-1) (369 mg, 1.01 mmol) obtained in Synthesis Example 10, Compound (Ia-2) (5.12 g, 10.0 mmol) obtained in Synthesis Example 2, tetrakis(triphenylphosphine)palladium(0) (Pd(PPh$_3$)$_4$) (50.1 mg, 43.4 μmol), silver carbonate (Ag$_2$CO$_3$) (1.10 g, 4.0 mmol), and dry THF (20 mL). The resulting mixture was reacted at 60° C. for 24 hours while stirring. After being cooled to room temperature, the resulting product was extracted with ethyl acetate (EtOAc), dried over Na$_2$SO$_4$, and concentrated under reduced pressure. The crude product was purified by silica gel column chromatography (hexane/EtOAc=5/1 to 3/1) to yield the target compound as a white solid (716 mg) (yield: 72%).

$^1$H NMR (270 MHz CDCl$_3$) δ2.11 (br, 8H), 2.35 (br, 8H), 3.40 (s, 3H), 3.41 (s, 3H), 3.43 (s, 3H), 3.44 (s, 3H), 4.43 (s, 4H), 4.47 (s, 2H), 4.49 (s, 2H), 7.32-7.38 (m, 5H), 7.44-7.58 (m, 13H), 7.67 (d, J=2 Hz, 1H); $^{13}$C NMR (67.8 MHz, CDCl$_3$) δ 32.9 (br, CH$_2$), 56.00 (CH$_3$), 56.07 (CH$_3$), 56.1, (CH$_3$), 56.0 (CH$_3$), 77.8 (4°), 77.9) (4°), 77.97 (4°), 78.00 (4°), 92.07 (CH$_3$), 92.12 (CH$_3$), 92.2 (CH$_3$), 92.3 (CH$_3$), 121.6 (4°), 121.7 (4°), 125.4 (CH), 126.4 (CH), 126.9 (CH), 127.4 (CH), 128.4 (4°), 128.7 (4°), 128.8 (4°), 129.4 (CH), 131.5 (CH), 131.6 (CH), 132.8 (4°), 138.2 (4°), 138.5 (4°), 138.7) (4°), 141.0 (4°). HRMS (FAB) m/z calcd for C$_{50}$H$_{55}$Br$_2$ClNaO$_8$[M·Na]$^+$: 999.1844, found 999.1831.

When the reaction conditions were changed, and the same reaction was performed as described above, the following yields were obtained. Table 1 shows the results. In Table 1, Pd(OAc)$_2$ represents palladium acetate (II), XPhos represents 2-(dicyclohexylphosphino)-2',4',6'-triisopropyl-1,1'-biphenyl, and Pd(PPh$_3$)$_4$ represents tetrakis(triphenylphosphine) palladium(0).

TABLE 1

| IIIa-1 (mmol) | Ia-2 (eq.) | Pd Catalyst Type | Amount (mol %) | Base Type | Amount (eq.) | Solvent | Yield (%) |
|---|---|---|---|---|---|---|---|
| 0.05 | 10 | Pd(OAc)$_2$/XPhos | 10 | NaOH | 5 | Dioxane | 36 |
| 0.05 | 10 | Pd(PPh$_3$)$_4$ | 10 | NaOH | 5 | THF | 42 |
| 0.05 | 10 | Pd(PPh$_3$)$_4$ | 10 | Ag$_2$CO$_3$ | 4 | THF | 58 |
| 0.2 | 10 | Pd(PPh$_3$)$_4$ | 10 | Ag$_2$CO$_3$ | 4 | THF | 63 |
| 1.0 | 10 | Pd(PPh$_3$)$_4$ | 8 | Ag$_2$CO$_3$ | 4 | THF | 58 |
| 1.0 | 10 | Pd(PPh$_3$)$_4$ | 5 | Ag$_2$CO$_3$ | 4 | THF | 72 |

Example 10

Compound (b2-1) Part 1

[Chem. 74]

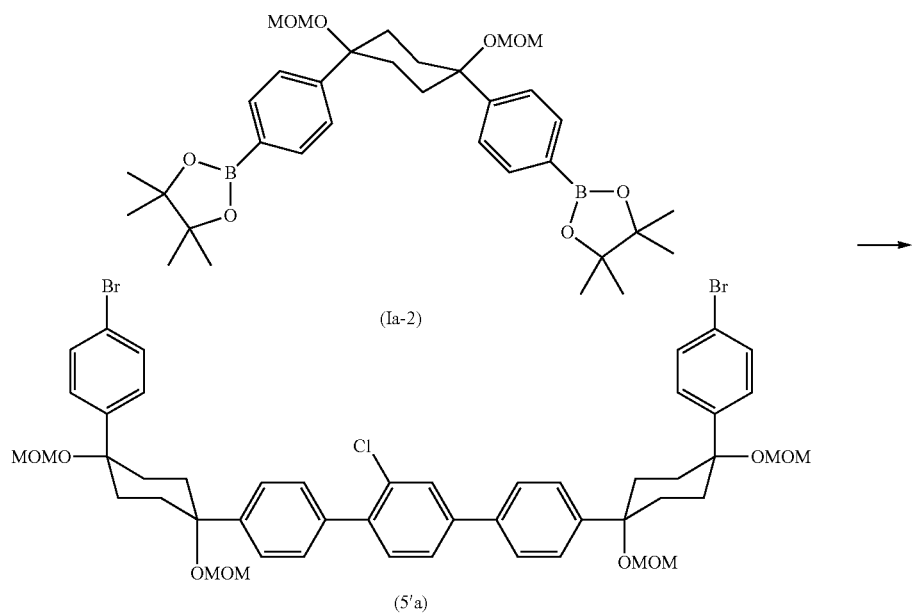

(Ia-2)

(5'a)

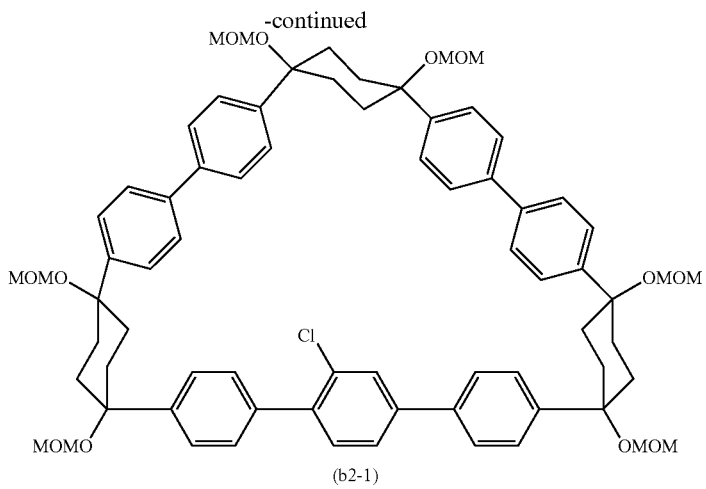

(b2-1)

In the formula, MOM represents a methoxymethyl group.

To a 50-mL Schlenk flask containing a stirring bar were added Compound (5'a) (10.0 mg, 10 µmol) obtained in Synthesis Example 11, Compound (Ia-2) (8.7 mg, 14 µmol) obtained in Synthesis Example 2, palladium acetate (II) (Pd(OAc)$_2$) (0.4 mg, 2.0 µmol), 2-(dicyclohexylphosphino)-2',6'-dimethoxy-1,1'-biphenyl (S-Phos) (0.8 mg, 2.0 µmol), and dry 1,4-dioxane (10 mL). An aqueous sodium hydroxide solution (5 µL, 10 M) was further added to the resulting mixture, and reacted at 90° C. for 24 hours while stirring. After being cooled to room temperature, the reaction mixture was filtered through silica gel (solvent: ethyl acetate). Thereafter, TLC (CH$_2$Cl$_2$/EtOAc=2/1) was performed to yield the target compound as a white solid (2.7 mg) (yield: 23%).

$^1$H NMR (400 MHz CDCl$_3$) δ2.16 (br, 12H), 2.34 (br, 12H), 3.40-3.42 (m, 18H), 4.42-4.46 (m, 12H), 7.42-7.53 (m, 27H). HRMS (FAB) m/z calcd for C$_{72}$H$_{81}$ClNaO$_{12}$[M·Na]$^+$: 1195.5309, found: 1195.5297.

When the same procedure was performed as described above, except that 2-(dicyclohexylphosphino)-2',4',6'-triisopropyl-1,1'-biphenyl (X-Phos) was used in place of S-Phos above as a ligand, as well, a yield of 22% was obtained.

In the Example above, the reaction was performed using Compound (5'a) at a concentration of 1 mM; when the concentration was 2 mM, as well, the yield was 23%.

Example 11

Compound (b2-1) Part 2

[Chem. 75]

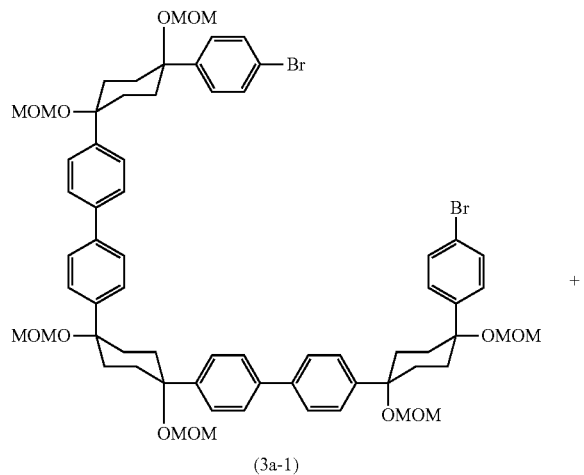

(3a-1)

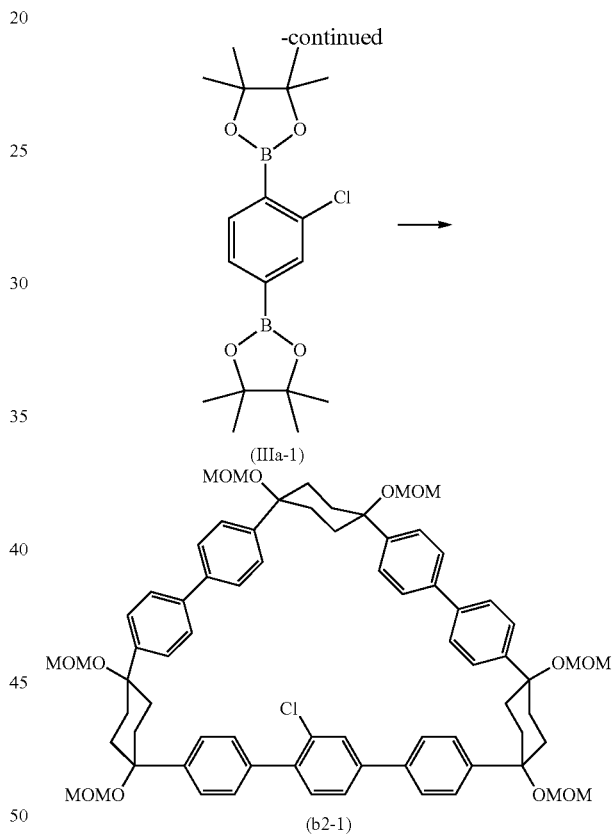

(IIIa-1)

(b2-1)

In the formula, MOM represents a methoxymethyl group.

To a 50-mL Schlenk flask containing a stirring bar were added Compound (3a-1) (25.5 mg, 21 µmol) obtained in Synthesis Example 4, Compound (IIIa-1) (12.5 mg, 34 µmol) obtained in Synthesis Example 10, palladium acetate (II) (Pd(OAc)$_2$) (1.7 mg, 49 µmol), 2-(dicyclohexylphosphino)-2',4',6'-triisopropyl-1,1'-biphenyl (X-Phos) (1.5 mg, 67 µmol), and dry 1,4-dioxane (20 mL). An aqueous sodium hydroxide solution (20 µL, 10 M) was further added to the resulting mixture, and reacted at 80° C. for 24 hours while stirring. After being cooled to room temperature, the reaction mixture was filtered through silica gel (solvent: ethyl acetate). Thereafter, TLC (CH$_2$Cl$_2$/EtOAc=2/1) was performed to yield the target compound as a white solid (8.2 mg) (yield: 34%).

$^1$H NMR (400 MHz CDCl$_3$) δ2.16 (br, 12H), 2.34 (br, 12H), 3.40-3.42 (m, 18H), 4.42-4.46 (m, 12H), 7.42-7.53 (m, 27H). HRMS (FAB) m/z calcd for C$_{72}$H$_{81}$ClNaO$_{12}$[M·Na]$^+$: 1195.5309, found: 1195.5297.

When the amount of Compound (3a-1) was changed to 0.12 mmol (upon this change, the amount of Compound (IIIa-1) was increased to 1.4 eq), the yield was about 16 to 27%.

Example 12

Compound (b3)

In the formula, MOM represents a methoxymethyl group.

To a 50-mL Schlenk flask containing a stirring bar were added Compound (5'a) (44.9 mg, 45.8 μmol) obtained in Synthesis Example 11, Compound (6a) (49.0 mg, 64.4 μmol) obtained in Synthesis Example 7, palladium acetate (II) (Pd (OAc)$_2$) (3.0 mg, 13.4 μmol), 2-(dicyclohexylphosphino)-2', 4',6'-triisopropyl-1,1'-biphenyl (X-Phos) (8.9 mg, 18.4 μmol), and dry 1,4-dioxane (46 mL). An aqueous sodium hydroxide solution (46 μL, 10 M, 0.46 mmol) was further added to the resulting mixture, and reacted at 80° C. for 24 hours while stirring. After being cooled to room temperature, the reaction mixture was filtered through silica gel (solvent:

[Chem. 76]

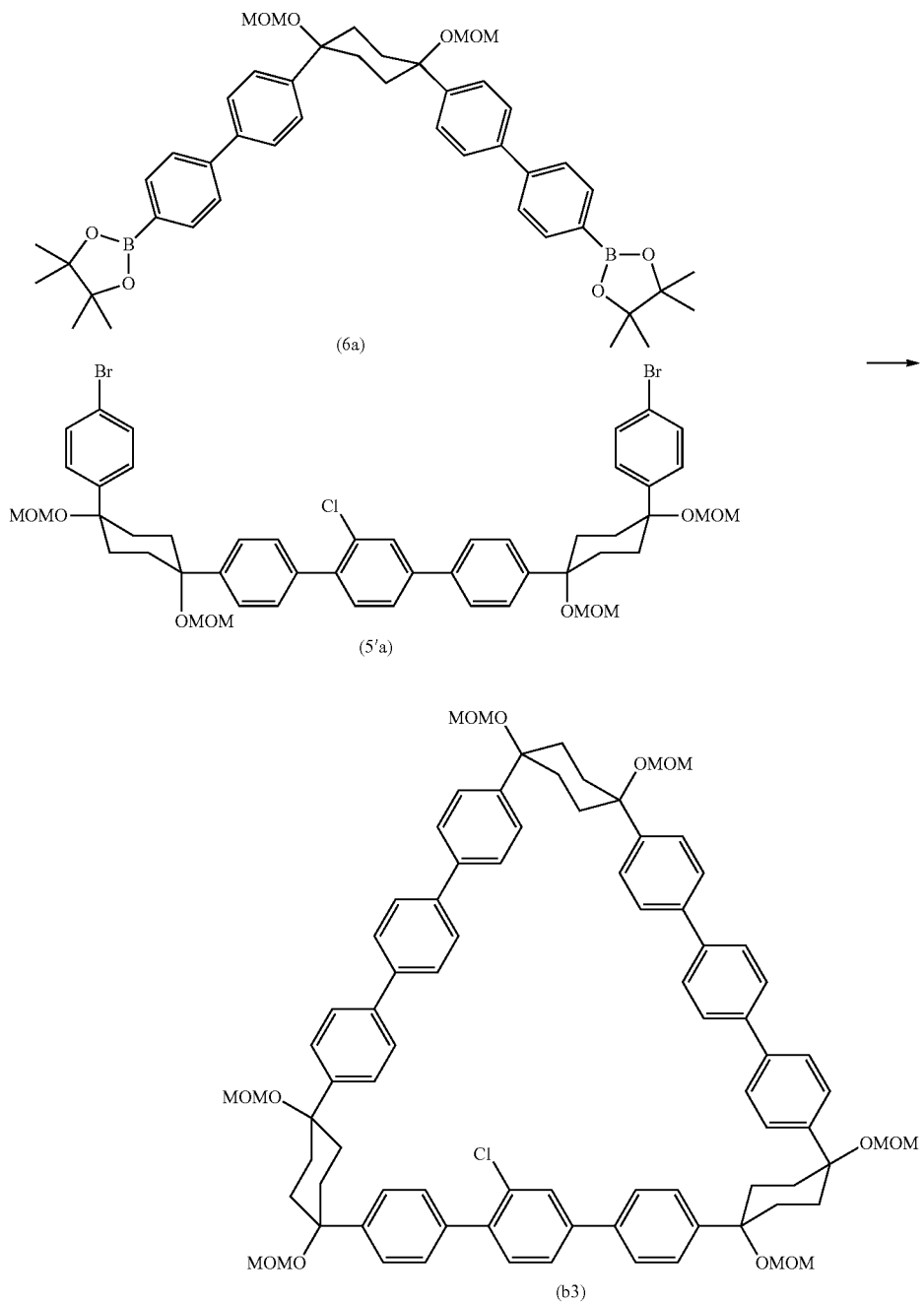

ethyl acetate). Thereafter, TLC (CH$_2$Cl$_2$/EtOAc=2/1) was performed to yield the target compound as a white solid (6.5 mg) (yield: 11%).

$^1$H NMR (400 MHz, CDCl$_3$) δ2.16 (br, 12H), 2.39 (br, 12H), 3.45 (s, 18H), 4.49 (s, 12H), 7.42-7.71(m, 35H); $^{13}$C NMR (100 MHz, CDCl$_3$) δ29.7 (br, (CH$_3$), 56.0 (CH$_3$), 78.2 (br, 4°), 92.2 (CH$_3$), 125.4, 126.5, 126.9, 127.0, 127.3, 128.4, 128.8, 129.4, 131.5, 131.6, 139.5, 139.7, 140.3, 140.5; LRMS (FAB) m/z calcd for C$_{84}$H$_{90}$ClO$_{12}$ [M·H]$^+$: 1325.6115, found 1326.

As described above, in Example 12, the reaction did not proceed at a yield as high as that obtained in Example 10.

Example 13

Compound (b1-1)

In the formula, MOM represents a methoxymethyl group.

To a 50-mL Schlenk flask containing a stirring bar were added Compound (5'a) (13.0 mg, 13.2 μmol) obtained in Synthesis Example 11, Compound (5a-2) (18.7 mg, 18.0 μmol) obtained in Synthesis Example 6, palladium acetate (II) (Pd (OAc)$_2$) (0.6 mg, 2.6 μmol), 2-(dicyclohexylphosphino)-2', 4',6'-triisopropyl-1,1'-biphenyl (X-Phos) (2.5 mg, 5.1 μmol), and dry 1,4-dioxane (6.5 mL). An aqueous sodium hydroxide solution (13 μL, 10 M, 13 mmol) was further added to the resulting mixture, and reacted at 80° C. for 24 hours while stirring. After being cooled to room temperature, the reaction mixture was filtered through silica gel (solvent: ethyl acetate). Thereafter, TLC (CH$_2$Cl$_2$/EtOAc=1/1) was performed to yield the target compound as a white solid (7.2 mg) (yield: 21%).

[Chem. 77]

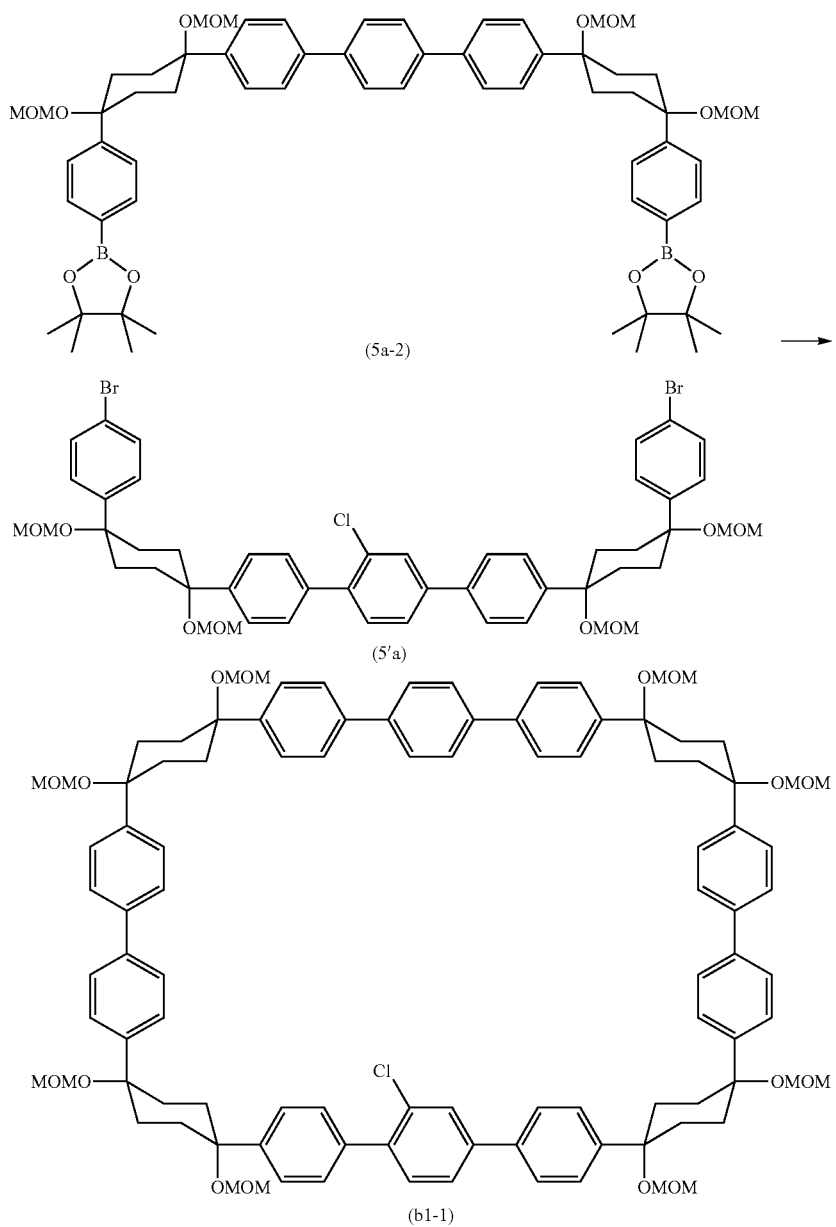

$^1$H NMR (400 MHz, CDCl$_3$) δ2.17 (br, 16H), 2.39 (br, 16H), 3.43 (s, 12H), 3.44 (s, 12H), 4.44-4.50 (m, 16H), 7.43-7.63(m, 39H); $^{13}$C NMR (98.52 MHz, CDCl$_3$) δ33.0 (CH$_2$), 56.0 (CH$_3$), 78.1 (4°), 92.2 (CH$_2$), 125.3 (CH), 126.4 (4°), 126.8 (CH), 127.3 (CH), 128.3 (CH), 128.5 (CH), 128.7 (CH), 129.4 (CH), 131.4 (CH), 131.5(CH), 131.6 (CH), 132.7 (4°), 138.0 (4°), 138.4 (4°), 138.6 (4°), 139.4 (4°), 139.5 (4°), 139.6 (4°), 141.0 (4°), 141.5 (br, 4°); HRMS (FAB) m/z calcd for C$_{100}$H$_{111}$ClNaO$_{16}$ [M·Na]$^+$: 1625.7453, found 1625.7483.

Example 14

Chloro[10]cycloparaphenylene

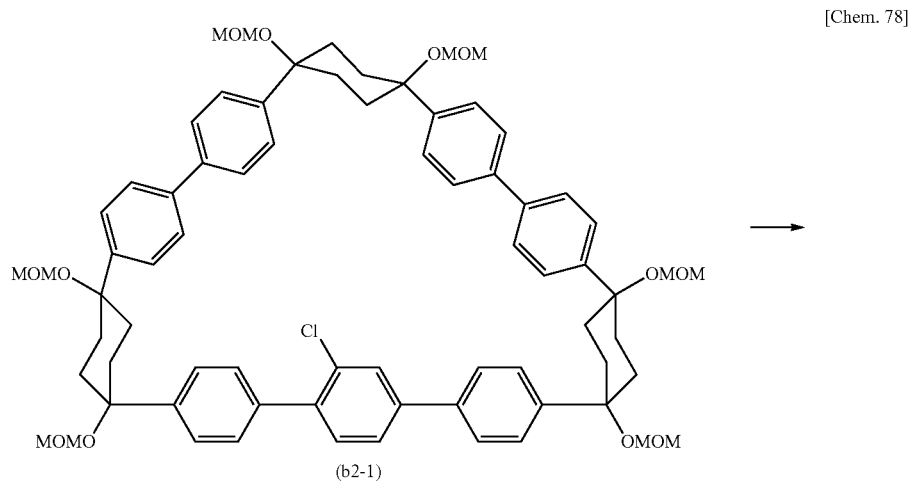

(b2-1)

In the formula, MOM represents a methoxymethyl group.

To a 20-mL Schlenk flask containing a stirring bar and a condenser were added Compound (b2-1) (47.3 mg, 40.3 μmol) obtained in Example 10 or 11, sodium hydrogen sulfate monohydrate (NaHSO$_4$·H$_2$O) (113 mg, 0.81 μmol), o-chloranil (50.0 mg, 0.20 mmol), dry dimethylsulfoxide (DMSO) (1.3 mL), and dry m-xylene (5 mL). The flask was heated at 150° C. for 48 hours while stirring. After being cooled to room temperature, the resulting product was extracted with ethyl acetate (EtOAc), dried over Na$_2$SO$_4$, and concentrated under reduced pressure. Thereafter, TLC (CH$_2$Cl$_2$/hexane=1/1) was performed to yield the target compound as a yellow solid (5.7 mg) (yield: 18%).

$^1$H NMR (400 MHz, CDCl$_3$) δ7.50-7.66 (m, 38H), 7.78 (d, J=2 Hz, 1H); $^{13}$C NMR (150.8 MHz, CDCl$_3$) δ127.0, 127.18, 127.24, 127.3, 127.42, 127.44, 127.5, 127.6, 127.8, 127.9, 128.0, 129.1, 132.4, 133.4, 133.9, 137.6, 137.65, 137.68, 137.8, 137.9, 138.1, 138.16, 138.19, 138.25, 138.32, 138.4, 138.5, 138.6, 138.8, 138.9, 139.0, 139.1, 139.6, 139.9, 141,5; HRMS (MALDI-TOF) m/z calcd for C$_{60}$H$_{39}$Cl [M·]$^+$: 794.2740, found 794.2743.

[Chem. 78]

→

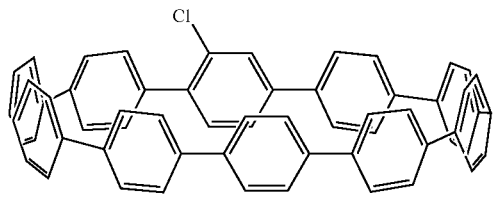

Example 15

Chloro[12]cycloparaphenylene

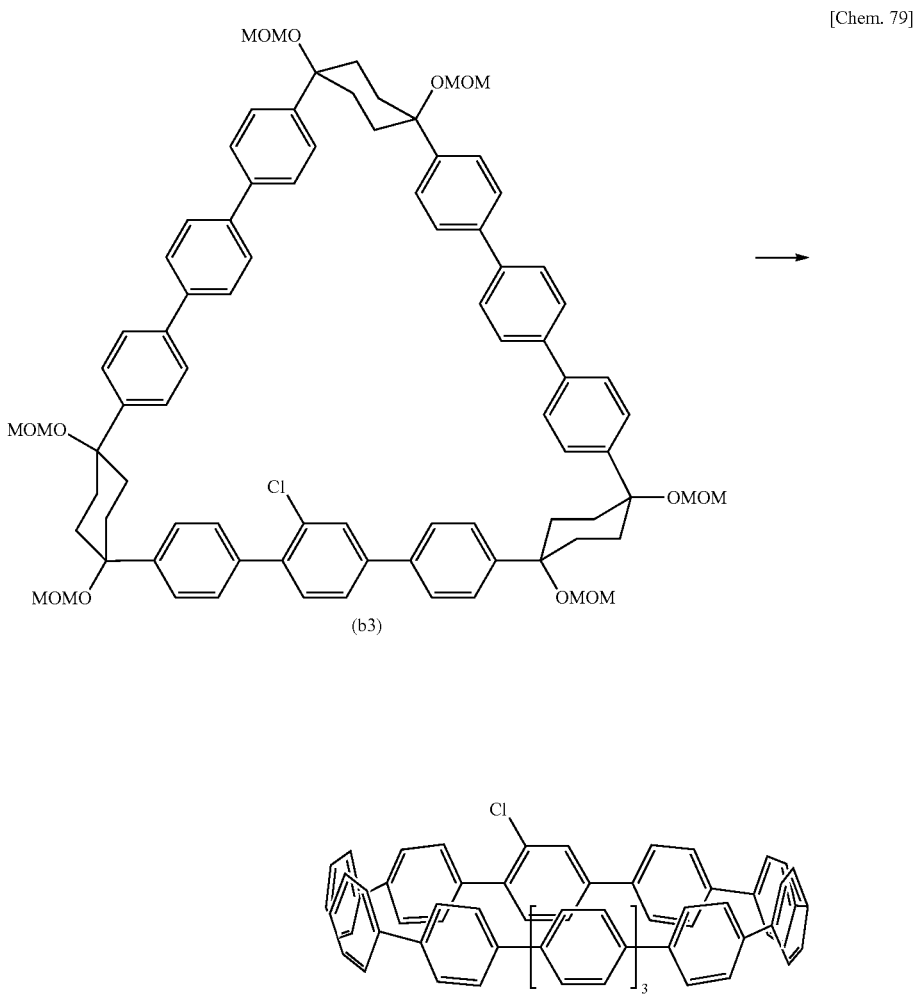

In the formula, MOM represents a methoxymethyl group.

To a 20-mL Schlenk flask containing a stirring bar and a condenser were added Compound (b3) (4.2 mg, 3.17 μmol) obtained in Example 12, sodium hydrogen sulfate monohydrate ($NaHSO_4 \cdot H_2O$) (30.0 mg, 0.22 mmol), o-chloranil (2.8 mg, 11.3 μmol), dry dimethylsulfoxide (DMSO) (0.2 mL), and dry m-xylene (0.7 mL). The flask was heated at 150° C. for 48 hours while stirring. After being cooled to room temperature, the resulting product was extracted with ethyl acetate (EtOAc), dried over $Na_2SO_4$, and concentrated under reduced pressure. Thereafter, TLC ($CH_2Cl_2$/hexane=1/1) was performed to yield the target compound as a yellow solid (0.4 mg) (yield: 13%).

$^1$H NMR (400 MHz, $CDCl_3$) δ7.58-7.64 (m, 46H), 7.80 (d, J=2Hz, 1H); HRMS (MALDI-TOF) m/z calcd for $C_{72}H_{47}Cl$ $[M \cdot]^+$: 946.3366, found 947.0030.

Example 16

Chloro[14]cycloparaphenylene

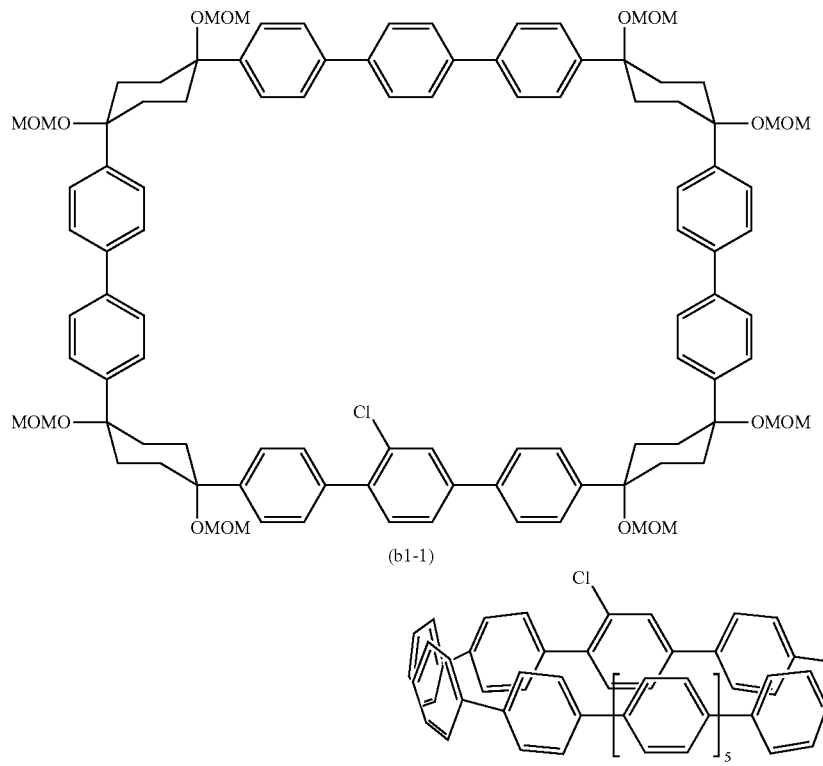

(b1-1)

In the formula, MOM represents a methoxymethyl group.

To a 20-mL Schlenk flask containing a stirring bar and a condenser were added Compound (b1-1) (15.2 mg, 9.47 μmol) obtained in Example 13, sodium hydrogen sulfate monohydrate (NaHSO$_4$.H$_2$) (26.7 mg, 0.19 mmol), o-chloranil (12.2 mg, 47.3 pmol), dry dimethylsulfoxide (DMSO) (0.6 mL), and dry m-xylene (2.0 mL). The flask was heated at 150° C. for 48 hours while stirring. After being cooled to room temperature, the resulting product was extracted with ethyl acetate (EtOAc), dried over Na$_2$SO$_4$, and concentrated under reduced pressure. Thereafter, TLC (CH$_2$Cl$_2$/hexane=1/1) was performed to yield the target compound as a yellow solid (3.5 mg) (yield: 32%).

$^1$HNMR (400 MHz, CDCl$_3$) δ7.18 (d, J=8 Hz, 1H), 7.31 (d, J=8 Hz, 1H), 7.60-7.72 (m, 53H), 7.81 (s, 1H); $^{13}$C NMR (100 MHz, CDCl$_3$) δ127.0 (CH)127.0 (CH), 127.3 (CH), 127.47 (CH), 127.54 (CH), 127.7 (CH), 129.6 (CH), 132.0 (4°), 133.2 (CH), 137.8 (4°), 137.9 (4°), 138.0 (4°), 138.6 (4°), 138.7 (4°), 138.8 (4°), 139.0 (4°), 139.2 (4°), 139.7 (4°), 140.5 (4°); HRMS (MALDI-TOF) m/z calcd for C$_{84}$H$_{55}$Cl [M·]$^+$: 1098.3992, found 1099.2469.

A comparison of the results of Examples 14 to 16 reveals that the reaction in Example 16 proceeded in a high yield, compared with Examples 14 and 15. In view of this, the difference in strain energy generated by the ring size difference is assumed to be involved in the aromatization reaction.

As described above, it was possible to introduce a functional group into a desired portion of a cyclic compound having high symmetry, such as cycloparaphenylene. Such an introduction was previously considered to be difficult. The method of the present invention enables the introduction of functional groups into cyclic compounds having a different number of rings. By-products in which the reaction site was the chloro group were not produced in any of the Examples during the synthesis process of the present invention.

Example 17 p-Anisylated [10]cycloparaphenylene

[Chem. 81]

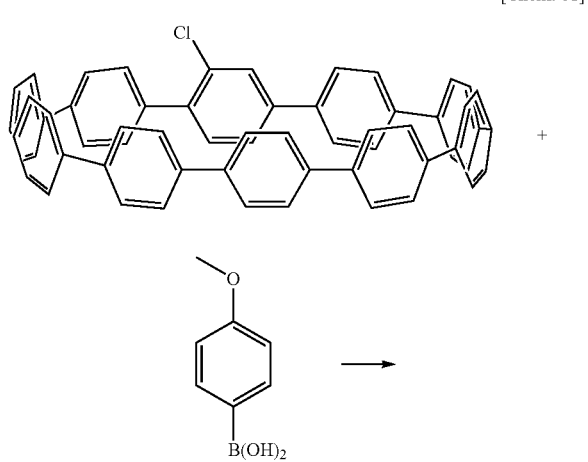

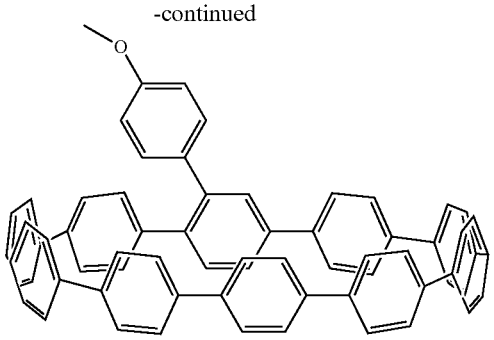

To a 20-mL Schlenk flask containing a stirring bar were added chloro[10]cycloparaphenylene (4.6 mg, 5.8 μmol) obtained in Example 14, 4-methoxyphenylboronic acid (1.7 mg, 11.2 μmol), tris(dibenzylideneacetone)dipalladium(0) (Pd$_2$(dba)$_3$) (0.6 mg, 0.57 μmol), 2-(dicyclohexylphosphino)-2',4',6'-triisopropyl-1,1'-biphenyl (X-Phos) (0.6 mg, 1.2 μmol), potassium phosphate (K$_3$PO$_4$) (2.7 mg, 11.7 μmol), dry N,N-dimethylformamide (DMF) (0.45 mL), and water (0.05 mL). The flask was heated at 135° C. for 23 hours while stirring. After the resulting product was cooled to room temperature, extraction was performed with ethyl acetate (EtOAc). Thereafter, TLC (CH$_2$Cl$_2$/hexane=1/1) was performed to yield the target compound as a white solid (0.5 mg) (yield: 10%).

$^1$H NMR (600 MHz, CDCl$_3$) δ 3.84 (s, 3H), 6.93 (m, 2H), 7.08 (d, J=8 Hz, 1H), 7.12 (d, J=8 Hz, 1H), 7.43-7.60 (m, 38H), 7.89 (d, J=10 Hz, 1H); HRMS (MALDI-TOF) m/z calcd for C$_{67}$H$_{46}$O [M·]$^+$: 866.3549, found 866.5002.

As described above, it was found that the functional groups introduced in Examples 14 to 16 can be replaced with other functional groups. In particular, even in terms of a functional group that cannot be easily introduced during the synthesis process, the introduction thereof into a cyclic compound can be easily performed by first synthesizing a cyclic compound into which an easily introduced functional group is introduced, and then replacing the easily introduced functional group with a desired functional group. Therefore, it is possible to introduce various other functional groups into cyclic compounds, such as a cycloparaphenylene compound.

The p-anisylated [10]cycloparaphenylene obtained in Example 17 showed a polarity slightly higher than that of the chloro[10]cycloparaphenylene obtained in Example 14. When irradiated with a 365 nm UV lamp, both the p-anisylated [10]cycloparaphenylene and chloro[10]cycloparaphenylene showed light-blue fluorescence.

The invention claimed is:

1. A cyclic compound containing a functional group, wherein the cyclic compound has 10 or more bivalent aromatic hydrocarbon groups or bivalent heterocyclic groups and one or more of the bivalent aromatic hydrocarbon groups or bivalent heterocyclic groups are a group represented by General Formula (2):

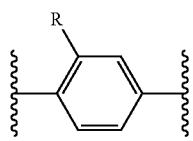

wherein R is halogen atoms, aryl groups optionally substituted with a substituent, alkoxy groups, hydroxy group, boryl groups, silyl groups, or amino group.

2. The cyclic compound containing a functional group according to claim 1, wherein the cyclic compound has 1 group represented by General Formula (2), and 9 or more bivalent aromatic hydrocarbon groups or bivalent heterocyclic groups.

3. The cyclic compound containing a functional group according to claim 1, wherein R is a halogen atom.

4. A method for producing the cyclic compound containing a functional group according to claim 1, comprising the step of converting cyclohexane rings of a cyclic compound, which has one or more groups represented by General Formula (2); 3 to 4 groups represented by General Formula (1):

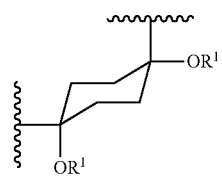

wherein R$^1$ is the same or different, and each represents a hydrogen atom or a protecting group for a hydroxy group;
and 6 or more bivalent aromatic hydrocarbon groups or bivalent heterocyclic groups, into benzene rings.

5. The method according to claim 4, further comprising the step of reacting a compound containing no functional group with a compound containing a functional group to obtain the cyclic compound, wherein the compound containing no functional group is a compound obtained by reacting one kind of compound or two or more kinds of compounds selected from the group consisting of a compound represented by General Formula (I):

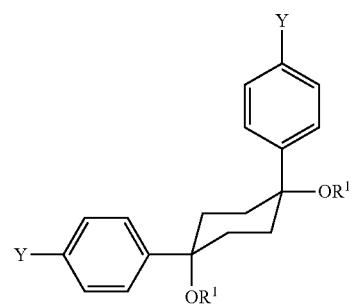

wherein R$^1$ is as defined above; Y is the same or different, and each represents a halogen atom, or a boronic acid or an ester thereof; and
a compound represented by General Formula (II):

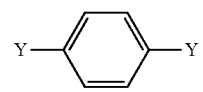

wherein Y is as defined above,
the compound containing a functional group is a compound represented by General Formula (III):

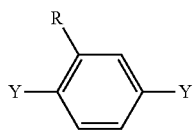

wherein R and Y are as defined above,
or a compound obtained by reacting the compound represented by General Formula (III) with at least one kind of the compound containing no functional group.

6. The method according to claim 5, wherein the compound containing no functional group is a compound represented by General Formula (VII-1):

wherein $R^2$ is a bivalent group containing 1 to 3 structural units represented by General Formula (1) and 2 or more bivalent aromatic hydrocarbon groups or bivalent heterocyclic groups; and Y is as defined above,
and the compound containing a functional group is a compound represented by General Formula (VII-2):

wherein $R^3$ is a bivalent group containing one or more structural units represented by General Formula (2), 0 to 2 structural units represented by General Formula (1), and 0 or more bivalent aromatic hydrocarbon groups or bivalent heterocyclic groups; and Y is as defined above.

7. A cyclic compound having one or more groups represented by General Formula (2):

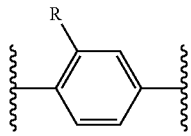

wherein R is halogen atoms, aryl groups optionally substituted with a substituent, alkoxy groups, hydroxy group, boryl groups, silyl groups, or amino group;
3 to 4 groups represented by General Formula (1):

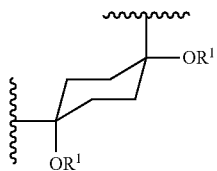

wherein $R^1$ is the same or different, and each represents a hydrogen atom or a protecting group for a hydroxy group; and
6 or more bivalent aromatic hydrocarbon groups or bivalent heterocyclic groups.

8. A method for producing the cyclic compound of claim 7, comprising the step of reacting a compound containing no functional group with a compound containing a functional group to obtain the cyclic compound, wherein the compound containing no functional group is obtained by reacting one kind of compound or two or more kinds of compounds selected from a compound represented by General Formula (I):

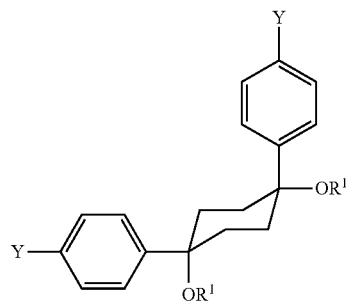

wherein $R^1$ is as defined above; Y is the same or different, and each represents a halogen atom, or a boronic acid or an ester thereof; and
a compound represented by General Formula (II):

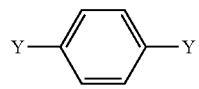

wherein Y is as defined above,
and the compound containing a functional group is a compound represented by General Formula (III):

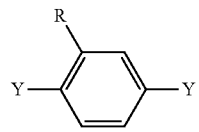

wherein R and Y are as defined above,
or a compound obtained by reacting the compound represented by General Formula (III) with at least one kind of the compound containing no functional group.

9. The method according to claim 8, wherein the compound containing no functional group is a compound represented by General Formula (VII-1):

wherein $R^2$ is a bivalent group having 1 to 3 structural units represented by General Formula (1), and 2 or more bivalent aromatic hydrocarbon groups or bivalent heterocyclic groups; and Y is as defined above,
and the compound containing a functional group is a compound represented by General Formula (VII-2):

wherein $R^3$ is a bivalent group having one or more structural units represented by General Formula (2), 0 to 2 structural units represented by General Formula (1), and 0 or more bivalent aromatic hydrocarbon groups or bivalent heterocyclic groups; and Y is as defined above.

10. A method for producing a cyclic compound having 9 to 13 bivalent aromatic hydrocarbon groups or bivalent heterocyclic groups, the method comprising the step of obtaining the cyclic compound by reacting, through an intramolecular ring closure reaction, terminal atoms of a chain compound represented by General Formula (IV):

wherein $R^4$ is a bivalent group having 3 to 4 structural units represented by General Formula (1):

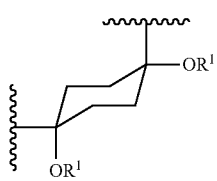

(wherein $R^1$ is the same or different, and each represents a hydrogen atom or a protecting group for a hydroxy group)

and 6 or more bivalent aromatic hydrocarbon groups or bivalent heterocyclic groups; and X is the same or different, and each represents a halogen atom.

11. A method for producing a cyclic compound having 10 to 13 bivalent aromatic hydrocarbon groups or bivalent heterocyclic groups, the method comprising the step of obtaining the cyclic compound by reacting a compound represented by General Formula (V-1):

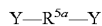
Y—$R^{5a}$—Y wherein $R^{5a}$ is a bivalent group having 3 structural units represented by General Formula (1):

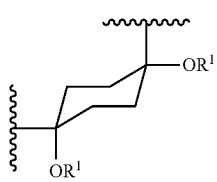

(wherein $R^1$ is the same or different, and each represents a hydrogen atom or a protecting group for a hydroxy group)

and 6 or more bivalent aromatic hydrocarbon groups or bivalent heterocyclic groups; and Y is the same or different, and each represents a halogen atom, or a boronic acid or an ester thereof, with a compound represented by General Formula (V-2):

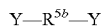
Y—$R^{5b}$—Y wherein $R^{5b}$ is a bivalent group having one or more bivalent aromatic hydrocarbon groups or bivalent heterocyclic groups; and Y is as defined above.

12. A method for producing a cyclic compound having 9 to 13 bivalent aromatic hydrocarbon groups or bivalent heterocyclic groups, the method comprising the step of obtaining the cyclic compound by reacting a compound represented by General Formula (VI-1):

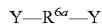
Y—$R^{6a}$—Y wherein $R^{6a}$ is a bivalent group having 2 structural units represented by General Formula (1):

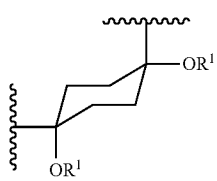

(wherein $R^1$ is the same or different, and each represents a hydrogen atom or a protecting group for a hydroxy group)

and 4 or more bivalent aromatic hydrocarbon groups or bivalent heterocyclic groups; and Y is the same or different, and each represents a halogen atom, or a boronic acid or an ester thereof, with a compound represented by General Formula (VI-2):

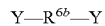
Y—$R^{6b}$—Y wherein $R^{6b}$ is a bivalent group having 1 structural unit represented by General Formula (1) and 2 or more bivalent aromatic hydrocarbon groups or bivalent heterocyclic groups; and Y is as defined above.

13. A cyclic compound having 3 to 4 structural units represented by General Formula (1):

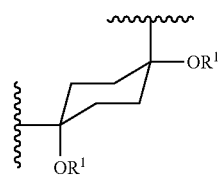

wherein $R^1$ is the same or different, and each represents a hydrogen atom or a protecting group for a hydroxy group, and 6 to 9 bivalent aromatic hydrocarbon groups or bivalent heterocyclic groups, the cyclic compound having 10 or 11 structural units represented by General Formula (1) and bivalent aromatic hydrocarbon groups or bivalent heterocyclic groups in total.

14. A method for producing a cyclic compound having 3 to 4 structural units represented by General Formula (1):

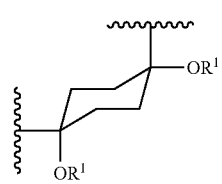

wherein $R^1$ is the same or different, and each represents a hydrogen atom or a protecting group for a hydroxy group, and 6 to 9 bivalent aromatic hydrocarbon groups or bivalent heterocyclic groups, the cyclic compound having 10, 11, or 13 structural units represented by General Formula (1) and bivalent aromatic hydrocarbon groups or bivalent heterocyclic groups in total, comprising the step of reacting, through an intramolecular ring closure reaction, terminal atoms of a chain compound represented by General Formula (IV):

X—$R^4$—X wherein $R^4$ is a bivalent group having 3 to 4 structural units represented by General Formula (1):

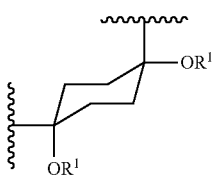

(wherein $R^1$ is as defined above),
and 6 or more bivalent aromatic hydrocarbon groups or bivalent heterocyclic groups; and X is the same or different, and each represents a halogen atom.

15. A method for producing a cyclic compound having 3 to 4 structural units represented by General Formula (1):

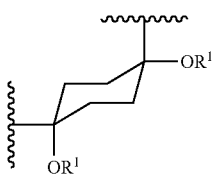

wherein $R^1$ is the same or different, and each represents a hydrogen atom or a protecting group for a hydroxy group,
and 6 to 9 bivalent aromatic hydrocarbon groups or bivalent heterocyclic groups,
the cyclic compound having 10, 11, or 13 structural units represented by General Formula (1) and bivalent aromatic hydrocarbon groups or bivalent heterocyclic groups in total,
comprising the step of obtaining the cyclic compound by reacting a compound represented by General Formula (V-1):

$$Y-R^{5a}-Y$$

wherein $R^{5a}$ is a bivalent group having 3 structural units represented by General Formula (1) and 6 or more bivalent aromatic hydrocarbon groups or bivalent heterocyclic groups; and Y is the same or different, and each represents a halogen atom, or a boronic acid or an ester thereof,
with a compound represented by General Formula (V-2):

$$Y-R^{5b}-Y$$

wherein $R^{5b}$ is a bivalent group having one or more bivalent aromatic hydrocarbon groups, bivalent heterocyclic groups; and Y is as defined above.

16. A method for producing a cyclic compound having 3 to 4 structural units represented by General Formula (1):

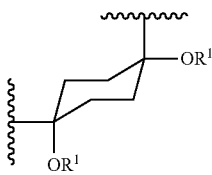

wherein $R^1$ is the same or different, and each represents a hydrogen atom or a protecting group for a hydroxy group,
and 6 to 9 bivalent aromatic hydrocarbon groups or bivalent heterocyclic groups,
the cyclic compound having 10, 11, or 13 structural units represented by General Formula (1) and bivalent aromatic hydrocarbon groups or bivalent heterocyclic groups in total,
comprising the step of obtaining the cyclic compound by reacting a compound represented by General Formula (VI-1):

$$Y-R^{6a}-Y$$

wherein $R^{6a}$ is a bivalent group having 2 structural units represented by General Formula (1) and 4 or more bivalent aromatic hydrocarbon groups or bivalent heterocyclic groups; and Y is the same or different, and each represents a halogen atom, or a boronic acid or an ester thereof,
with a compound represented by General Formula (VI-2):

$$Y-R^{6b}-Y$$

wherein $R^{6b}$ is a bivalent group having 1 structural unit represented by General Formula (1) and 2 or more bivalent aromatic hydrocarbon groups or bivalent heterocyclic groups; and Y is as defined above.

17. The cyclic compound containing a functional group according to claim 2, wherein R is a halogen atom.

18. A method for producing the cyclic compound containing a functional group according to claim 2, comprising the step of converting cyclohexane rings of a cyclic compound, which has one or more groups represented by General Formula (2);
3 to 4 groups represented by General Formula (1):

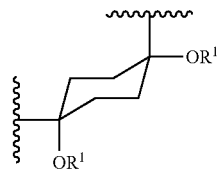

wherein $R^1$ is the same or different, and each represents a hydrogen atom or a protecting group for a hydroxy group;
and 6 or more bivalent aromatic hydrocarbon groups or bivalent heterocyclic groups, into benzene rings.

19. A method for producing the cyclic compound containing a functional group according to claim 3, comprising the step of converting cyclohexane rings of a cyclic compound, which has one or more groups represented by General Formula (2);
3 to 4 groups represented by General Formula (1):

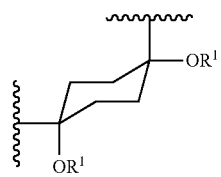

wherein $R^1$ is the same or different, and each represents a hydrogen atom or a protecting group for a hydroxy group;
and 6 or more bivalent aromatic hydrocarbon groups or bivalent heterocyclic groups, into benzene rings.

20. A method for producing the cyclic compound containing a functional group according to claim 17, comprising the step of converting cyclohexane rings of a cyclic compound, which has one or more groups represented by General Formula (2);

3 to 4 groups represented by General Formula (1):

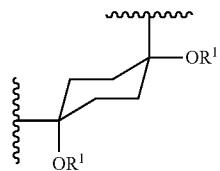

wherein $R^1$ is the same or different, and each represents a hydrogen atom or a protecting group for a hydroxy group;

and 6 or more bivalent aromatic hydrocarbon groups or bivalent heterocyclic groups, into benzene rings.

* * * * *